United States Patent
Hickey et al.

(10) Patent No.: US 8,846,936 B2
(45) Date of Patent: Sep. 30, 2014

(54) SULFONYL COMPOUNDS WHICH MODULATE THE CB2 RECEPTOR

(75) Inventors: Eugene Richard Hickey, Danbury, CT (US); Doris Riether, Biberach an der Riss (DE); Monika Ermann, Wantage (GB)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 13/809,607

(22) PCT Filed: Jul. 18, 2011

(86) PCT No.: PCT/US2011/044309
§ 371 (c)(1),
(2), (4) Date: Mar. 27, 2013

(87) PCT Pub. No.: WO2012/012307
PCT Pub. Date: Jan. 26, 2012

(65) Prior Publication Data
US 2013/0184315 A1   Jul. 18, 2013

Related U.S. Application Data

(60) Provisional application No. 61/366,660, filed on Jul. 22, 2010.

(51) Int. Cl.
| | | |
|---|---|---|
| C07D 213/72 | (2006.01) | |
| C07D 213/78 | (2006.01) | |
| C07D 261/04 | (2006.01) | |
| C07D 261/14 | (2006.01) | |
| C07D 231/00 | (2006.01) | |
| A01N 43/40 | (2006.01) | |
| A01N 43/80 | (2006.01) | |
| A61K 31/44 | (2006.01) | |
| A61K 31/42 | (2006.01) | |
| C07D 277/46 | (2006.01) | |
| C07D 285/135 | (2006.01) | |
| C07D 213/74 | (2006.01) | |
| C07D 413/12 | (2006.01) | |
| C07D 261/18 | (2006.01) | |
| C07D 231/38 | (2006.01) | |

(52) U.S. Cl.
CPC .......... *C07D 285/135* (2013.01); *C07D 277/46* (2013.01); *C07D 213/74* (2013.01); *C07D 413/12* (2013.01); *C07D 261/18* (2013.01); *C07D 261/14* (2013.01); *C07D 231/38* (2013.01)
USPC ........ 546/312; 548/245; 548/371.7; 514/352; 514/380; 514/378; 514/359; 514/406

(58) Field of Classification Search
USPC .......................................... 514/352; 546/312
See application file for complete search history.

(56) References Cited

U.S. PATENT DOCUMENTS

| | | |
|---|---|---|
| 3,116,284 A | 12/1963 | Testa |
| 3,117,128 A | 1/1964 | Mooradian |
| 3,577,462 A | 5/1971 | Bruce et al. |
| 3,794,652 A * | 2/1974 | Naito .............................. 546/193 |
| 3,966,809 A | 6/1976 | Baker et al. |
| 4,257,954 A | 3/1981 | Schmidt et al. |
| 4,535,087 A | 8/1985 | Spatz |
| 4,672,065 A | 6/1987 | Spatz |
| 4,734,125 A | 3/1988 | Gehring et al. |
| 4,859,707 A | 8/1989 | Loftsson et al. |
| 5,256,658 A | 10/1993 | Hsi et al. |
| 5,428,037 A | 6/1995 | Pascal et al. |
| 5,475,130 A | 12/1995 | Sato et al. |
| 5,491,170 A | 2/1996 | Lee et al. |
| 5,571,921 A | 11/1996 | Bender et al. |

(Continued)

FOREIGN PATENT DOCUMENTS

| | | |
|---|---|---|
| CH | 312963 A | 3/1956 |
| DE | 1080563 B | 12/1957 |

(Continued)

OTHER PUBLICATIONS

Silverman; The Organic Chemistry of Drug Design and Drug Action, 2nd Ed, 2004, Elsevier, pp. 29-34.*
Wermuth; The Practice of Medicinal Chemistry, 2008, 3rd Ed, chapter 17, pp. 363-379.*
Gao, M., et al "Synthesis of new carbon-11 labeled benzoxazole derivatives for PET imaging of 5-HT3 receptor", Science Direct, European Journal of Medicinal Chemistry, 43, 2008, pp. 1570-1574.

(Continued)

*Primary Examiner* — John Mabry
*Assistant Examiner* — Daniel Carcanague
(74) *Attorney, Agent, or Firm* — Michael P. Morris; Anthony P. Bottino

(57) ABSTRACT

Compounds of formula (I) and formula (II) are disclosed. Compounds according to the invention bind to and are agonists, antagonists or inverse agonists of the CB2 receptor, and are useful for treating inflammation. Those compounds which are agonists are additionally useful for treating pain.

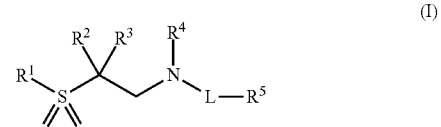

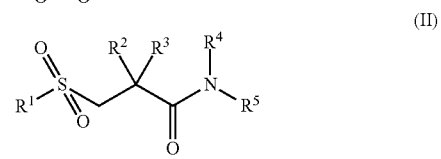

14 Claims, No Drawings

(56) References Cited

U.S. PATENT DOCUMENTS

| | | |
|---|---|---|
| 5,583,147 A | 12/1996 | Ko et al. |
| 5,656,634 A | 8/1997 | Chang et al. |
| 5,847,153 A | 12/1998 | Warpehoski et al. |
| 5,958,940 A | 9/1999 | Rane et al. |
| 5,968,929 A | 10/1999 | Blythin et al. |
| 6,057,371 A | 5/2000 | Glennon |
| 6,176,442 B1 | 1/2001 | Eicher et al. |
| 6,221,866 B1 | 4/2001 | Brendel et al. |
| 6,355,653 B1 | 3/2002 | Trottmann et al. |
| 6,359,009 B1 | 3/2002 | Diehl et al. |
| 6,410,792 B1 | 6/2002 | Connell et al. |
| 6,414,011 B1 | 7/2002 | Hogenkamp et al. |
| 6,437,177 B1 | 8/2002 | Warpehoski et al. |
| 6,453,795 B1 | 9/2002 | Eicher et al. |
| 6,528,529 B1 | 3/2003 | Brann et al. |
| 6,573,278 B2 | 6/2003 | Mittendorf et al. |
| 6,610,711 B2 | 8/2003 | Armer et al. |
| 6,737,418 B2 | 5/2004 | Hogenkamp et al. |
| 6,756,404 B2 | 6/2004 | Livinghouse |
| 6,930,115 B2 | 8/2005 | Fujii et al. |
| 7,476,756 B2 | 1/2009 | Almario-Garcia et al. |
| 7,585,881 B2 | 9/2009 | Edwards et al. |
| 7,595,397 B2 | 9/2009 | Zindell et al. |
| 7,776,897 B2 | 8/2010 | Murakami et al. |
| 7,928,123 B2 | 4/2011 | Berry et al. |
| 7,935,715 B2 | 5/2011 | Berry et al. |
| 8,048,899 B2 | 11/2011 | Bartolozzi et al. |
| 8,173,638 B2 | 5/2012 | Berry et al. |
| 8,178,568 B2 | 5/2012 | Regan et al. |
| 8,299,103 B2 | 10/2012 | Bartolozzi et al. |
| 8,299,111 B2 | 10/2012 | Berry et al. |
| 8,329,735 B2 | 12/2012 | Ermann et al. |
| 8,546,563 B2 | 10/2013 | Berry et al. |
| 2002/0099035 A1 | 7/2002 | Sandanayaka et al. |
| 2004/0067999 A1 | 4/2004 | Block et al. |
| 2004/0152747 A1 | 8/2004 | Chen et al. |
| 2004/0242666 A1 | 12/2004 | Chen |
| 2004/0242913 A1 | 12/2004 | Ducray et al. |
| 2005/0059663 A1 | 3/2005 | Martin et al. |
| 2005/0182108 A1 | 8/2005 | Carson et al. |
| 2005/0222219 A1 | 10/2005 | Chen |
| 2006/0009491 A1 | 1/2006 | Yao et al. |
| 2006/0061726 A1 | 3/2006 | Okuyama |
| 2006/0079557 A1 | 4/2006 | Dolle et al. |
| 2006/0173022 A1* | 8/2006 | Schaper ........................ 514/256 |
| 2007/0021403 A1 | 1/2007 | Abouabdellah et al. |
| 2007/0021430 A1 | 1/2007 | Chen et al. |
| 2007/0093501 A1 | 4/2007 | Kubo et al. |
| 2007/0179126 A1 | 8/2007 | Casellas et al. |
| 2007/0191340 A1 | 8/2007 | Zindell et al. |
| 2007/0213311 A1 | 9/2007 | Li et al. |
| 2007/0270426 A1 | 11/2007 | Chen |
| 2008/0039464 A1 | 2/2008 | Berry et al. |
| 2008/0064690 A1 | 3/2008 | Atkinson et al. |
| 2008/0081342 A1 | 4/2008 | Fung |
| 2008/0081822 A1 | 4/2008 | Berry et al. |
| 2008/0227781 A1 | 9/2008 | Brodney et al. |
| 2009/0163545 A1 | 6/2009 | Goldfarb |
| 2009/0275611 A1 | 11/2009 | Riether et al. |
| 2010/0009964 A1 | 1/2010 | Berry et al. |
| 2010/0029644 A1 | 2/2010 | Riether et al. |
| 2010/0076029 A1 | 3/2010 | Bartolozzi et al. |
| 2010/0081644 A1 | 4/2010 | Bartolozzi et al. |
| 2010/0261708 A1 | 10/2010 | Cirillo et al. |
| 2010/0331304 A1 | 12/2010 | Berry et al. |
| 2011/0071127 A1 | 3/2011 | Berry et al. |
| 2011/0071196 A1 | 3/2011 | Bartolozzi et al. |
| 2011/0124696 A1 | 5/2011 | Regan et al. |
| 2011/0130431 A1 | 6/2011 | Berry et al. |
| 2011/0136869 A1 | 6/2011 | Bartolozzi et al. |
| 2011/0190256 A1 | 8/2011 | Cirillo et al. |
| 2011/0312932 A1 | 12/2011 | Bartolozzi et al. |
| 2011/0312944 A1 | 12/2011 | Bartolozzi et al. |
| 2012/0010184 A1 | 1/2012 | Bartolozzi et al. |
| 2012/0015988 A1 | 1/2012 | Hickey et al. |
| 2012/0071529 A1 | 3/2012 | Ermann et al. |
| 2012/0142666 A1 | 6/2012 | Hickey et al. |
| 2012/0142677 A1 | 6/2012 | Berry et al. |
| 2012/0316173 A1 | 12/2012 | Bartolozzi et al. |

FOREIGN PATENT DOCUMENTS

| | | |
|---|---|---|
| EP | 0628555 | 12/1994 |
| EP | 0929519 | 7/1999 |
| EP | 0970046 A1 | 1/2000 |
| EP | 1790641 A1 | 5/2007 |
| FR | 2866885 A1 | 9/2005 |
| FR | 2872813 A1 | 1/2006 |
| GB | 853799 A | 11/1960 |
| GB | 884258 A | 12/1961 |
| GB | 1237126 A | 6/1971 |
| JP | 61027905 U | 2/1986 |
| JP | 61027955 A | 2/1986 |
| JP | 61126071 A | 6/1986 |
| JP | 2003155285 | 5/2003 |
| JP | 2006504796 A | 2/2006 |
| JP | 2006525990 A | 11/2006 |
| JP | 2007502828 A | 2/2007 |
| JP | 2007530525 A | 11/2007 |
| JP | 2007530661 A | 11/2007 |
| WO | 9405628 | 3/1994 |
| WO | 9407607 | 4/1994 |
| WO | 9626925 A1 | 9/1996 |
| WO | 9712683 | 4/1997 |
| WO | 9712687 | 4/1997 |
| WO | 9720590 | 6/1997 |
| WO | 9746556 | 12/1997 |
| WO | 9808295 | 2/1998 |
| WO | 9811097 A1 | 3/1998 |
| WO | 9813340 | 4/1998 |
| WO | 9838163 A1 | 9/1998 |
| WO | 9965889 A1 | 12/1999 |
| WO | 0008015 A2 | 2/2000 |
| WO | 0100573 | 1/2001 |
| WO | 0129007 | 4/2001 |
| WO | 0164651 | 9/2001 |
| WO | 02051806 | 7/2002 |
| WO | 02088089 A1 | 7/2002 |
| WO | 02062750 | 8/2002 |
| WO | 03037274 A2 | 5/2003 |
| WO | 03055482 | 7/2003 |
| WO | 2004000807 | 12/2003 |
| WO | 2004014370 A2 | 2/2004 |
| WO | 2004014825 | 2/2004 |
| WO | 2004014902 A2 | 2/2004 |
| WO | 2004018433 | 3/2004 |
| WO | 2004026301 A1 | 4/2004 |
| WO | 2004029027 | 4/2004 |
| WO | 2004042351 A2 | 5/2004 |
| WO | 2004050643 | 6/2004 |
| WO | 2004060882 | 7/2004 |
| WO | 2004099200 A1 | 11/2004 |
| WO | 2004099205 | 11/2004 |
| WO | 2005027837 | 3/2005 |
| WO | 2005040355 | 5/2005 |
| WO | 2005044797 A1 | 5/2005 |
| WO | 2005068448 A1 | 7/2005 |
| WO | 2005077345 A1 | 8/2005 |
| WO | 2005077368 A2 | 8/2005 |
| WO | 2005077373 A2 | 8/2005 |
| WO | 2005085227 | 9/2005 |
| WO | 2006012227 | 2/2006 |
| WO | 2006030805 A1 | 3/2006 |
| WO | 2006060461 | 6/2006 |
| WO | 2006074445 A2 | 7/2006 |
| WO | 2006080040 | 8/2006 |
| WO | 2006095159 | 9/2006 |
| WO | 2006100502 | 9/2006 |
| WO | 2006117461 A2 | 11/2006 |
| WO | 2007020502 A2 | 2/2007 |
| WO | 2007054770 A2 | 5/2007 |
| WO | 2007070760 A2 | 6/2007 |
| WO | 2007080382 A1 | 7/2007 |
| WO | 2007102059 | 9/2007 |

(56) References Cited

FOREIGN PATENT DOCUMENTS

| | | | |
|---|---|---|---|
| WO | 2007118041 A1 | 10/2007 | |
| WO | 2007140385 A2 | 12/2007 | |
| WO | 2008014199 A2 | 1/2008 | |
| WO | 2008023159 A1 | 2/2008 | |
| WO | 2008039645 A1 | 4/2008 | |
| WO | 2008048914 A1 | 4/2008 | |
| WO | 2008064054 A2 | 5/2008 | |
| WO | 2008098025 A1 | 8/2008 | |
| WO | 2008104994 A2 | 9/2008 | |
| WO | 2009055357 A1 | 4/2009 | |
| WO | 2009061652 A1 | 5/2009 | |
| WO | 2009077533 A1 | 6/2009 | |
| WO | 2009105509 A1 | 8/2009 | |
| WO | 2009140089 A2 | 11/2009 | |
| WO | 2010005782 A1 | 1/2010 | |
| WO | 2010036630 A2 | 4/2010 | |
| WO | 2010036631 A2 | 4/2010 | |
| WO | 2010077836 A2 | 7/2010 | |
| WO | 2010096371 A2 | 8/2010 | |
| WO | 2010147791 A1 | 12/2010 | |
| WO | 2010147792 A2 | 12/2010 | |
| WO | 2011037795 | | 3/2011 |
| WO | WO2011035159 | * | 3/2011 |
| WO | 2011088015 A1 | 7/2011 | |
| WO | 2011109324 A1 | 9/2011 | |
| WO | 2012012307 A1 | 1/2012 | |

OTHER PUBLICATIONS

Gartst, M., et al., "Hydroformylation of bisolefinic amine derivatives catalyzed by cobalt and rhodium". Journal of Organic Chemistry, vol. 46, 1981, pp. 4433-4438.
Gavalda, et al N-Sulfonyl hydroxamate derivatatives as inhibitors of class II fructose-1, 6-diphosphate aldolase, Bioorganic & Medicinal Chemistry Letter, 2005, vol. 15, No. 24, pp. 5375-5377.
Goldschmidt,ST. et al., "Biphenyl derivatives II. Basic 4-Biphenyl Compounds". Receuil Travaux Chimiques Des Pays-Bas, vol. 69, 1950, pp. 1109-1117.
Grothe, V. W. et al. "Effect of Potassium Sulfhydrate etc. on Chloroacetylanilides". Archiv der Pharmazie (Weinheim), vol. 238, 1980, p. 600-614.
Hadjipavlou-Litina, D. et al., "Thiazolyl-N-Substituted Amides: A group of effective anti-inflammatory agents with potential for local anesthetic properties. Synthesis, Biological Evaluation, and a QSAR Approval." Drug Development Research, Vo. 48, 1999, p. 53-60-.
Hanus, L. et al., "HU-308: A specific agonist for CB2, a peripheral cannabinoid receptor", PNAS, 1999, vol. 96, No. 25, p. 14228.
Hauske, J. et al., "Design and Synthesis of Novel FKBP Inhibitors." Journal of Medicinal Chemistry, 1992, vol. 35, No. 23, pp. 4284-4296.
Herndon, J. L. et al., "Ketanserin analogues. Structure-affinity relationships for 5-HT2 and 5-HT1c serotoninin receptor binding". J. Med. Chem, 1992, vol. 35, No. 26, pp. 4903-4910.
Huang, X. et al., "A Novel Synthesis of Sulfones via the O.O-Diethylphosphorotellurite Ion-assisted Coupling of Arenesulfonyl Chlorides with Active Halides". Synthetic Communications, 20(15), 2291-2291-2295 (1990).
Ibrahim, M. M. et al., "Activation of CB2 cannabinoid receptors by AM1241 inhibits experimental neuropathic pain: Pain inhibition by receptors not present in the CNS", PNAS, 2003, vol. 100, No. 18, p. 10529.
Iddon, B. et al., "Condensed thiophen ring systems. Part SVII. A new synthesis of 10H-indeno[1,2-b][1] benzothiophen". Journal of the Chemical Society. Perkin Transactions 1, Chemical Socieity. Letchworth, GB. vol. 21, Jan. 1, 1974, pp. 2505-2508. ISSN: 0300-922X, p. 2506; compound 8.
Iddon, B. et al., "Polyhalogenoaromatic Compounds. Part 42. C N.m.r. Spectra of Polyhalogeno-pyridines and -pyrimidines". XP009094360, Ramage Laboratories, Dept of Chemistry and Applied Chemistry, University of Salford, Salford M5 4WT, Journal of the Chemical Society, Perkin Transactions 1, 1980, p. 1370.
Igarashi, J. et al., "Improved synthesis of quinine alkaloids with the Teoc protective group". Tetrahedron letters, Elsevier, Amsterdam, vol. 46, No. 37, 2005, pp. 6381-6384.
International Search Report and Written Opinion for PCT/US2011/044309 mailed Sep. 1, 2011.
Ishii, K. et al., "Smiles Rearrangement of 2-(1-Methyl-1H-tetrazol-5-ylthio)acetamides and their Sulfonyl Derivatives". XP009094359, Chem. Pharm. Bull. 39(12) 3331-3334 (1991).
Iwakubo, M. et al., "Design and synthesis of Rho kinase inhibitors (II)". Biorganic and Medicinal Chemistry, Vo. 15, No. 1, Nov. 15, 2006, p. 350-364.
Johansen et al., AMPA Receptor Agonists: Resolution, Configurational Assignment, and Pharmacology of (+)-(S)-and (−)-(R)-2-Amino-3-(3-Hydroxy-5-(2-Pyridyl) Isoxazol-4-yl)Propionic Acid (1-Py-AMPA); Chirality, New York, 1997, vol. 9, No. 3, pp. 274-280.
Kano, S. et al., "Formation of Some Heterocycles through Ring Transformation of 1-Arylaxetidin-2-Ones." Heterocycles, vol. 8, No. 1, Dec. 30, 1977, p. 411-416.
Katoh, A., et al., "Synthesis of 6-(Bromoacetyl)Amino-2,3-Dimorpholino-Quinoxaline and Application to a new Fluorescence Derivatization Reagent of Fatty Acids for the High-Performance Liquid Chromatographic Analysis", Heterocycles, 1999, vol. 50, No. 1, p. 299.
Katz, L., et al., "Hydrazine Derivatives. II. Ortho-Mercapto-Pyridinecarbohydrazides", Contribution from Schenley Laboratories, Inc., 1953, p. 711.
Klein, T. W., et al., "The Cannabinoid system and immune modulation", J. Leukocyte Biology, 2003, vol. 74, p. 486.
Kolehmainen, E. et al., "a-Phenylsulfonyl-N-arylacetamides (a-phenylsulfonylacetanilides): H, C and N NMR spectral characterization". XP002465784, Magnetic Resonance in Chemistry, 2000, 38: 384-385.
Krutosikova, A. et al., "Furan derivatives. LV. Preparation of 5-aryl-2-furfuryl phenyl and 5-aryl-2-furfuryl 4-tolyl sulfones". Chemick Zvesti—Chemical Papers, Veda Bratislava, SK. vol. 28, Jan. 1, 1974, pp. 414-417, ISSN: 0366-6352, p. 414, compounds I-IX.
Kulkarni, S.S. et al., "Design and synthesis of noncompetitive metabotropic glutamate receptor subtype 5 antagonists." Bioorganic and Medicinal Chemistry Letters, Vo. 16, No. 13, Jul. 1, 2006, p. 3371-3375.
Lambeng, N. et al., "Discovery of a Novel Piperidinyl-Sulfonyl Benzoic Ester, Active as CB1 Agonist" POSTER. 231st ACS National Meeting, Atlanta, GA. Mar. 26-30, 2006.
LeBerre, A. et al., No. 150—Alpha-sulfocarboxylic acids and derivatives. V.-Acyclic sulfamoyl carboxyesters and carboxamides. 1,2-Thiazetidine 3-one 1,1-dioxides. National Conservatory of Skills and Trades, Laborator of Industrial Chemistry. Manuscript received Seotenber 17, 1974, p. 807-811.
Lesser, R. et al. "Homo-?-oxythionaphthene (4-Ketoisothiochromane". Charlottenburg, Industrial Chemistry Laboratory of the Institute of Technology, 1923, pp. 1642-1648.
Li, S. et al., "The Synthesis and Preliminary Activity Assay In Vitro of Peptide-like Derivatives as APN Inhibitors." Archives of Pharmacal Research, 2008, vol. 31, No. 10, pp. 1231-1239.
Lutz, R. E. et al., "Antimalarials. Some piperazine derivatives". Journal of Organic Chemistry, vol. 12, 1947, pp. 771-775.
Mahmoud, A. M. et al., "Synthesis and Biological Activity of Some new 2-(N-Substituted Carboxamidomethyl Thio)-Naphth[1,2-d]Oxazoles-Part V". XP002068972, J. Indian Chem. Soc., vol. LIX, May 1982, pp. 675-677.
Malan Jr., T. P., et al., "CB2 cannabinoid receptor-mediated peripheral antinociception", Pain, 2001, vol. 93, p. 239.
Markley, L. D., et al., "Antipicornavirus activity of substituted Phenoxybenzenes and Phenoxypyridines", J. Med. Chem., 1986, vol. 29, p. 427.
Marx, I. E. et al., "Discovery of a-amidosulfones as potent and selective agonists of CB2: Synthesis, SAR, and pharmacokinetic properties". Bioorganic and Medicinal Chemistry Letters, 2009, p. 31-35.
Marx, I. E. et al., "Discovery of a-amidosulfones as potent and selective agonists of CB2: Synthesis, SAR, and pharmacokinetic properties". Bioorganic and Medicinal Chemistry Letters, 2009, p. 31-35. In press, accepted manuscript.

(56) References Cited

OTHER PUBLICATIONS

Messinger, P., "Sulfones via Mannich bases" Archiv der Pharmazie, 1973, vol. 306, No. 8, pp. 603-610, ISSN: 0365-6233. p. 607, compounds 28A-29C.
Miroshnikova, O.V. et al., "Structure-activity relationships in the series of eremomycin carboxamides". Journal of Antibiotics, vol. 53, No. 3, 2000, pp. 286-293.
Miyano, S, et al., "Kinetic Resolution of Racemic b-Hydroxy Amines by Enantioselective N-Oxide formation". Journal of Organic Chemistry, 1985, vol. 50, pp. 4350-4360.
Mohler, et al., "Nonsteroidal tissue selective androgen receptor modulators: a promising class of clinical candidates" University of Tennessee Health Science Center, Expert Opinion of Therapeutic Patents; Nov. 2005, vol. 15, No. 11, pp. 1565-1585.
Nackley, A. G., et al., "Selective Activation of Cannabinoid CB2 Receptors Suppresses Spinal FOS Protein Expression and Pain Behavior in a rat Model of Inflammation", Neuroscience, vol. 119, 2003, p. 747.
Office Action from the EPO for 09-0388 dated Mar. 22, 2010.
Office Action mailed Jan. 13, 2012 for U.S. Appl. No. 12/882,328, filed Sep. 15, 2010. Inventor: Alessandra Bartolozzi.
Office Action mailed Jan. 27, 2012 for U.S. Appl. No. 12/741,260, filed Jun. 17, 2010. Inventor: Angela Berry.
Pollard, C. B. et al., "Some amides of piperazines". Journal of American Chemical Society, vol. 75, 1953, p. 491.
Revesz, L. et al., "Novel CCR1 antagonists with oral activity in the mouse collagen induced arthritis". Bioorganic and Medicinal Chemistry Letters, vol. 15, 2005, pp. 5160-5164.
Sakuraba, S, et al., "Efficient asymmetric hydrogenation of a-amino ketone derivatives. A highly enantioselective synthesis of phenylephrine, levamisole, carnitine and propranolol". Chemical and Pharmaceutical Bulletin, Pharm. Society of Japan, 1995, vol. 43, No. 5, pp. 738-747.
Schaefer, H. et al. "On the Synthesis of 4-aminoquinolines and -quinolinones-(2) from Anthranilonitrile" Chemistry Department of the Technical University of Dresden, Journal for Practical Chemistry, vol. 321, No. 4, 1979, pp. 695-698.
Seidel M. C. et al., "Heterocyclic Rearrangements. XII. The Formation of a Formylbenzofurazan oxide from a nitroanthranil". Journal of Organic Chemistry, vol. 35, No. 5, May 1970, p. 1662-1664.
Sharkey, K. A. et al., "CB2 cannabinoid receptors: new vistas", The first International Conference devoted to studies of the CB2 cannabinoid receptor. Banff, Alberta, Canada, May 31-Jun. 3, 2007.
Sheehan, J.C. et al, The Synthesis and Reactions of Some Substituted Beta-Lactams, 1951, Journal of the American Chemical Society, 73, 1761-1765.
Abstract in English for JP 61-027905, Feb. 7, 1986, and WO199626925, Sep. 1996, Derwent Abstract.
Abstract in English for JP 61-027955, Feb. 7, 1986, Derwent.
Abstract in English for JP2003155285, May 27, 2003, Inventor: T. Makoto.
Anisimov, A. V. et al., "Synthesis of Sulfonyl and Sulfenyl Derivatives of Pyridine and 1,2,4-Triazole". Russian Journal of Organic Chemistry, 2006, vol. 42, No. 6, pp. 918-921.
Aranapakam, V. et al., "Synthesis and Structure—Activity Relationship of a-Sulfonylhydroxamic Acids as Novel, Orally Active Matrix Metalloproteinase Inhibitors for the treatment of Osteoarthritis", J. Med. Chem., 2003, vol. 46, p. 2361.
Aranapakam, V. et al., "Synthesis and Structure—Activity relationship of n-Substituted 4-Arylsulfonylpiperidine-4-hydroxamic Acids as Novel, Orally Active matrix Metalloproteinase Inhibitors for the treatment of Osteoarthritis", J. Med. Chem., 2003, vol. 46, p. 2376.
Aranapakam, V., et al., "Synthesis and Structure—Activity relationships of 4-alkynyloxy Phenyl Sulfanyl, Sulfinyl, and Sulfonyl Alkyl Hydroxamates as Tumor Necrosis Factor-a Converting Enzyme and Matrix Metalloproteinase Inhibitors", J. Med. Chem., 2004, vol. 47, p. 6255.
Arevalo-Martin, A. et al., "Therapeutic Action of Cannabinoids in a Murine model of Multiple Sclerosis", J. of Neuroscience, 2003, vol. 23, No. 7, p. 2511.

Atwell, G. J. et al., "Relationships between Structure and Kinetics of Cyclization of 2-Aminoaryl Amides: Potential Prodrugs of Cyclization-Activitated Aromatic Mustards", XP-002465787, J. Med. Chem, 1994, 37, 371-380.
Audouze, K. et al., "New series of morpholine and 1,4-oxazepane derivatives as dopamine D4 receptor ligands. Synthesis and 3D-QSAR model." J. Med. Chem, vol. 47, No. 12, pp. 3089-3104, 2003.
Bair, K. W. et al., "(1-pyrenylmethyl)amino alcohols, a new class of antitumor DNA intercalators. Discovery and intial amine side chain structure-activity studies". Jornal of Medicinal Chemistry, vol. 33, 1990, pp. 2385-2393.
Baker, D. et al., "Cannabinoids control spasticity and tremor in a multiple sclerosis model", Nature, 2000, vol. 404, p. 84.
Baltzly, R. et al., "The preparation of N-mono-substituted and unsymmetrically disubstituted piperzines". Journal of American Chemical Society, vol. 66, 1944, pp. 263-265.
Baltzly,R. et al., "Unsymmetrically substituted piperazines. V. Piperazine ureas". The Journal of the American Chemical Society, vol. 76, 1954, pp. 1165-1166.
Balzarini, J. et al., "Antiretroviral activity of semisynthetic derivatives of glycopeptide antibiotics". J. Med. Chem., 2003, vol. 46, No. 13, pp. 2755-2764.
Beilstein Database—Beilstein Registry No. 1084348. CAS Registry No. 6125-38-8. Beilstein Institute for Organic Chemistry. 1966, Abstract.
Beilstein Database—Beilstein Registry No. 1179643. CAS Registry No. 54890-73-2. Beilstein Institute for Organic Chemistry. 1974, Abstract.
Beilstein Database—Beilstein Registry No. 5396840. CAS Registry No. 54890-82-3. Beilstein Institute for Organic Chemistry. 1974, Abstract.
Beilstein Database—Beilstein Registry No. 5398283. CAS Registry No. 68558-02-01. Beilstein Institute for Organic Chemistry. 1978, Abstract.
Beilstein Database—Beilstein Registry No. 857451. CAS Registry No. 37901-58-9. Beilstein Institute for Organic Chemistry. 1972, Abstract.
Binisti, C. et al., "Structure-Activity relationships in platelet-activating factor (PAF). 11-From PAF-antagonism to phospholipase A2 inhibition: syntheses and structure-activity relationships in 1-arylsulfamido-2-alkylpiperazines", Eur. J. Med. Chem., 2001, vol. 36, p. 809.
Brown, P. J. et al., "A Ureido-Thioisobutyric Acid (GW9578) Is a Subtype-Selective PPARa Agonist with Potent Lipid-Lowering Activity", J. Med. Chem. 1999, vol. 42, p. 3785.
Bruche, L. et al., "1,3-Dipolar Cycloadditions of 3,5-Dichloro-2,4,6-trimethylbenzonitrile Oxide to Phenylsulfonylallenes". Journal of Organic Chemistry, vol. 50, 1985, pp. 3206-3208, p. 3206, compounds 5a and 5b.
Buckley, N. E. et al., "Immunomodulation by cannabinoids is absent in mice deficient for the cannabinoid CB2 receptor", Eur. J. Pharmacology, 2000, vol. 396, p. 141.
Caplus—1990:497413, Zara-Kaczian, Acta Chimica Hungarica, 1989.
Caplus—RN 112298-90-5 (Tommasi), retrieved from Caplus on Jan. 2, 2009.
Caplus—RN 262371-16-4 (Organ), retrieved from Caplus on Jan. 2, 2009.
Caplus—RN 57992-82-2 (Babayan), retrieved from Caplus on Jan. 2, 2009.
Carenzi, A, et al., "New Isoxazole Derivatives Provided with Antihypertensive Activity". Arzneimittel-Forschung, vol. 39, No. 6, 1989, p. 624-646.
Cartwright, D., et al., "Abnormal Nucleophillic substitution in 3-trichloromethylpyridine, its N-oxide and 3,5-Bis (trichloromethyl)pyridine". Tetrahedron, Elsevier Science Publishers, Amsterdam, vol. 51, No. 47, 1995, pp. 12791-12796.
Catalano, A. et al., "Constrained analogues of tocainide as potent skeletal muscle sodium channel blockers toward the development of antimyotonic agents". European Journal of Medicinal Chemistry, vol. 43, No. 11, 2008, p. 2535-2540.

(56) References Cited

OTHER PUBLICATIONS

Chang, M. Y. et al, "Reaction of different a-sulfonyl acetamides with methyl acrylate". Tetrahedron 58 (2002) p. 5075-5080.

Chem Abstract—Accession No. 126:89390, Abstract of JP8311026, Kumaiai Chemical Industry Co., Nov. 26, 1996.

ChemAbstract: 246020-62-2 registry copyright ACS on STN, entered 1999. Chemcats.

ChemAbstracts, Ukraine. Order Numbers: T6110295, T5962700, T5962703 abstract and "Enamine Screening Library", Jan. 1, 2009, Enamine, 23 Alexandra Matrosova St., 01103 Kiev, Ukraine.

ChemAbstracts: 693218-49-4 and 402562-90-7. 2004.

Chen, D. et al., "Preparation, properties, and synthetic potentials of novel boronates in a flourous version (flourous boronates)". Organic Letters, vol. 4. No. 6, 2002, pp. 1003-1005.

Clark, N. G. et al., "The Fungicidal Activity of Substituted Acetanilides and Related Compounds". Biochemical Journal, 1953, vol. 55, p. 839-851.

Cockcroft, X. L. et al., "Phthalazinones 2: optimization and synthesis of novel potent inhibitors of ply(ADP-ribose) polymerase". Bioorganic & Medicinal Chemistry Letters, 16, 2006, pp. 1040-1044.

Dav, Jr., R. A. et al., "Polarography of phenyl 2-thienyl and 2,2'-dithienyl ketones". 1953.

El-Hawash, S. A. M., et al., "Synthesis and invitro-Anticancer and Antimicrobial Evaluation of Some Novel Quinoxalines Derived from 3-Phenylquinoxaline-2(1H)-thione". Arch. Pharm. Chem. Life Sci, 2006, 339, p. 437-447.

EP Office Action for Case 09-0388 dated Mar. 22, 2010.

Ermann, M. et al., "Arylsulfonamide CB2 receptor agonists: SAR and optimization of CB2 selectivity", Bioorganic and Medicinal Chemistry Letters 18 (2008) 1725-1729.

Ermann, M., et al., Moscone Conv.Ctr. "Discovery of a novel class of CB2 receptor agonists". Presented at the Cambridge Healthcare Institute's 15th International Molecular Medicine Tri-Conference, Moscone Convention Center, San Francisco, CA, USA. Mar. 25-28, 2008.

Ermann, M., et al., UK, "Discovery of a novel class of CB2 receptor agonists". Presented at the 14th SCI-RSC Medicinal Chemistry Symposium, Churchill College, Cambridge, UK, Sep. 23-26, 2007.

Evans, W. J. et al., "A Rearrangement of Carbamyl-sulphones and -sulphides". Journal of the Chemical Society, 1936, p. 329-331.

Faucher, A. M. et al., "Discovery of Small-Molecule Inhibitors of the ATPase Activity of Human Papillomavirus E1 Helicase", J. Med. Chem., 2004, vol. 47, p. 18.

Field, L. et al., "Grignard Reagents of Sulfones. IV. Reactions with Nitriles, Esters and an Isocyanate". Journal of American Society, vol. 78, 1956, p. 4389-4394.

Field, L., et al., "Methyl p-Tolyl Sulfone", Organic Syntheses, Coll. vol. 4, p. 674, 1963; vol. 38, p. 62, (1958).

Fringuelli, F. et al., "Solvent-Free Al(OTi)3-catalyzed aminolysis of 1,2-Epoxides by 2-picolylamine: a key step in the synthesis of ionic liquids". Journal of Organic Chemistry, vol. 69, 2004, pp. 7745-7747.

Sisko, J. et al., "An investigation of imidazole and oxazole synthesis using aryl-substituted TosMIC reagents". The Journal of Organic Chemistry, vol. 65, No. 5, Mar. 10, 2000, pp. 1516-1624, ISSN: 022-3263, p. 1523, table 5, compound 69.

Smith, S. R., et al., "The anti-inflammatory activities of cannabinoid receptor ligands in mouse peritonitis models", Eur. J. Pharmacology, 2001, vol. 432, p. 107.

Stalberg, O. et al. "Capillary Electrophoretic Separation of Basic Drugs Using Surface-Modified C8 Capillaries and Derivatized Cyclodextrins as Structural/Chiral Selectors." Chromatographia, 1995, vol. 40, No. 11/12, pp. 697-704.

STN results for Dorme et al., Bulletin de la Societe Chimique de France; 1959; No. 9; pp. 2582-2588.

Strating, J., et al. "Nucleophilic Additions to Bis-Tertiobutyl Sulfonyl Acetylene (Properties of the sulfonyl group XLIV 1)". University of Groningue, Organic Chemistry Laboratory, 1954, pp. 709-716.

Swanson, D. M. et al., "Identification and biological evaluation of 4-*(3-trifluoremethylpyridin-2-yl)piperzine-1-carboxylic acid (5-trifluoremethylpyridin-2-yl)amide, a high affinity TRPV1 (VR1) vanilloid receptor antagonist". Journal Med. Chem, 2005, 48, pp. 1857-1872.

Tegley, et al., "Discovery of Novel Hydroxy-Thiazoles as HIF-alpha Prolyl Hydroxylase Inhibitors: SAR, Synthesis, and Modeling Evaluation," Bioorganic & Medicinal Chemistry Letters, Pergamon, Elsevier Science, GB, vol. 18, No. 14, 2008, pp. 3925-3928.

Todorova, T. R., et al "Ring-enlargement and ring-opening reactions of 1,2-thiazetidin-3-one 1,1,-dioxides with ammonia and primary amines as nucleophiles". Helvetica Chimica Acta, vol. 82, 1999, pp. 354.

Troeger, J. et al., "Regarding sulfonated Butyric Acids". From the Laboratory for Pharmaceutical and Synthetic Chemistry of the Braunschweig Institute of Technology.1991, 40, 506.

Troeger, J. and Uhde, R., "Ueber sulfonirte buttersauren", J. Prakt. Chem., 1899, 1991, vol. 59, p. 320.

Tweit, R. C., et al., "Synthesis of Antimicrobial Nitroimidazolyl 2-Sulfides, -Sulfoxides, and -Sulfones". Dept. of Chemical and Biological Research, Searle Laboratories, Chicago, IL, USA, Mar. 29, 1973, pp. 1161-1169.

U.S. Appl. No. 13/022,866, filed Feb. 8, 2011, Inventor: Angela Berry.

U.S. Appl. No. 13/037,422, filed Mar. 1, 2011, Inventor: Monika Ermann.

Ueda, Y., et al., "Involvement of cannabinoid CB2 receptor-mediated response and efficacy of cannabinoid CB2 receptor inverse agonist, JTE-907, in cutaneous inflammation in mice", Eur. J. Pharmacology, 2005, vol. 520, p. 164.

Van Sickle, M. D., et al., "Identification and Functional Characterization of Brainstem Cannabinoid CB2 receptors", Science, 2005, vol. 310, p. 329.

Venkov, A.P. et al., "A new synthesis of 1,2,3,40tetrahydro-2-methyl-4-phenylisoquinolines". Dept of Chemistry, University of Plovdiv, Bulgaria, pp. 253-255, Mar. 1990.

Vogtle, M. M. et al., "An efficient protocol for the solid-phase synthesis of malondiamides". Molecules, 2005, 10, pp. 1438-1445. XP002481324.

Walker, G.N. et al., "Synthesis of varied heterocyclic and substituted aryl alkyl secondary amines, related Schiff bases, and amides". Journal of Medicinal Chemistry, vol. 9, 1966, pp. 624-630.

Wang, Y. et al., "Rapid and efficient synthesis of 1,2,4-oxadiazoles utilizing polymer-supported reagents under microwave heating". Organic Letters, vol. 7, No. 5, Mar. 3, 2005, pp. 925-928, ISSN: 1523-7060, p. 927, compounds 14,15.

Watson, R. J., et al., "An enantioselective synthesis of sulphonamide hydroxamic acids as matrix metalloproteinase inhibitors", Pergamon, Tetrahedron Letters 43 (2002) 683-685.

White, J.D. et al., "Conversion of Carbamates to Amidosulphones and Amides. Synthesis of the [ 14 C]-Labeled Antiobestity Agent Ro23-7637", Organice Letters, vol. 4. No. 10, Apr. 17, 2002, pp. 1803-1806.

Yang, G. et al., "Synthesis and Bioactivity of Novel Triazolo [1,5-a]Pyrimidine Derivatives[3]". XP002465786, Heteroatom Chemisry, vol. 12, No. 6, 2001, p. 491-496.

Yokoyama, M. et al., "A regioselective synthesis of 3 5 disubstituted isoxazoles". Journal of the Chemical Society Perkin Transactions I, No. 1, 1986, pp. 67-72, ISSN: 0300-922X, pp. 68,69, compounds 6A, 14A.

Yordanova, K. et al. "New method for the synthesis of 2,4-disubstituted morpho- lines". Chemical Abstracts, vol. 97, No. 17, Oct. 25, 1982, Columbus, Ohio, USA Chemical Abstracts, vol. 97, No. 17, Oct. 25, 1982, Columbus, Ohio, vol. 115, No. 7, pp. 2635-2642.

Zhang, B. and Breslow, R., "Ester Hydrolysis by a Catalytic Cyclodextrin Dimer Enzyme Mimic with a Metallobipyridyl Linking Group", J. Am. Chem. Soc., 1997, vol. 119, p. 1676.

Zimmer, A. et al., "Increased mortality, Hypoactivity, and hypoalgesia in cannabinoid CB1 receptor knockout mice", Proc. Natl. Acad. Sci. USA, 1999, vol. 96, p. 5780.

Zindell, R. et al., "Discovery of a novel class of CB2 agonists". General Poster Session. The 235th ACS National Meeting, New Orleans, LA, USA. Apr. 6-10, 2008.

\* cited by examiner

SULFONYL COMPOUNDS WHICH MODULATE THE CB2 RECEPTOR

APPLICATION DATA

This application claims benefit to U.S. provisional application Ser. No. 61/366,660 filed Jul. 22, 2010.

BACKGROUND OF THE INVENTION

1. Technical Field

The present invention relates to novel compounds which modulate the CB2 receptor and their use as medicaments.

2. Background Information

Cannabinoids are a group of about 60 distinct compounds found in *Cannabis sativa* (also know as marijuana) with cannabinol, cannabidiol and $\Delta^9$-tetrahydrocannabinol (THC) being the most representative molecules. The therapeutic usage of *Cannabis* can be dated back to ancient dynasties of China and includes applications for various illnesses ranging from lack of appetite, emesis, cramps, menstrual pain, spasticity to rheumatism. The long history of *Cannabis* use has led to the development of several pharmaceutical drugs. For example, Marinol and Cesamet which are based on THC and its analogous nabilone, respectively, are used as anti-emetic and appetite stimulant. Despite of the clinical benefits, the therapeutic usage of cannabis is limited by its psychoactive effects including hallucination, addiction and dependence. Mechoulam R, ed. *Cannabinoids as Therapeutic Agents*, Boca Raton, Fla.; CRC Press, 1986 provides a review of the medicinal use of cannabis.

The physiological effects of cannabinoids are mediated by at least two G-protein coupled receptors, CB1 and CB2. Autoradiographic studies have demonstrated that CB1 receptors are expressed primarily in the central nervous system, specifically in the cerebral cortex, hippocampus, basal ganglia and cerebellum. They are also found to a lesser degree in the reproductive system and other peripheral tissues including that of the immune system. CB1 receptors regulate the release of neurotransmitters from the pre-synaptic neurons and are believed to mediate most of the euphoric and other central nervous system effects of cannabis, such as THC-induced ring-catalepsy, hypomobility, and hypothermia, which were found to be completely absent in mice with a deletion of the CB1 gene (Zimmer et al., Increased mortality, hypoactivity, and hypoalgesia in cannabinoid CB1 receptor knockout mice. Proc Natl Acad Sci USA. (1999) 96:5780-5785.)

CB2 receptors are almost exclusively found in the immune system, with the greatest density in the spleen. It is estimated that the expression level of CB2 in the immune cells is about 10 to 100 times higher than CB1. Within the immune system, CB2 is found in various cell types, including B cells, NK cells, monocytes, microglial cells, neutrophils, T cells, dentritic cells and mast cells, suggesting that a wide range of immune functions can be regulated through CB2 modulators (Klein et al., The cannabinoid system and immune system. J Leukoc Biol (2003) 74:486-496). This is supported by the finding that the immunomodulatory effect of THC is absent in CB2 deficient mice (Bicklet et al., Immunomodulation by cannabinoid is absent in mice deficient for the cannabinoid CB2 receptor. Eur J Pharmacol (2000) 396:141-149). CB2 selective ligands have been developed and tested for their effects in various inflammatory settings. For example, in animal models of inflammation, CB2 selective agonists, inverse agonists and antagonists have been shown to be effective in suppressing inflammation (Hanus et al., HU-308: a specific agonist for CB(2), a peripheral cannabinoid receptor. Proc Natl Acad Sci USA. (1999) 96:14228-14233, Ueda et al., Involvement of cannabinoid CB(2) receptor-mediated response and efficacy of cannabinoid CB(2) receptor inverse agonist, JTE-907, in cutaneous inflammation in mice. Eur J Pharmacol. (2005) 520:164-171 and Smith et al., The anti-inflammatory activities of cannabinoid receptor ligands in mouse peritonitis models Eur J Pharmacol. (2001) 432:107-119.). Furthermore, CB2 selective agonists inhibit disease severity and spasticity in animal models for multiple sclerosis (Baker et al., Cannabinoids control spasticity and tremor in a multiple sclerosis model. Nature (2000) 404:84-87. Arevalo-Martin et al., Therapeutic action of cannabinoids in a murine model of multiple sclerosis J Neurosci. (2003) 23:2511-2516.). Taken together, these results support the notion that CB2 receptor modulators can be employed for the treatment of medical conditions having an inflammatory component.

In addition to inflammation, CB2 agonists have been shown to inhibit pain and emesis. For instance, CB2 selective agonists blunt the pain response induced by thermal or other stimuli (Malan et al., CB2 cannabinoid receptor-mediated peripheral antinociception. Pain. (2001) 93:239-45 and Nackley et al., Selective activation of cannabinoid CB(2) receptors suppresses spinal fos protein expression and pain behavior in a rat model of inflammation. Neuroscience (2003) 119:747-57.) CB2 activation has also been demonstrated to inhibit neuropathic pain response (Ibrahim et al., Activation of CB2 cannabinoid receptors by AM1241 inhibits experimental neuropathic pain: pain inhibition by receptors not present in the CNS. Proc Natl Acad Sci USA. (2003) 100: 10529-33.) Finally, in contrast to the earlier data which did not find CB2 in the brain, a recent article demonstrated the expression of CB2 in the brain, at about 1.5% of the level in the spleen. CB2 activation is shown by this article to be responsible for the anti-emetic effect of endocannabinoid (Van Sickle et al., Identification and functional characterization of brainstem cannabinoid CB2 receptors. Science. 2005 310:329-332.) The foregoing results confirm that CB2 agonists can be used for the treatment of inflammatory and neuropathic pain as well as emesis.

WO2008014199 and WO2008039645 discuss the CB2 receptor and the therapeutic uses of the sulfone derivatives, having CB2 agonist activity, disclosed therein.

BRIEF SUMMARY OF THE INVENTION

The present invention provides novel compounds which bind to and modulate the CB2 receptor. The invention also provides methods and pharmaceutical compositions for treating inflammation by way of the administration of therapeutic amounts of the compounds of the invention. Lastly, the invention provides a method and pharmaceutical compositions for treating pain by way of the administration of therapeutic amounts of the compounds of the invention.

DETAILED DESCRIPTION OF THE INVENTION

In the broadest generic embodiment 1, the invention provides compounds of the formula

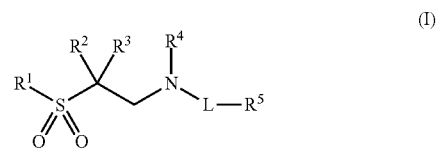

(I)

wherein:

$R^1$ is $C_{1-10}$ alkyl, $C_{3-10}$ cycloalkyl, 3-10 membered saturated heterocyclic ring, $C_{1-5}$ alkyl-heterocyclic ring, 5-10 membered mono or bicyclic heteroaryl ring, $C_{1-5}$ alkyl-heteroaryl ring, 5-10 membered mono or bicyclic aryl ring or $C_{1-5}$ alkyl-aryl ring, wherein each $R^1$ is optionally independently substituted with 1-3 substituents chosen from $C_{1-4}$ alkyl group, $C_{3-10}$ cycloalkyl, $C_{1-4}$ alkoxy, $C_{1-4}$ alkylsulfonyl, $C_{1-4}$ acyl, oxo, phenyl, cyano, hydroxyl and halogen;

$R^2$ and $R^3$ are $C_{1-4}$ alkyl or hydrogen with the proviso that both $R^2$ and $R^3$ cannot be hydrogen; or $R^2$ and $R^3$ together with the carbon atom to which they are attached form a 3- to 6-membered cycloalkyl ring or heterocyclic ring;

$R^4$ is hydrogen or methyl;

$R^5$ is 5-10 membered mono or bicyclic heteroaryl ring optionally independently substituted with 1-3 substituents chosen from $C_{1-4}$ alkyl group, cyano, —$C_{1-8}$ branched or unbranched alkyl —O—$R^6$, $C_{3-8}$-cycloalkyl-O—$R^6$, —$C_{1-3}$ branched or unbranched alkyl —$R^7$ and aryl-$R^8$ each $R^6$ is independently hydrogen, $C_{1-4}$ alkyl, —$C_{1-4}$ alkyl-O $C_{1-4}$ alkyl, or —$C_{1-4}$ alkyl-OH;

$R^7$ is a 5-6 membered heteroaryl ring;

$R^8$ is hydroxyl, $C_{1-6}$ alkoxy, $C_{1-4}$ alkylsulfonyl, cyano, halogen or $C_{1-4}$ alkyl L is a bond, —C(O)—, —C(O)—NH— or —$SO_2$—;

wherein any carbon atom on the formula (I) or any R substituent listed above is optionally partially or fully halogenated where possible;

or a pharmaceutically acceptable salt thereof.

In another embodiment 2, the invention provides compounds of the formula (I) according to the preceding generic embodiment described above, and wherein $R^1$ is $C_{1-6}$ alkyl, phenyl, cyclopropyl, cyclobutyl, cyclopentyl, cyclohexyl, cycloheptyl, cyclooctyl, —$CH_2$-cyclopropyl, —$CH_2$-cyclobutyl, —$CH_2$—$CH_2$-cyclopropyl, —$CH_2$—$CH_2$-cyclobutyl, tetrahydrofuranyl, tetrahydropyranyl, azetidinyl, piperidinyl, thiomorpholinyl, 1,1-dioxo-$1\lambda^6$-thiomorpholinyl, morpholinyl, pyrrolidinyl, piperazinyl, benzyl, —$CH_2$-tetrahydrofuranyl, —$CH_2$-tetrahydropyranyl, —$CH_2$—$CH_2$-tetrahydrofuranyl, —$CH_2$—$CH_2$-tetrahydropyranyl, benzoxazolyl, benzothiazolyl, benzimidazolyl, oxazolyl, isoxazolyl, thiazolyl, pyrazolyl, pyrrolyl, imidazolyl, thienyl, thiadiazolyl, pyridinyl, pyrimidinyl, pyridazinyl, pyrazinyl, quinolinyl, isoquinolinyl, indolyl, benzofuranyl or benzopyranyl, wherein each $R^1$ is optionally independently substituted with 1-3 substituents chosen from $C_{1-4}$ alkyl group, $C_{1-4}$ alkoxy, $C_{1-4}$ alkylsulfonyl, $C_{1-4}$ acyl, oxo, phenyl, cyano, hydroxyl and halogen;

$R^2$ and $R^3$ are independently methyl, ethyl, n-propyl, isopropyl, t-Butylor hydrogen with the proviso that both $R^2$ and $R^3$ cannot be hydrogen; or $R^2$ and $R^3$ together with the carbon to which they are attached form a cyclopropyl, cyclobutyl, or cyclopentyl ring;

$R^4$ is hydrogen or methyl;

$R^5$ is isoxazolyl, thiazolyl, pyrazolyl, pyrrolyl, imidazolyl, thienyl, thiadiazolyl, pyridinyl, pyrimidinyl, pyridazinyl, pyrazinyl, triazinyl, tetrazolyl, oxazolyl, oxadiazolyl or furanyl, wherein each $R^5$ is optionally independently substituted with 1-3 substituents chosen from $C_{1-4}$ alkyl group, cyano, —$C_{1-8}$ branched or unbranched alkyl —O—$R^6$, -cycloalkyl-O—$R^6$, —$C_{1-3}$ branched, or unbranched alkyl —$R^7$ and phenyl-$R^8$;

each $R^6$ is independently hydrogen or $C_{1-4}$ alkyl, —$C_{1-4}$ alkyl-O$C_{1-4}$ alkyl, or —$C_{1-4}$ alkyl-OH;

$R^7$ is pyrazolyl, isoxazolyl, oxazolyl, oxadiazolyl or thiazolyl;

$R^8$ is hydroxyl, $C_{1-3}$ alkoxy, $C_{1-4}$ alkylsulfonyl, cyano, halogen or $C_{1-4}$ alkyl or a pharmaceutically acceptable salt thereof.

In another embodiment 3, the invention provides compounds of the formula (I) according to any of the preceding embodiments, and wherein $R^1$ is $C_{1-6}$ alkyl, phenyl, tetrahydropyranyl or —$CH_2$-tetrahydropyranyl wherein each $R^1$ is optionally independently substituted with 1-3 substituents chosen from $C_{1-4}$ alkyl group and halogen;

or a pharmaceutically acceptable salt thereof.

In another embodiment 4, the invention provides compounds of the formula (I) according to any of the preceding embodiments, and wherein $R^2$ and $R^3$ are methyl or a pharmaceutically acceptable salt thereof.

In another embodiment 5, the invention provides compounds of the formula (I) according to any of the preceding embodiments described above, and wherein $R^4$ is hydrogen;

$R^5$ is isoxazolyl, pyrazolyl or pyridinyl, wherein each $R^5$ is optionally independently substituted with 1-3 substituents chosen from $C_{1-4}$ alkyl group, hydroxyl and halogen;

or a pharmaceutically acceptable salt thereof.

In a another embodiment 6, the invention provides compounds of the formula (I) according to embodiment 2, and wherein $R^1$ is $C_{1-6}$ alkyl, phenyl, tetrahydropyranyl or —$CH_2$-tetrahydropyranyl wherein each $R^1$ is optionally independently substituted with 1-3 substituents chosen from $C_{1-4}$ alkyl group and halogen;

$R^2$ and $R^3$ are methyl;

$R^4$ is hydrogen;

$R^5$ is isoxazolyl, pyrazolyl or pyridinyl, wherein each $R^5$ is optionally independently substituted with 1-3 substituents chosen from $C_{1-4}$ alkyl group, hydroxyl and halogen;

or a pharmaceutically acceptable salt thereof.

In another embodiment 7, the invention provides compounds of the formula (I) according to embodiment 6 above and wherein $R^1$ is $C_{1-4}$ alkyl, phenyl, tetrahydropyranyl or —$CH_2$-tetrahydropyranyl, wherein each $R^1$ is optionally independently substituted with a substituent chosen from trifluoromethyl and chloro;

$R^5$ is isoxazolyl, pyrazolyl or pyridinyl, wherein each $R^5$ is optionally independently substituted with 1-2 substituents chosen from $C_{1-4}$ alkyl group and trifluoromethyl or a pharmaceutically acceptable salt thereof.

In another embodiment 8 the invention provides compounds of the formula (I) according to any of the preceding embodiments described above, and wherein $R^2$ and $R^3$ are methyl;

or a pharmaceutically acceptable salt thereof.

In another embodiment 9 the invention provides compounds of the formula (I) according to any of the preceding embodiments and wherein L is a bond or a pharmaceutically acceptable salt thereof.

In another embodiment 10 the invention provides compounds of the formula (I) according to any of the preceding embodiments and wherein L is —C(O)—;

or a pharmaceutically acceptable salt thereof.

In another embodiment 11 the invention provides compounds of the formula (I) according to any of the preceding embodiments and wherein L is —C(O)—NH—
or a pharmaceutically acceptable salt thereof.

In another embodiment there is provided a compound of the formula (IA)

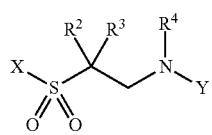
(IA)

wherein

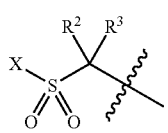

of the formula (IA) is chosen from column A1-A4 in Table I, and

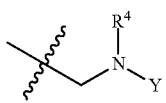

of the formula (IA) is chosen from column B1-B7 in Table I,

TABLE I

| | |
|---|---|
| A1 | 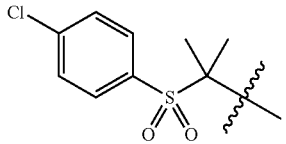 [SMILES: *C(C)(C)S(=O)(=O)c1ccc(Cl)cc1] |
| A2 | 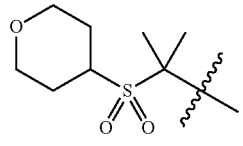 [SMILES: *C(C)(C)S(=O)(=O)C1CCOCC1] |
| A3 | 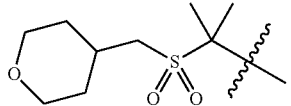 [SMILES: *C(C)(C)S(=O)(=O)CC1CCOCC1] |
| A4 | 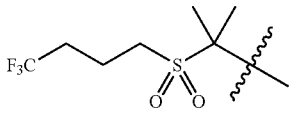 |
| A5 | |
| A6 | |
| A7 | |
| B1 | 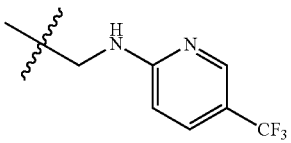 [SMILES: *CNc1ccc(C(F)(F)F)cn1] |

TABLE I-continued

| | |
|---|---|
| B2 | 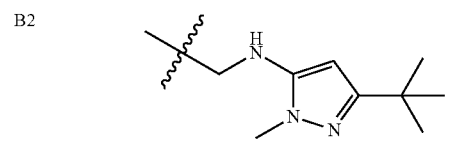 |
| B3 | 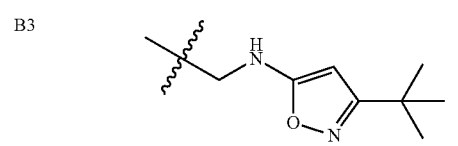 |
| B4 | 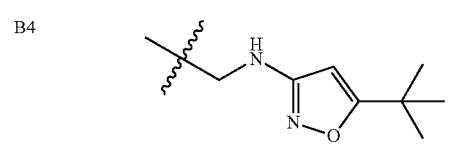 |
| B5 | 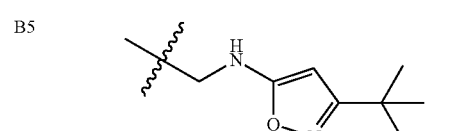 |
| B6 | 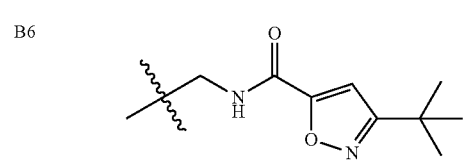 |
| B7 | 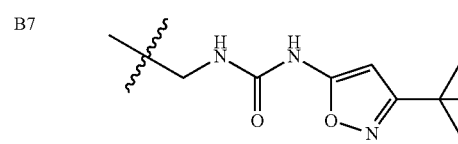 | or a pharmaceutically acceptable salt thereof.

In another embodiment, the invention provides made compounds in Table II which can be made in view of the general schemes, examples and methods known in the art.

TABLE II

| Example | Structure |
|---|---|
| 1 | 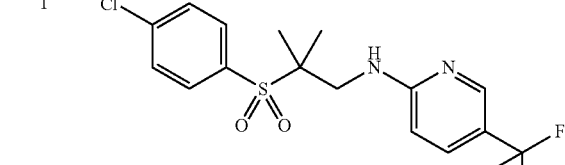 |
| 2 | 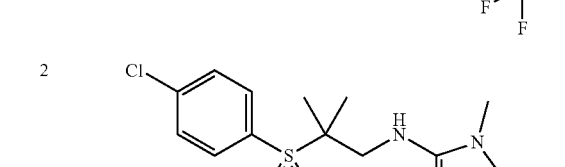 |

TABLE II-continued

| Example | Structure |
|---|---|
| 3 | (4-chlorophenyl sulfonyl compound with tert-butyl isoxazole) |
| 4 | (tetrahydropyranylmethyl sulfonyl compound with tert-butyl isoxazole) |
| 5 | (tetrahydropyranyl sulfonyl compound with tert-butyl isoxazole) |
| 6 | (trifluoropropyl sulfonyl compound with hydroxymethyl tert-butyl isoxazole) |
| 7 | (trifluoropropyl sulfonyl amide compound with tert-butyl isoxazole) |
| 8 | (tetrahydropyranyl sulfonyl amide compound with tert-butyl isoxazole) |
| 9 | (trifluorobutyl sulfonyl urea compound with tert-butyl isoxazole) |

TABLE II-continued

| Example | Structure |
|---|---|
| 10 | (tetrahydropyranyl sulfonyl urea compound with tert-butyl isoxazole) | or a pharmaceutically acceptable salt thereof.

In another generic embodiment II, the invention provides compounds of the formula

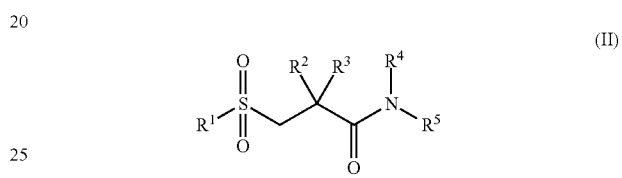

(II)

wherein:
R¹ is $C_{1-10}$ alkyl, $C_{3-10}$ cycloalkyl, 3-10 membered saturated heterocyclic ring, $C_{1-5}$ alkyl-heterocyclic ring, 5-10 membered mono or bicyclic heteroaryl ring, $C_{1-5}$ alkyl-heteroaryl ring, 5-10 membered mono or bicyclic aryl ring or $C_{1-5}$ alkyl-aryl ring, wherein each R¹ is optionally independently substituted with 1-3 substituents chosen from $C_{1-4}$ alkyl group, $C_{3-10}$ cycloalkyl, $C_{1-4}$ alkoxy, $C_{1-4}$ alkylsulfonyl, $C_{1-4}$ acyl, oxo, phenyl, cyano, hydroxyl and halogen;

R² and R³ are $C_{1-4}$ alkyl or hydrogen with the proviso that both R² and R³ cannot be hydrogen; or R² and R³ together with the carbon atom to which they are attached form a 3- to 6-membered cycloalkyl ring or heterocyclic ring;

R⁴ is hydrogen or methyl;

R⁵ is 5-10 membered mono or bicyclic heteroaryl ring optionally independently substituted with 1-3 substituents chosen from $C_{1-4}$ alkyl group, cyano, —$C_{1-8}$ branched or unbranched alkyl —O—R⁶, $C_{3-8}$-cycloalkyl-O—R⁶, —$C_{1-3}$ branched or unbranched alkyl —R⁷ and aryl-R⁸ each R⁶ is independently hydrogen, $C_{1-4}$ alkyl, —$C_{1-4}$ alkyl-O $C_{1-4}$ alkyl, or —$C_{1-4}$ alkyl-OH;

R⁷ is a 5-6 membered heteroaryl ring;

R⁸ is hydroxyl, alkoxy, alkylsulfonyl, cyano, halogen or $C_{1-4}$ alkyl wherein any carbon atom on the formula (I) or any R substituent listed above is optionally partially or fully halogenated where possible;

or a pharmaceutically acceptable salt thereof.

In another embodiment 2, the invention provides compounds of the formula (I) according to the preceding generic embodiment described above, and wherein R¹ is $C_{1-6}$ alkyl, phenyl, cyclopropyl, cyclobutyl, cyclopentyl, cyclohexyl, cycloheptyl, cyclooctyl, —$CH_2$-cyclopropyl, —$CH_2$-cyclobutyl, —$CH_2$—$CH_2$-cyclopropyl, —$CH_2$—$CH_2$-cyclobutyl, tetrahydrofuranyl, tetrahydropyranyl, azetidinyl, piperidinyl, thiomorpholinyl, 1,1-dioxo-1λ⁶-thiomorpholinyl, morpholinyl, pyrrolidinyl, piperazinyl, benzyl, —$CH_2$-tetrahydrofuranyl, —$CH_2$-tetrahydropyranyl, —$CH_2$—$CH_2$-tetrahydrofuranyl, —$CH_2$—$CH_2$-tetrahydropyranyl, benzoxazolyl, benzothiazolyl, benzimidazolyl, oxazolyl, isoxazolyl, thiazolyl, pyrazolyl, pyrrolyl, imidazolyl, thienyl, thiadiazolyl, pyridinyl, pyrimidinyl, pyridazinyl, pyrazinyl, quinolinyl, isoquinolinyl, indolyl, benzofuranyl or benzopyranyl, wherein each $R^1$ is optionally independently substituted with 1-3 substituents chosen from $C_{1-4}$ alkyl group, $C_{1-4}$ alkoxy, $C_{1-4}$ alkylsulfonyl, $C_{1-4}$ acyl, oxo, phenyl, cyano, hydroxyl and halogen;

$R^2$ and $R^3$ are independently methyl, ethyl, n-propyl, isopropyl, t-Butyl, or hydrogen with the proviso that both $R^2$ and $R^3$ cannot be hydrogen; or $R^2$ and $R^3$ together with the carbon to which they are attached form a cyclopropyl, cyclobutyl, or cyclopentyl ring;

$R^4$ is hydrogen or methyl;

$R^5$ is isoxazolyl, thiazolyl, pyrazolyl, pyrrolyl, imidazolyl, thienyl, thiadiazolyl, pyridinyl, pyrimidinyl, pyridazinyl, pyrazinyl, triazinyl, tetrazolyl, oxazolyl, oxadiazolyl or furanyl, wherein each $R^5$ is optionally independently substituted with 1-3 substituents chosen from $C_{1-4}$ alkyl group, cyano, —$C_{1-8}$ branched or unbranched alkyl —O—$R^6$, -cycloalkyl-O—$R^6$, —$C_{1-3}$ branched, or unbranched alkyl —$R^7$ and phenyl-$R^8$;

each $R^6$ is independently hydrogen or $C_{1-4}$ alkyl, —$C_{1-4}$ alkyl-O$C_{1-4}$ alkyl, or —$C_{1-4}$ alkyl-OH;

$R^7$ is pyrazolyl, isoxazolyl, oxazolyl, oxadiazolyl or thiazolyl;

$R^8$ is hydroxyl, $C_{1-3}$ alkoxy, $C_{1-4}$ alkylsulfonyl, cyano, halogen or $C_{1-4}$ alkyl;

or a pharmaceutically acceptable salt thereof.

In another embodiment 3, the invention provides compounds of the formula (I) according to any of the preceding embodiments, and wherein $R^1$ is $C_{1-6}$ alkyl, phenyl or tetrahydropyranyl, wherein each $R^1$ is optionally independently substituted with 1-3 substituents chosen from $C_{1-4}$ alkyl group and halogen;

or a pharmaceutically acceptable salt thereof.

In another embodiment 4, the invention provides compounds of the formula (I) according to any of the preceding embodiments, and wherein $R^2$ and $R^3$ are methyl;

or a pharmaceutically acceptable salt thereof.

In another embodiment 5, the invention provides compounds of the formula (I) according to any of the preceding embodiments described above, and wherein $R^4$ is hydrogen;

$R^5$ is isoxazolyl, thiazolyl or thiadiazolyl, wherein each $R^5$ is optionally independently substituted with 1-3 substituents chosen from $C_{1-4}$ alkyl group and $C_{1-4}$ alkyl-OH;

or a pharmaceutically acceptable salt thereof.

In a another embodiment 6, the invention provides compounds of the formula (I) according to embodiment 2, and wherein $R^1$ is $C_{1-6}$ alkyl, phenyl or tetrahydropyranyl, wherein each $R^1$ is optionally independently substituted with 1-3 substituents chosen from $C_{1-4}$ alkyl group and halogen.

$R^2$ and $R^3$ are methyl;

$R^4$ is hydrogen;

$R^5$ is isoxazolyl, thiazolyl or thiadiazolyl, wherein each $R^5$ is optionally independently substituted with 1-3 substituents chosen from $C_{1-4}$ alkyl group and $C_{1-4}$ alkyl-OH;

or a pharmaceutically acceptable salt thereof.

In another embodiment 7, the invention provides compounds of the formula (I) according to embodiment 6 above and wherein $R^1$ is $C_{1-4}$ alkyl, phenyl or tetrahydropyranyl, wherein each $R^1$ is optionally independently substituted with a trifluoromethyl group;

$R^5$ is isoxazolyl, thiazolyl or thiadiazolyl, wherein each $R^5$ is optionally independently substituted with a substituents chosen from tert-butyl group and $C_{1-4}$ alkyl-OH;

or a pharmaceutically acceptable salt thereof.

In another embodiment 8 the invention provides compounds of the formula (I) according to any of the preceding embodiments described above, and wherein $R^2$ and $R^3$ are methyl;

or a pharmaceutically acceptable salt thereof.

In another embodiment there is provided a compound of the formula (IIA)

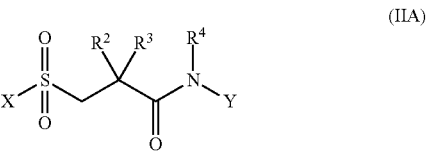

(IIA)

wherein

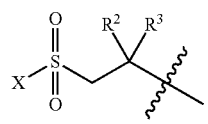

of the formula (IIA) is chosen from column A1-A3 in Table III, and

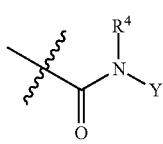

of the formula (IIA) is chosen from column B1-B6 in Table III,

TABLE III

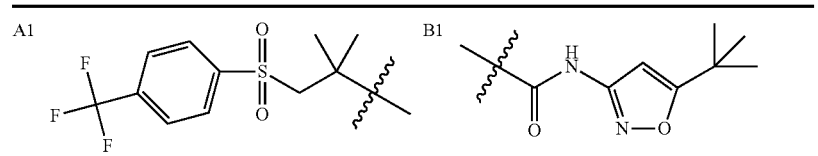

TABLE III-continued
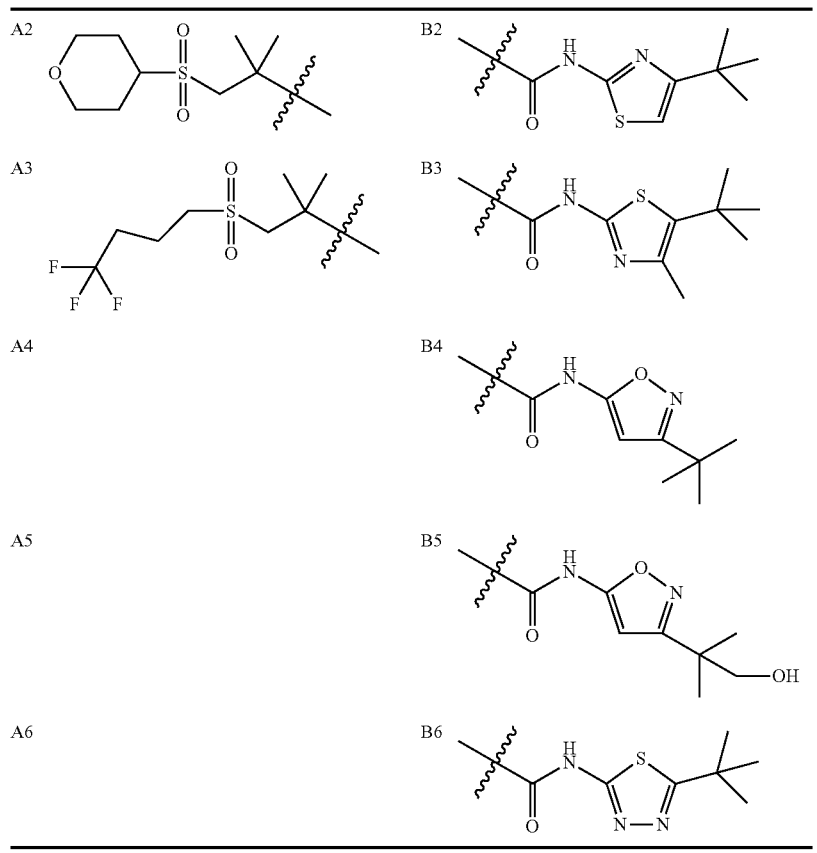
or a pharmaceutically acceptable salt thereof.
In another embodiment, the invention provides made compounds in Table IV which can be made in view of the general schemes, examples and methods known in the art.
TABLE IV
| Example | Structure |
|---|---|
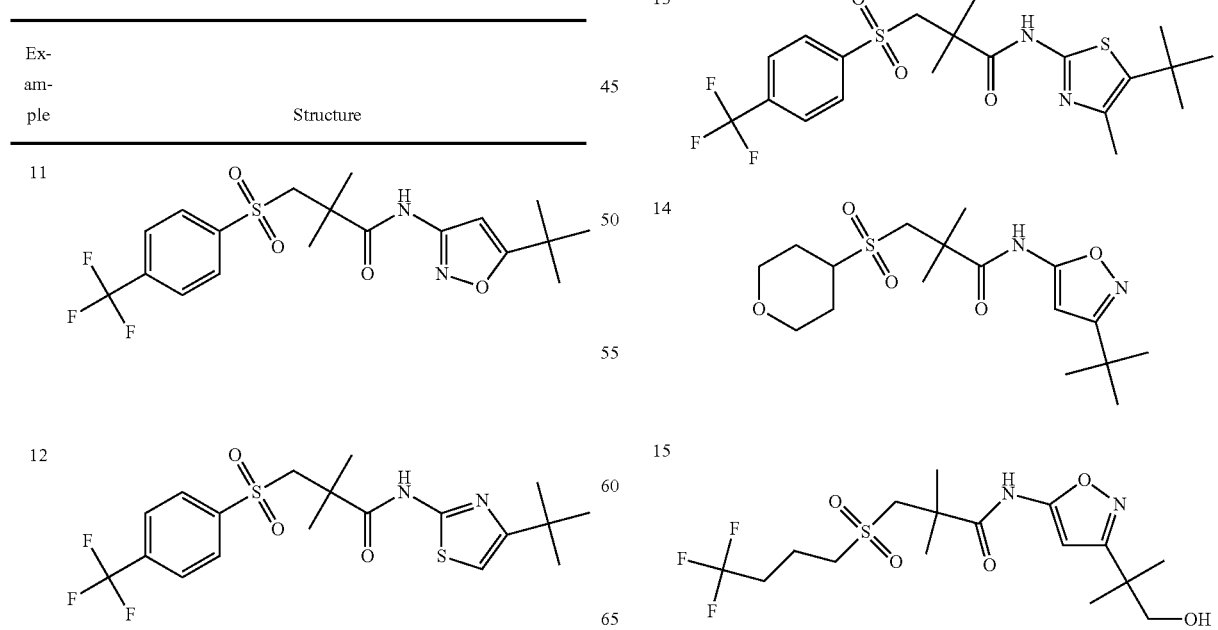

TABLE IV-continued

| Example | Structure |
|---|---|
| 16 | (tetrahydropyran-4-yl sulfonyl methyl, dimethyl, amide, 5-tert-butyl-1,3,4-thiadiazol-2-yl) |
| 17 | (4,4,4-trifluorobutyl sulfonyl methyl, dimethyl, amide, 3-tert-butyl-isoxazol-5-yl) |
| 18 | (tetrahydropyran-4-yl sulfonyl methyl, dimethyl, amide, 3-(2-hydroxy-2-methylpropyl)-isoxazol-5-yl) |
| 19 | (4,4,4-trifluorobutyl sulfonyl methyl, dimethyl, amide, 5-tert-butyl-1,3,4-thiadiazol-2-yl) | or a pharmaceutically acceptable salt thereof.

The invention also relates to pharmaceutical preparations, containing as active substance one or more compounds of formula (I), or the pharmaceutically acceptable derivatives thereof, optionally combined with conventional excipients and/or carriers.

Compounds of the invention also include their isotopically-labelled forms. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g., $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. An active agent of a combination of the present invention, a prodrug thereof, or a pharmaceutically acceptable salt of either which contains one or more of the above-mentioned isotopes and/or other isotopes of other atoms is contemplated to be within the scope of the present invention.

The invention includes the use of any compounds of described above containing one or more asymmetric carbon atoms may occur as racemates and racemic mixtures, single enantiomers, diastereomeric mixtures and individual diastereomers. Isomers shall be defined as being enantiomers and diastereomers. All such isomeric forms of these compounds are expressly included in the present invention. Each stereogenic carbon may be in the R or S configuration, or a combination of configurations.

Some of the compounds of formula (I) can exist in more than one tautomeric form. The invention includes methods using all such tautomers.

All terms as used herein in this specification, unless otherwise stated, shall be understood in their ordinary meaning as known in the art. For example, "$C_{1-4}$alkoxy" is a $C_{1-4}$alkyl with a terminal oxygen, such as methoxy, ethoxy, propoxy, butoxy. All alkyl, alkenyl and alkynyl groups shall be understood as being branched or unbranched where structurally possible and unless otherwise specified. Other more specific definitions are as follows:

Carbocycles or cycloalkyls include hydrocarbon rings containing from three to twelve carbon atoms. These carbocycles may be either aromatic either aromatic or non-aromatic ring systems. The non-aromatic ring systems may be mono- or polyunsaturated. Preferred carbocycles include but are not limited to cyclopropyl, cyclobutyl, cyclopentyl, cyclopentenyl, cyclohexyl, cyclohexenyl, cycloheptanyl, cycloheptenyl, phenyl, indanyl, indenyl, benzocyclobutanyl, dihydronaphthyl, tetrahydronaphthyl, naphthyl, decahydronaphthyl, benzocycloheptanyl and benzocycloheptenyl. Certain terms for cycloalkyl such as cyclobutanyl and cyclobutyl shall be used interchangeably.

The term "heterocycle" refers to a stable nonaromatic 3-10 membered (but preferably, 5 or 6 membered) monocyclic or nonaromatic 8-11 membered bicyclic heterocycle radical which may be either saturated or unsaturated. Each heterocycle consists of carbon atoms and one or more, preferably from 1 to 4 heteroatoms chosen from nitrogen, oxygen and sulfur. The heterocycle may be attached by any atom of the cycle, which results in the creation of a stable structure.

The term "heteroaryl" shall be understood to mean an aromatic 5-10 membered monocyclic or 8-11 membered bicyclic ring containing 1-4 heteroatoms such as N, O and S.

Unless otherwise stated, heterocycles and heteroaryl include but are not limited to, for example benzoxazolyl, benzothiazolyl, benzimidazolyl, tetrahydropyranyl, dioxanyl, tetrahydrofuranyl, oxazolyl, isoxazolyl, thiazolyl, pyrazolyl, pyrrolyl, imidazolyl, thienyl, thiadiazolyl, triazolyl, thiomorpholinyl, 1,1-Dioxo-1λ$^6$-thiomorpholinyl, morpholinyl, pyridinyl, pyrimidinyl, pyridazinyl, pyrazinyl, triazinyl, pyrrolidinyl, piperidinyl, piperazinyl, purinyl, quinolinyl, Dihydro-2H-quinolinyl, isoquinolinyl, quinazolinyl, indazolyl, thieno[2,3-d]pyrimidinyl, indolyl, isoindolyl, benzofuranyl, benzopyranyl and benzodioxolyl.

The term "heteroatom" as used herein shall be understood to mean atoms other than carbon such as O, N, S and P.

In all alkyl groups or carbon chains one or more carbon atoms can be optionally replaced by heteroatoms: O, S or N, it shall be understood that if N is not substituted then it is NH, it shall also be understood that the heteroatoms may replace either terminal carbon atoms or internal carbon atoms within a branched or unbranched carbon chain. Such groups can be substituted as herein above described by groups such as oxo to result in defintions such as but not limited to: alkoxycarbonyl, acyl, amido and thioxo.

The term "aryl" as used herein shall be understood to mean aromatic carbocycle.

Each aryl or heteroaryl unless otherwise specified includes it's partially or fully hydrogenated derivative. For example, quinolinyl may include decahydroquinolinyl and tetrahydroquinolinyl, naphthyl may include its hydrogenated derivatives such as tetrahydronaphthyl. Other partially or fully hydrogenated derivatives of the aryl and heteroaryl compounds described herein will be apparent to one of ordinary skill in the art.

As used herein, "nitrogen" and "sulfur" include any oxidized form of nitrogen and sulfur and the quaternized form of any basic nitrogen. For example, for an —S—$C_{1-6}$ alkyl radical, unless otherwise specified, this shall be understood to include —S(O)—$C_{1-6}$ alkyl and —S(O)$_2$—$C_{1-6}$ alkyl.

The term "halogen" as used in the present specification shall be understood to mean bromine, chlorine, fluorine or iodine, preferably fluorine and chlorine. The definitions "partially or fully halogenated"; partially or fully fluorinated; "substituted by one or more halogen atoms", includes for example, mono, di or tri halo derivatives on one or more carbon atoms. For alkyl, a nonlimiting example would be —$CH_2CHF_2$, —$CF_3$ etc.

The compounds of the invention are only those which are contemplated to be 'chemically stable' as will be appreciated by those skilled in the art. For example, a compound which would have a 'dangling valency', or a 'carbanion' are not compounds contemplated by the inventive methods disclosed herein.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the formula (I).

Pharmaceutically acceptable salts include those derived from pharmaceutically acceptable inorganic and organic acids and bases. Examples of suitable acids include hydrochloric, hydrobromic, sulfuric, nitric, perchloric, fumaric, maleic, phosphoric, glycolic, lactic, salicylic, succinic, toluene-p-sulfuric, tartaric, acetic, citric, methanesulfonic, formic, benzoic, malonic, naphthalene-2-sulfuric and benzenesulfonic acids. Other acids, such as oxalic acid, while not themselves pharmaceutically acceptable, may be employed in the preparation of salts useful as intermediates in obtaining the compounds and their pharmaceutically acceptable acid addition salts. Salts derived from appropriate bases include alkali metal (e.g., sodium), alkaline earth metal (e.g., magnesium), ammonium and N—($C_1$-$C_4$ alkyl)$_4$$^+$ salts.

In addition, within the scope of the invention is use of prodrugs of compounds of the formula (I). Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

The compounds of formula I may be made using the general synthetic methods described to below, which also constitute part of the invention.

General Synthetic Methods

The invention also provides processes for making compounds of Formula (I), (IA), (II) and (IIA). In all methods, unless specified otherwise, $R^1$, $R^2$, $R^3$, $R^4$, $R^5$ and L in the formulas below shall have the meaning of $R^1$, $R^2$, $R^3$, $R^4$, $R^5$ and L in Formula (I) and Formula (II) of the invention described herein above.

Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Synthetic Examples section. Typically, reaction progress may be monitored by thin layer chromatography (TLC), if desired, and intermediates and products may be purified by chromatography on silica gel and/or by recrystallization.

The examples which follow are illustrative and, as recognized by one skilled in the art, particular reagents or conditions could be modified as needed for individual compounds without undue experimentation. Starting materials and intermediates used, in the methods below, are either commercially available or easily prepared from commercially available materials by those skilled in the art. Synthetic methods disclosed in WO2008098025, WO2008014199, WO2008039645, and WO2009061652 may also be used in preparing compounds of the invention.

Compounds of Formula (I) and (IA) may be synthesized by the method illustrated in Scheme 1

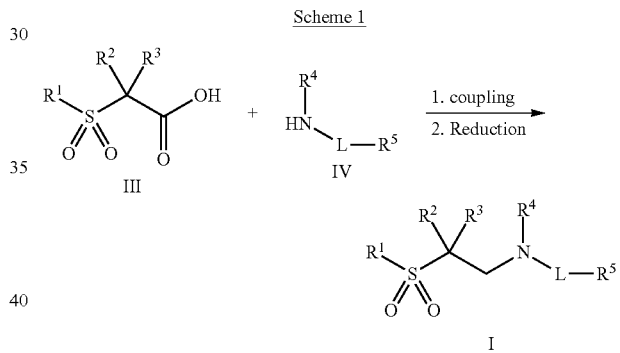

Scheme 1

As shown in scheme 1, reacting the acid of formula III with a reagent such as thionyl chloride or oxalyl chloride, provides the acid chloride which is then reacted with an amine of formula IV, in a suitable solvent, in the presence of a suitable base, to provide an amide. Reduction of the amide with a suitable reagent such as borane or lithium aluminum hydride, in a suitable solvent such as THF, provides a compound of formula (I). Alternatively, the acid of formula III may also be coupled with an amine of formula IV under standard coupling conditions, to provide an amide which is further reduced to provide a compound of formula (I). Standard peptide coupling reactions known in the art (see for example M. Bodanszky, 1984, The Practice of Peptide Synthesis, Springer-Verlag) may be employed in these syntheses. An example of suitable coupling conditions is treatment of a solution of the carboxylic acid in a suitable solvent such as DMF with EDC, HOBT, and a base such as diisopropylethylamine, followed by the desired amine Further modification of the initial product of formula (I) by methods known in the art and illustrated in the Examples below, may be used to prepare additional compounds of this invention.

Intermediate acid III may be made by the method outlined in Scheme 2

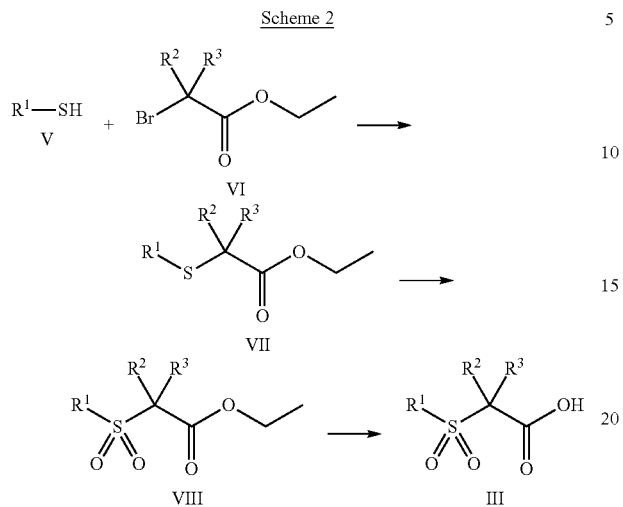

As illustrated in above, reaction of a thiol of formula V with a bromo ethyl ester of formula VI, in a suitable solvent, in the presence of a suitable base, provides a thioether of formula VII. Reacting the thioether of formula VII with a suitable oxidizing agent provides the corresponding sulfone of formula VIII. Hydrolysis of the ester group of sulfone of formula VIII, in a suitable solvent, in the presence of a suitable base such as lithium hydroxide, provides the corresponding acid of formula III.

Intermediate acid III may also be made by the method outlined in Scheme 3

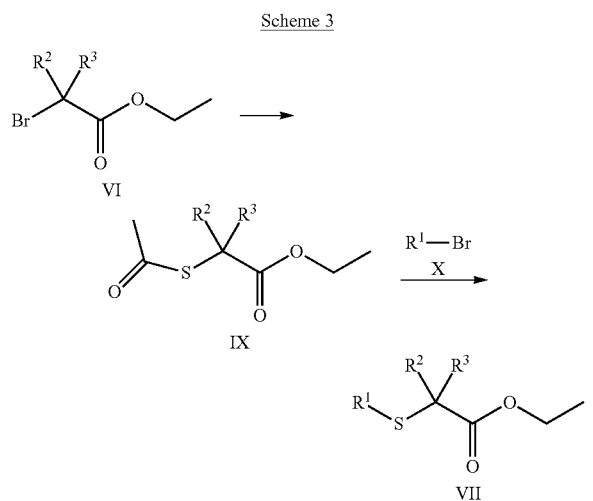

Reaction of the starting bromoester of formula VI with a reagent such as potassium thioacetate, in a suitable solvent, provides a thioacetic acid ester of formula IX. Reaction of the thioacetic acid ester IX with a bromide of formula X, in a suitable solvent in the presence of a suitable base, provides the corresponding sulfanyl acid ethyl ester of formula VII. The sulfanyl acid ethyl ester of formula VII may be converted to intermediate acid of formula III by the sequence of steps shown in scheme 2.

Intermediate acid III may be made by the method outlined in Scheme 4

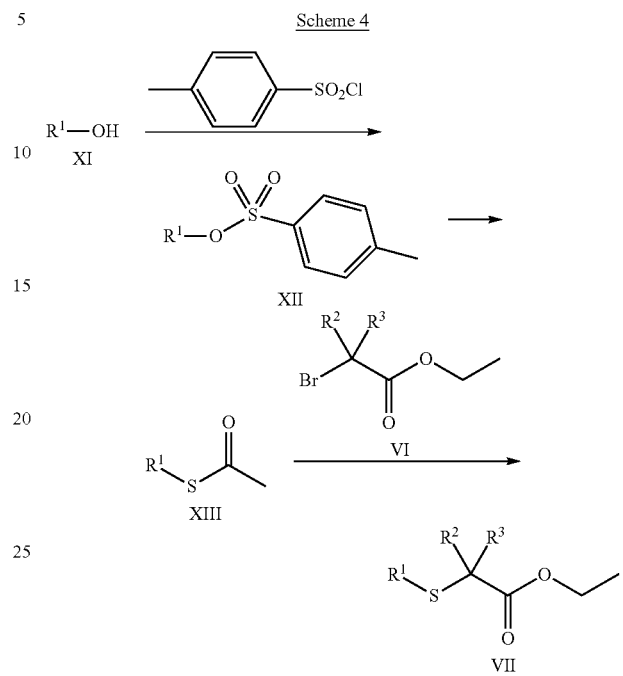

As illustrated in scheme 4, reaction of an alcohol of formula XI with p-toluenesulfonyl chloride, in a suitable solvent, in the presence of a suitable base, provides the sulfonic acid ester of formula XII. Reaction of the compound of formula XII with potassium thioacetate, in a suitable solvent, provides a compound of formula XIII. Reaction of the intermediate of formula XIII with the bromoester of formula VI, in a suitable solvent, in the presence of a suitable base, provides the intermediate of formula VII which may be converted to the desired intermediate acid of formula III by the reaction sequence shown in scheme 2.

Compounds of formula (I), wherein L is —CO— or —C(O)—NH— may be prepared according to the method outlined in scheme 5.

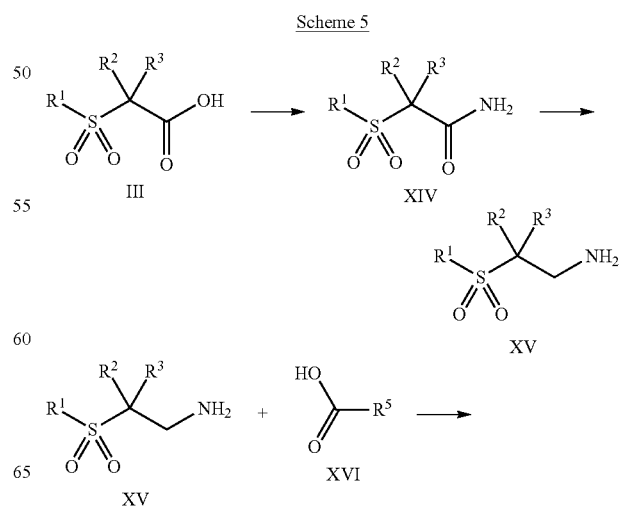

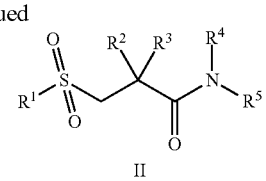

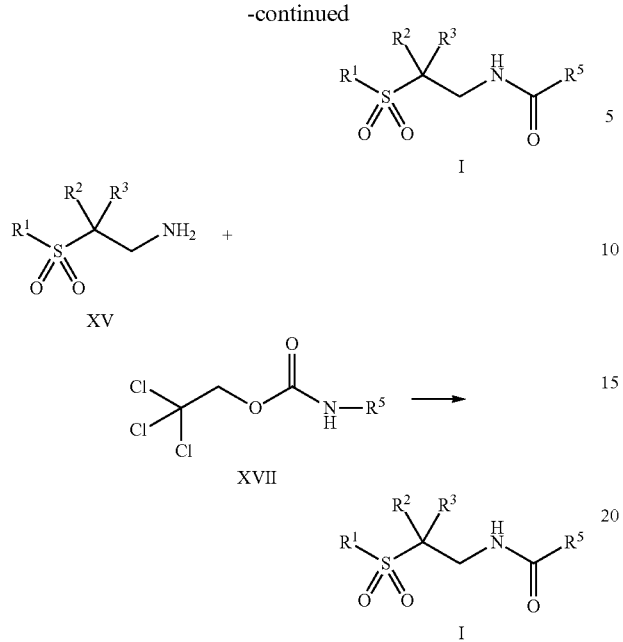

Reaction of the acid of formula III, with oxalyl chloride or thionyl chloride provides the corresponding acid chloride. Reaction of this acid chloride with ammonia, in a suitable solvent, at a suitable temperature, provides an amide of formula XIV. Reduction of the amide of formula XIV with a suitable reducing agent such as lithium aluminum hydride, in a suitable solvent provides the corresponding amine of formula XV. Coupling of the amine of formula XV with an acid of formula XVI or its acid chloride, under standard conditions, provides a compound of formula (I), wherein L=—C(O)—

Alternatively, reaction of the amine of formula XV with a carbamic acid trichloroethyl ester of formula XVII, in a suitable solvent, in the presence of a suitable base, provides a compound of formula (I), wherein L=—C(O)—NH—.

Compounds of Formula (II) and (IIA) may be made by the method outlined in Scheme 6

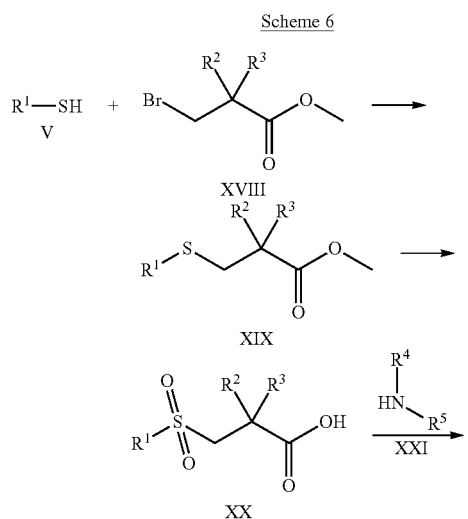

As illustrated in above, reaction of a thiol of formula V with a bromo methyl ester of formula XVIII, in a suitable solvent, in the presence of a suitable base, provides a thioether of formula XIX. Reacting the thioether of formula XIX with a suitable oxidizing agent followed by hydrolysis of the ester group, provides the corresponding sulfone of formula XX. Reaction of the acid or corresponding acid chloride with an amine of formula XXI, as in scheme 1, provides a compound of formula (II).

Compounds of Formula (II) and (IIA) may also be made by the method outlined in Scheme 7

Scheme 7

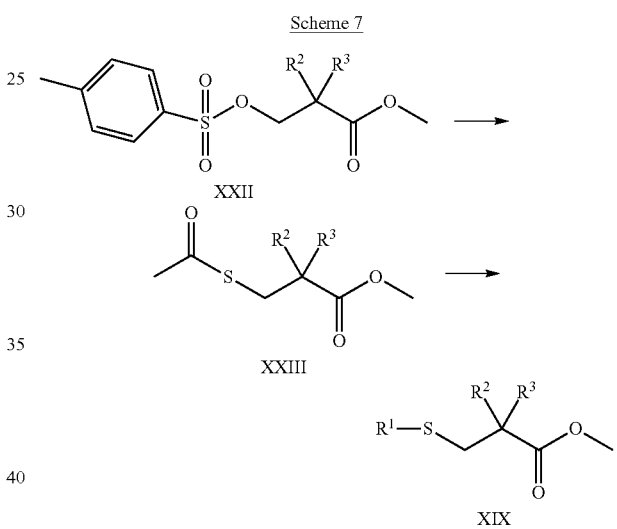

As illustrated in scheme 7, reaction of an sulfonyloxy compound of formula XXII with potassium thioacetate, in a suitable solvent, in the presence of sodium iodide, provides an acetylsulfanyl compound of formula XXIII. Reaction of the compound of formula with a halo compound $R^1X$, in a suitable solvent, in the presence of a suitable base, provides a compound of formula XIX. X=Cl, Br or I. C The intermediate of formula XIX may be further converted to a compound of formula II according to the method in scheme 6.

Further modification of the initial product of formula (II) by methods known in the art and illustrated in the Examples below may be used to prepare additional compounds of this invention.

SYNTHETIC EXAMPLES

The manner in which the compounds of the invention can be made will be further understood by way of the following Examples.
Method A:
Intermediates in method A are prepared as described in WO2008039645, Boehringer Ingelheim International GmbH. or as described in WO2008014199, Boehringer Ingelheim International GmbH.

Synthesis of (5-tert-Butyl-2-methyl-2H-pyrazol-3-yl)-[2-(4-chloro-benzenesulfonyl)-2-methyl-propyl]-amine (Example 2)

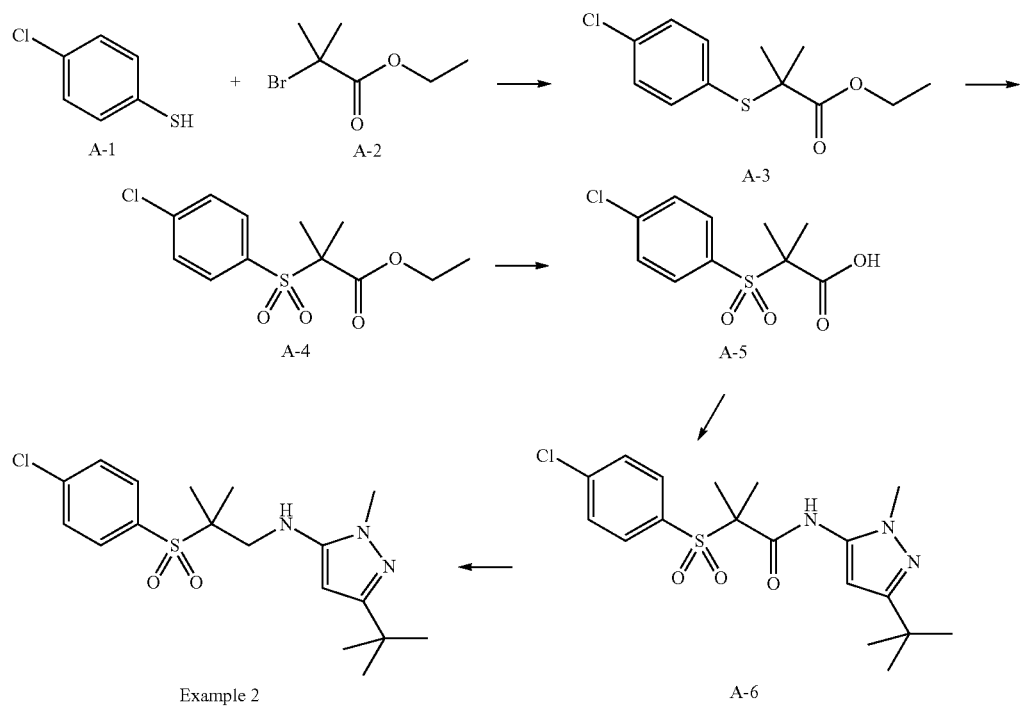

Step 1: Synthesis of Compound A-3

To a stirred solution of 60 g (0.415 mol) of compound A-1 in ethanol (450 mL) are added 23.23 g (0.415 mol) KOH pellets, followed by 80.90 g (0.415 mol) of compound A-2. The reaction mixture is heated to reflux for 18 h and cooled to room temperature. The solid (KBr) is separated by filtration, rinsed with ethanol (3×100 mL), the filtrate concentrated under reduced pressure and the residue dissolved in DCM (600 mL). The organic layer is washed with water (500 mL), the aqueous washes are back-extracted with DCM (100 mL). The combined organics are washed with brine (400 mL) and dried over $Na_2SO_4$. Filtration and concentration under reduced pressure affords 102.82 g of compound A-3 as a yellow oil. Yield: 96%, ES-MS: m/z 259 [M+H]; $^1$H-NMR (400 MHz, CHLOROFORM-d) δ ppm 1.23 (3H, t, J=7.21 Hz), 1.48 (6H, s), 4.12 (2H, q, J=7.09 Hz), 7.28-7.33 (2H, m), 7.37-7.43 (2H, m)

Step 2: Synthesis of Compound A-4

To a solution of 102.85 g (0.399 mol) of compound A-3 in dioxane/water (5:1, 1000 mL) are added in 3 portions 489.5 g (0.798 mol) of potassium monopersulfate triple salt (OXON®). The white suspension is stirred at room temperature for 18 h. The white solid is separated by filtration and washed with dioxane (750 mL). The filtrate is concentrated under reduced pressure to remove the organic solvent. The resulting aqueous solution is extracted with DCM (800 mL). The organic extracts are washed with water (600 mL) followed by brine (600 mL), dried over $Na_2SO_4$ and filtered. The filtrate is concentrated under reduced pressure to afford 107.26 g of compound A-4 as yellow oil. Yield: 93%; ES-MS: m/z 291 [M+H]; $^1$H-NMR (250 MHz, CHLOROFORM-d) δ ppm 1.22 (3H, q, J=7.17 Hz), 1.60 (6H, s), 4.13 (2H, q, J=7.14 Hz), 7.51 (2H, d, J=8.51 Hz), 7.71-7.82 (2H, m)

Step 3: Synthesis of Compound A-5

To a solution of 107.26 g (0.369 mol) of compound A-4 in THF/water (4:1, 900 mL) are added 29.58 g (0.739 mol) of sodium hydroxide in a solution of water (100 mL). The reaction is stirred at room temperature for 18 h. The reaction is concentrated under reduced pressure to remove organic solvents and then re-diluted with water to make a 600 mL solution. The aqueous solution is washed with DCM (500 mL). The basic aqueous layer is cooled in an ice bath and then acidified with conc HCl solution to pH 2. The acidic aqueous layer is extracted with DCM (2×500 mL). The combined organic extracts are washed with brine (500 mL), dried over $Na_2SO_4$ and filtered. Concentration of the filtrate under reduced pressure affords 89.86 g of compound A-5 as an off-white solid. Yield: 93%; ES-MS: m/z 263 [M+H]; $^1$H-NMR (250 MHz, CHLOROFORM-d) δ ppm 1.64 (6H, s), 7.56 (2H, d, J=8.87 Hz), 7.84 (2H, d, J=8.87 Hz)

Step 4: Synthesis of Compound A-6

Activation of 10 g (38.2 mmol) of compound A-5 is achieved by treatment with thionyl chloride (17 mL) at 70° C.

for 3 h. The reaction mixture is cooled to room temperature and excess thionyl chloride is removed under reduced pressure.

The crude acid chloride is dissolved in DCM (100 mL) and added to a solution of 5.84 g (38.2 mmol) of 5-tert-butyl-2-methyl-2H-pyrazol-3-ylamine and N,N-diisopropylethylamine (13.27 mL) in DCM (150 mL). The reaction is stirred at room temperature for 16 h. The solvent is removed under reduced pressure. The residue is dissolved with DCM (300 mL) and washed with saturated aqueous NaHCO$_3$ solution (300 mL). The organic layer is separated and washed with brine (300 mL). and dried over Na$_2$SO$_4$, filtered and the filtrate is concentrated under reduced pressure. The crude product is purified by column chromatography (200 g silica, eluent: DCM, 0-20% ethyl acetate). The resulting solid is washed sparingly with cyclohexane, then dried under vacuum to afford 12.145 g of compound A-6 as a pink powder. Yield 80%; ES-MS: m/z 398/400 [M+H]; $^1$H-NMR (400 MHz, CHLOROFORM-d) δ ppm 1.30 (9H, s), 1.62 (6H, s), 3.78 (3H, s), 6.22 (1H, s), 7.48-7.68 (2H, m), 7.70-7.96 (2H, m), 8.88 (1H, s).

According to the above procedure the following amides are synthesized

Step 5: Synthesis of Example 2

To a solution of 300 mg (0.76 mmol) of compound A-6 in anhydrous THF (3 mL) is added borane (1M in THF, 3 mL) at room temperature under nitrogen atmosphere. The reaction is stirred at room temperature for 16 h, then heated to 50° C. for 4 h. After cooling, the reaction mixture is quenched by addition of methanol (3 mL), the solvent is removed under reduced pressure and the residue partitioned between DCM and saturated aqueous NaHCO$_3$ solution. The organic layer is washed with brine, dried (MgSO$_4$), filtered and the filtrate is concentrated under reduced pressure. The residue is purified by preparative HPLC (acidic method), followed by free-basing over MP-carbonate resin in DCM/methanol and concentration, which affords 136 mg of Example 2. Yield 47%; ES-MS; m/z 383 [M+H]; $^1$H NMR (400 MHz, CHLOROFORM-d) δ ppm 1.27 (9H, s), 1.39 (6H, s), 3.29 (2H, d, J=6.22 Hz), 3.63 (3H, s), 4.35 (1H, t, J=5.95 Hz), 5.27 (1H, s), 7.57 (2H, d, J=8.05 Hz), 7.81 (2H, d, J=8.23 Hz)

Examples in table 4, Method A are synthesised according to this procedure

Method B:

Intermediates in method B are prepared by adaptation of the synthetic method described in WO2008039645, Boehringer Ingelheim International GmbH.

TABLE 1

| Structure | $^1$H-NMR | Yield [%] | m/z [M + H] |
|---|---|---|---|
| (structure: 4-chlorophenyl-SO$_2$-C(CH$_3$)$_2$-C(O)NH-pyridyl-CF$_3$) | (400 MHz, CHLOROFORM-d) δ ppm 1.71 (6 H, s), 7.44-7.61 (2 H, m), 7.71-7.84 (2 H, m), 7.95 (1 H, dd, J = 8.74, 2.15 Hz), 8.18 (1 H, d, J = 8.74 Hz), 8.64 (1 H, s), 9.48 (1 H, br. s.) | 76 | 407/409 |
| (structure: 4-chlorophenyl-SO$_2$-C(CH$_3$)$_2$-C(O)NH-(1-methyl-3-tert-butyl-pyrazol-5-yl)) | (400 MHz, CHLOROFORM-d) δ ppm 1.30 (9 H, s), 1.62 (6 H, s), 3.78 (3 H, s), 6.22 (1 H, s), 7.48-7.68 (2 H, m), 7.70-7.96 (2 H, m), 8.88 (1H, s) | 80 | 398/400 |
| (structure: 4-chlorophenyl-SO$_2$-C(CH$_3$)$_2$-C(O)NH-(5-tert-butyl-isoxazol-3-yl)) | (400 MHz, CHLOROFORM-d) δ ppm 1.36 (9 H, s), 1.69 (6 H, s), 6.54 (1 H, s), 7.54 (2 H, d), 7.79 (2 H, d), 9.41 (1 H, s) | 84 | 385/387 |

Synthesis of (3-tert-Butyl-isoxazol-5-yl)-[2-methyl-2-(tetrahydro-pyran-4-ylmethanesulfonyl)-propyl]-amine (Example 4)

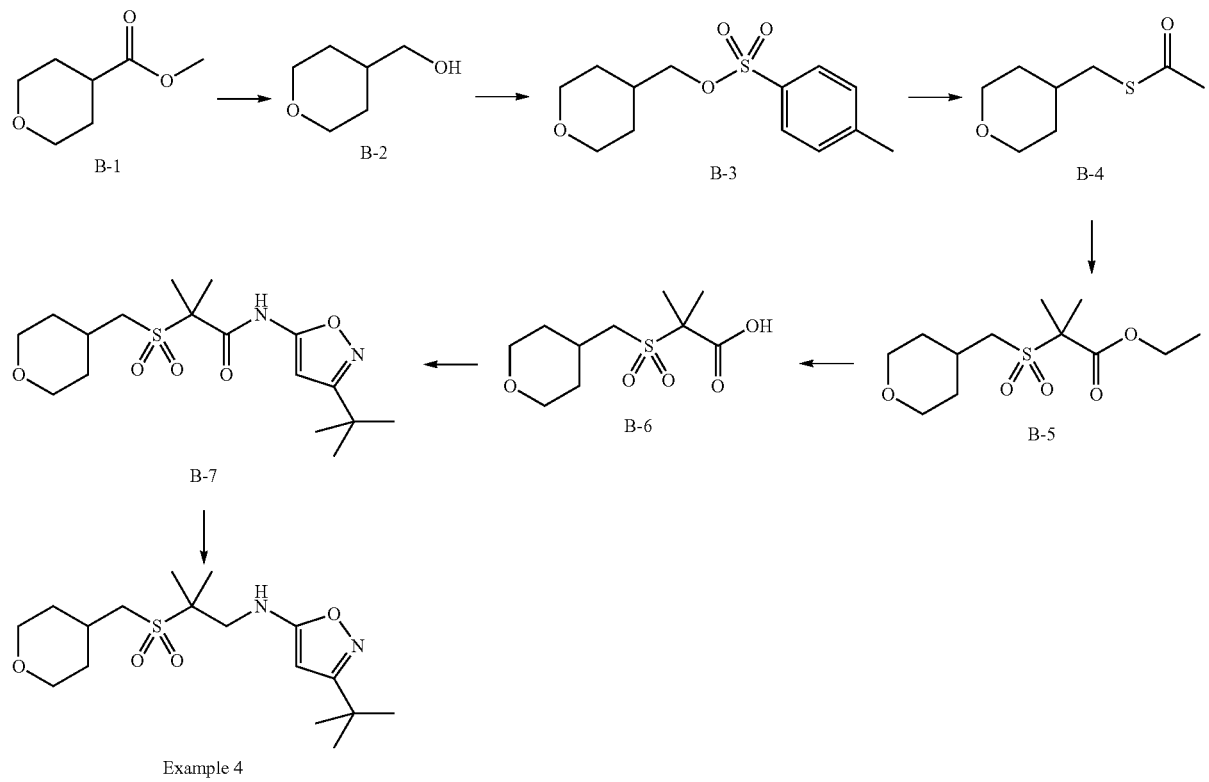

Example 4

Step 1: Synthesis of Compound B-2

To a solution of 250 mL of LiAlH$_4$ (2.3 M solution in THF, 0.575 mol) in THF (200 mL) is added dropwise a solution of 130 mL (0.974 mol) of compound B-1 in THF (900 mL) under nitrogen atmosphere (CAUTION: highly exothermic reaction!). The temperature is kept at 40-45° C. with an ice-bath. Upon complete addition, the reaction is stirred at room temperature for 1.5 h. The reaction is cooled in an ice-bath and quenched with addition of water (22 mL), 15% aqueous NaOH solution (21 mL) and water (66 mL). The resulting precipitate is removed by filtration through Celite® and is rinsed with THF (300 mL). The filtrate is concentrated under reduced pressure to afford 102.5 g of compound B-2 as a colorless oil. Yield: 91%; $^1$H NMR (400 MHz, CHLOROFORM-d) δ ppm 1.20-1.39 (2H, m), 1.56-1.83 (3H, m), 2.03 (1H, br. s.), 3.29-3.52 (4H, m), 3.89-4.05 (2H, m)

Step 2: Synthesis of B-3

Prepared as described by adaptation of the following literature reference:

Radziszewski, J. G. et al. *J. Am. Chem. Soc.* 1993, 115, 8401.

To a solution of 97 g (810 mmol) of compound B-2 in 2-methyltetrahydrofuran (190 mL) are added 165 mL of 50% aqueous NaOH solution. To this stirred suspension is added dropwise with cooling a solution of p-toluene-sulfonylchloride (283 g, 1.46 mol) in 2-methyltetrahydrofuran (280 mL). The reaction is stirred at 30-35° C. for 18 h. The suspension is poured into a mixture of ice-water (280 mL) and aqueous HCl solution (37%, 203 mL). After addition of methylcyclohexane (1.4 L) and further ice-water (0.2 L), the reaction mixture is stirred for 2 h in an ice-bath. The resulting crystalline precipitate is isolated by filtration and washed with methylcyclohexane (0.5 L) and water (0.5 L). Drying under reduced pressure at 40° C. gave 216 g of compound B-3 as white crystalline solid. Yield: 99%, ES-MS: m/z 271 [M+H]; $^1$H NMR (400 MHz, CHLOROFORM-d) δ ppm 1.19-1.35 (2H, m), 1.54-1.63 (2H, m), 1.85-2.02 (1H, m), 2.45 (3H, s), 3.28-3.39 (2H, m), 3.86 (2H, d, J=6.60 Hz), 3.93 (2H, dd, J=11.37, 4.52 Hz), 7.35 (2H, d, J=9.29 Hz), 7.78 (2H, d, J=8.31 Hz)

Step 3: Synthesis of B-4

Prepared as described by adaptation of the following literature reference:

Watson, R. J. et al. *Tetrahedron Lett.* 2002, 43, 683-685.

To a solution of 224 g (0.83 mol) of compound B-3 in methyl isobutylketone (1.6 L) are added 189 g (1.66 mol) of potassium thioacetate. The beige suspension is stirred at 70° C. for 4.5 h. The reaction mixture is cooled to room temperature and water (1.8 L) is added. The organic layer is washed with 10% aqueous K$_2$CO$_3$ solution (1.8 L) and water (1 L). The organic layer is filtered through Celite® (20 g), activated charcoal (20 g) and Na$_2$SO$_4$ (20 g) and the filtrate is concentrated under reduced pressure. The residual oil is azeotroped with methylcyclohexane (200 mL) and n-heptanes (250 mL) to afford 138 g of compound B-4 as a yellow-orange oil (CAUTION: Stench!). Yield: 96%; ES-MS: m/z 175 [M+H];

$^1$H NMR (400 MHz, CHLOROFORM-d) δ ppm 1.23-1.40 (2H, m), 1.59-1.78 (3H, m), 2.33 (3H, d, J=4.16 Hz), 2.82 (2H, dd, J=6.24, 3.79 Hz), 3.27-3.39 (2H, m), 3.88-4.02 (2H, m)

Step 4: Synthesis of Compound B-5

A solution of 90 g (516 mmol) of compound B-4 in toluene (500 mL) under nitrogen atmosphere is cooled in an ice-bath. A solution of sodium ethoxide in ethanol (21%, 231 mL) is added and the reaction stirred for 50 min. Then 76 mL (516 mmol) of ethyl α-bromoisobutyrate are added and the reaction stirred for 1 h. To the reaction mixture are added glacial acetic acid (8.9 mL) and water (500 mL). The organic layer is separated and washed with water (500 mL). A 3-neck round bottom flask is charged with water (500 mL), Oxone® (477 g, 775 mmol) and tetrabutylammonium-hydrogensulfate (5 g, 15 mmol) and the organic layer is added. The biphasic reaction mixture is stirred for 2 d at room temperature. The solids are removed by filtration and the layers of the filtrate are separated. The organic layer is washed with water (2×500 mL). The solvent is removed under reduced pressure and further azeotroped with toluene to give 125 g of compound B-5. Yield: 87%; ES-MS: m/z 279 [M+H]; $^1$H NMR (250 MHz, CHLOROFORM-d) δ ppm 1.32 (3H, t, J=7.16 Hz), 1.39-1.59 (2H, m), 1.64 (6H, s), 1.81-1.97 (2H, m), 2.29-2.53 (1H, m), 3.15 (2H, d, J=6.55 Hz), 3.45 (2H, dd, J=1.83, 0.30 Hz), 3.88-4.03 (2H, m), 4.26 (2H, d, J=7.16 Hz)

Step 5: Synthesis of Compound B-6

To a solution of 123 g (0.44 mol) of compound B-5 in THF (450 mL) are added 663 mL of 2M aqueous sodium hydroxide solution (1.33 mol). The reaction is stirred at room temperature for 1 h. To the reaction mixture is added TBME (1.25 L) and the layers are separated. The aqueous layer is cooled in an ice bath and then acidified with 37% aqueous HCl solution (123 mL). The resulting precipitate is isolated by filtration, washed with water (200 mL) and dried under reduced pressure at 50° C. to afford 101 g of 2 compound B-6 as white crystalline solids. Yield: 91%; ES-MS: m/z 251 [M+H]; $^1$H NMR (400 MHz, DMSO-d6) δ ppm 1.31-1.45 (2H, m), 1.49 (6H, s), 1.70-1.79 (2H, m), 2.13-2.28 (1H, m), 3.24 (2H, d, J=6.60 Hz), 3.28-3.38 (2H, m), 3.76-3.85 (2H, m), 13.65 (1H, br. s.)

Step 6: Synthesis of Compound B-7

Activation of 55.9 g (22.3 mmol) of compound B-6 is achieved by treatment with thionyl chloride (600 mL) at 60° C. for 3 h. The reaction mixture is cooled to room temperature and excess thionyl chloride is removed under reduced pressure.
The crude acid chloride is dissolved in DCM (400 mL) and added to a solution of 31.3 g (22.3 mmol) of 3-tert-Butyl-isoxazol-5-ylamine and N,N-diisopropylethylamine (194 mL) in DCM (250 mL). The reaction is stirred at room temperature for 16 h. The reaction mixture is diluted with DCM (1350 mL) and washed with saturated aqueous NaHCO$_3$ solution (1000 mL). The organic layer is dried over Na$_2$SO$_4$, filtered and the filtrate is concentrated under reduced pressure. The crude product is purified by dry-flash column chromatography (2 kg silica, eluent: DCM, 0-20% ethyl acetate). The resulting solid is recrystallised from isopropanol/heptanes (1/1. 2 L), then dried under reduced pressure to afford 80 g of compound B-7 as an off-white powder. Yield 96%; ES-MS: m/z 373 [M+H]; $^1$H NMR (360 MHz, CHLOROFORM-d) δ ppm 1.35 (9H, s), 1.41-1.55 (2H, m), 1.74 (6H, s), 1.82-1.91 (2H, m), 2.29-2.52 (1H, m), 2.92 (2H, d, J=6.58 Hz), 3.34-3.49 (2H, m), 3.88-4.00 (2H, m), 6.30 (1H, s), 9.38 (1H, s).

Step 7: Synthesis of Example 4

To a solution of 200 mg (0.54 mmol) of compound B-7 in anhydrous THF (2 mL) are added 41 mg (1.07 mmol) of lithium aluminium hydride in portions at 0° C. The reaction is allowed to warm to room temperature and stirred for 5 h. The reaction is quenched by addition of saturated NH$_4$Cl solution and the mixture is filtered through Celite®. The filtrate is concentrated under reduced pressure and the residue is purified by column chromatography (silica, eluent: DCM, 5% ethyl acetate) to yield 27 mg of (3-tert-butyl-isoxazol-5-yl)-[2-methyl-2-(tetrahydro-pyran-4-ylmethanesulfonyl)-propyl]-amine. Yield: 14%; ES-MS: m/z 359 [M+H]; $^1$H NMR (400 MHz, CHLOROFORM-d) δ ppm 1.27 (9H, s), 1.39-1.59 (8H, m), 1.81-1.99 (2H, m), 2.32-2.53 (1H, m), 2.79-2.90 (2H, m), 3.40-3.52 (2H, m), 3.54 (2H, d, J=6.36 Hz), 3.90-4.06 (2H, m), 4.94 (1H, s), 5.18 (1H, t, J=6.36 Hz);

Examples in table 4, Method B are synthesised according to this procedure

Method C

Synthesis of Example 6

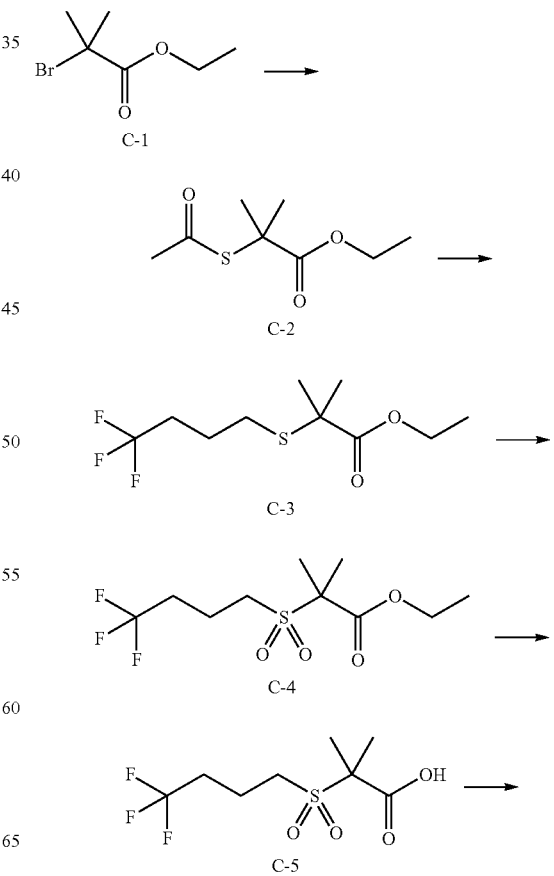

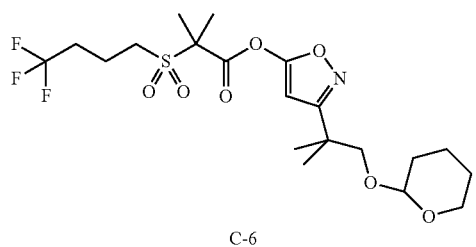

C-6

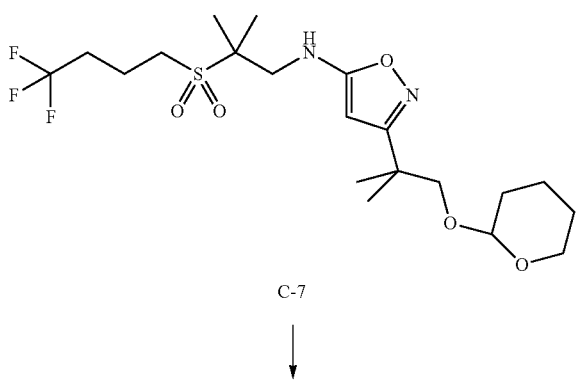

C-7

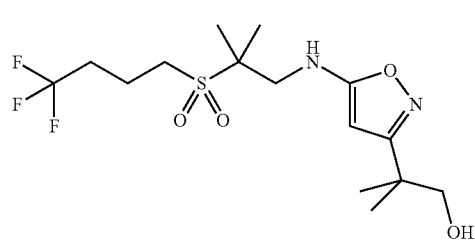

Example 6

Step 1: Synthesis of Compound C-2

To a solution of C-1 (62 g, 0.32 mol) in DMF (500 mL) at room temperature is added potassium thioacetate (72 g, 0.63 mol). The reaction is stirred for 16 h and then concentrated under reduced pressure. The residue is diluted with a 2M aqueous hydrochloric acid solution (500 mL) and extracted with ethyl acetate (3×500 mL). The organic fractions are combined, washed with brine (300 mL), dried over $MgSO_4$, filtered and concentrated under reduced pressure. Purification by chromatography (silica, eluent: heptanes/DCM) provides 44 g of compound C-2. Yield: 73%; m/z 191 [M+H]; $^1$H NMR (250 MHz, CHLOROFORM-d) δ ppm 1.18-1.30 (3H, m), 1.57 (6H, s), 2.27 (3H, s), 4.19 (2H, q, J=7.16 Hz).

Step 1: Synthesis of Compound C-3

To a solution of 149 g (785.4 mmol) of compound C-2 in ethanol (1.2 L, degassed under nitrogen for 1 h) are added 169.7 g (105 mmol) of sodium methoxide, followed by a solution of 150 g (785.4 mmol) of 1-bromo-4,4,4-trifluorobutane. The reaction is heated to 85° C. for 3 d. The solvent is removed under reduced pressure. The residue is dissolved in DCM (1 L) and washed with saturated aqueous $NaHCO_3$ solution (2×1 L). The organic layer is dried over $Na_2SO_4$, filtered and the filtrate is concentrated under reduced pressure to afford 171 g of compound C-3 as a brown oil. Yield: 84%; ES-MS: m/z 259 [M+H]; $^1$H NMR (500 MHz, CHLOROFORM-d) δ ppm 1.29 (3H, t, J=7.17 Hz), 1.51 (6H, s), 1.76-1.86 (2H, m), 2.12-2.27 (2H, m), 2.69 (2H, t, J=7.17 Hz), 4.18 (2H, q, J=7.17 Hz).

Step 2: Synthesis of Compound C-4

To a solution of 220 g (851.7 mmol) of compound C-3 in 1,4-dioxane/water (1/1, 4 L) are added 1047 g (1703.4 mmol) of Oxone® in portions over 0.5 h at room temperature. The reaction mixture is stirred at room temperature for 18 h. The solid is removed by filtration and rinsed with 1,4-dioxane (0.5 L). The filtrate is concentrated under reduced pressure to remove the organic solvent. The aqueous residue is extracted with DCM (2×1 L). The combined organic extracts are washed with saturated aqueous $NaHCO_3$ solution (2 L), dried over $Na_2SO_4$ and filtered. The filtrate is concentrated under reduced pressure to afford 226 g of compound C-3 as dark yellow oil. Yield 92%; ES-MS: m/z 291 [M+H]; $^1$H NMR (500 MHz, CHLOROFORM-d) δ ppm 1.32 (3H, t, J=7.17 Hz), 1.66 (6H, s), 2.20 (2H, quin, J=7.59 Hz), 2.28-2.41 (2H, m), 3.34 (2H, t, J=7.48 Hz), 4.27 (2H, q, J=7.17 Hz).

Step 3: Synthesis of Compound C-5

To a solution of 170 g (585.6 mmol) of compound C-4 in THF (3.4 L) are added 225.4 g (1756.8 mmol) of potassium trimethylsilanolate in portions over 0.5 h. The reaction is stirred at room temperature for 18 h. The reaction mixture is acidified with 2M aqueous HCl solution (2 L) to pH 2 and extracted with DCM (2×2 L). The combined organic extracts are dried ($Na_2SO_4$) and filtered. The filtrate is concentrated under reduced pressure to afford 143 g of compound C-5 as yellow solids. Yield: 93%; ES-MS: m/z 261 [M−H]. $^1$H NMR (500 MHz, CHLOROFORM-d) δ ppm 1.71 (6H, s), 2.18-2.28 (2H, m), 2.30-2.42 (2H, m), 3.38 (2H, t, J=7.48 Hz), 6.96 (1H, br. s.).

Step 4: Synthesis of Compound C-6

Activation of 72 g (0.27 mol) of compound C-5 as the corresponding acid chloride is achieved by treatment with thionyl chloride (50 mL, 0.55 mol) and DMF (cat., 10 mol %) in toluene (0.7 L) at 100° C. for 6 h. The reaction is cooled to room temperature and toluene (0.2 L) is removed by distillation, whilst adding fresh toluene (0.2 L). This process is repeated twice.

This acid chloride solution is added dropwise over 0.5 h to a stirred suspension of 56 g (0.23 mol) of 3-[1,1-dimethyl-2-(tetrahydro-pyran-2-yloxy)-ethyl]-isoxazol-5-ylamine and 92 mL (0.55 mol) of N,N-diisopropylethylamine in toluene (0.3 L) at 35° C. After complete addition the reaction is heated to 60° C. for 17 h. The reaction is cooled to room temperature and the solvent is removed under reduced pressure. The residue is dissolved in ethyl acetate (1 L) and washed with saturated aqueous $NaHCO_3$ solution (0.7 L), brine (0.7 L) dried ($Na_2SO_4$) and filtered. The filtrate is concentrated under reduced pressure and the residue purified twice by dry-flash column chromatography (silica, eluent heptanes, 30% ethyl acetate) to yield 85 g of compound C-6. Yield: 64%; ES-MS: m/z 483 [M−H]; $^1$H NMR (500 MHz, CHLOROFORM-d) δ ppm 1.36 (3H, s), 1.38 (3H, s) 1.45-1.73 (5H, m), 1.74-1.87 (7H, m), 2.15-2.25 (2H, m), 2.27-2.40 (2H, m), 3.11 (2H, t, J=7.55 Hz), 3.38 (1H, d, J=9.31 Hz), 3.46-3.53 (1H, m), 3.75-3.84 (2H, m), 4.59 (1H, t, J=3.43 Hz), 6.37 (1H, s), 9.24 (1H, s).

Step 5: Synthesis of Compound C-7

To a solution of 500 mg (1.03 mmol) of compound C-6 in anhydrous THF (5 mL) are added 4.126 mL (4.12 mmol) of lithium aluminium hydride (1M solution in THF) at 0° C. under nitrogen atmosphere. The reaction is allowed to warm to room temperature and stirred for 18 h. The reaction is quenched by addition of saturated ammonium chloride solution and the mixture is filtered through Celite®. The filtrate is concentrated under reduced pressure to afford a yellow oil which is purified by column chromatography (silica on Combiflash system, eluent: heptanes, 0-100% ethyl acetate) to afford 257 mg of compound C-7. Yield: 49%; ES-MS: m/z 469 [M−H]; $^1$H NMR (250 MHz, CHLOROFORM-d) δ ppm 1.20-1.35 (9H, m), 1.36-1.88 (9H, m), 2.13-2.48 (4H, m), 3.05 (2H, t, J=7.23 Hz), 3.34 (1H, d, J=9.44 Hz), 3.43-3.60 (3H, m), 3.71-3.88 (2H, m), 4.58 (1H, t, J=3.05 Hz), 5.03 (1H, s), 5.15 (1H, t, J=6.47 Hz).

Step 6: Synthesis of Example 6

A solution of 257 mg (0.55 mmol) of compound C-7 in DCM/ethanol (1/1, 6 mL) are added 498 mg (1.64 mmol) of MP-TsOH resin (loading 3.3 mmol/g) and the reaction is shaken on an orbital shaker at room temperature for 18 h. The resin is removed by filtration and washed with DCM (10 mL) and methanol (10 mL). The combined filtrates are concentrated under reduced pressure and the residue is purified by column chromatography (silica on CombiFlash system, eluent: heptanes, 0-100% ethyl acetate) to yield 118 mg of example 6. Yield 56%; ES-MS: m/z 387 [M+H]: $^1$H NMR (250 MHz, CHLOROFORM-d) δ ppm 1.24 (6H, s), 1.46 (6H, s), 2.12-2.27 (2H, m), 2.29-2.43 (3H, m), 3.04 (2H, t, J=7.31 Hz), 3.55 (2H, d, J=6.24 Hz), 3.61 (2H, s), 4.96 (1H, s), 5.32-5.46 (1H, m).

Examples in table 4, Method C are synthesised according to this procedure

Method D

Synthesis of Example 5

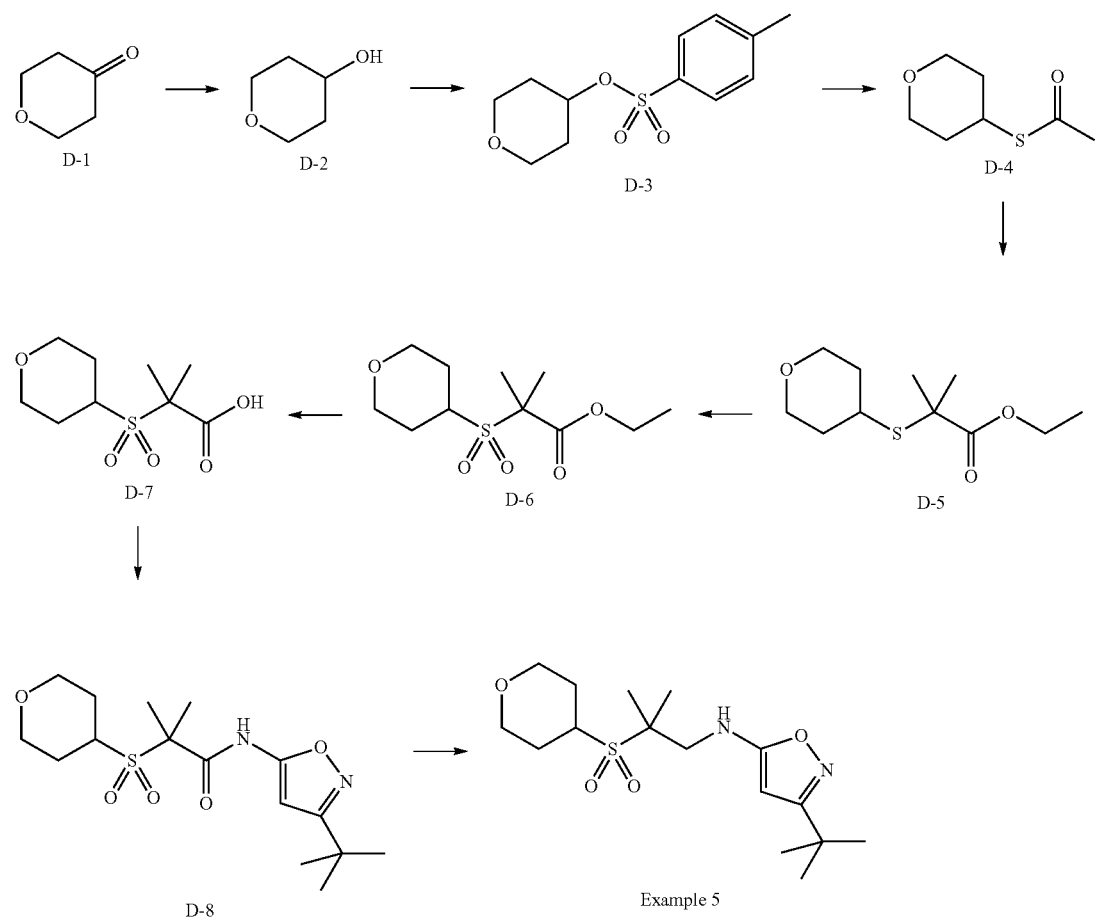

Step 1: Synthesis of Compound D-2

To a solution of 75 g (0.75 mol) of compound D-1 in THF (150 mL) is added a suspension of 28.4 g (0.75 mol) LiAlH$_4$ in THF (600 mL) under nitrogen atmosphere maintaining the temperature below 30° C. with the aid of an ice-bath. Then the reaction is allowed to warm to room temperature and stirred for 5 h. The reaction is quenched by addition of saturated aqueous NH$_4$Cl solution until effervescence ceased. The resulting precipitate is removed by filtration through Celite® and washed with THF (150 mL). The filtrate is concentrated under reduced pressure to afford 71.1 g of compound D-2 as a pale yellow oil. Yield: 92%, $^1$H NMR (500 MHz, CHLOROFORM-d) δ ppm 1.54 (2H, m), 1.81-1.92 (2H, m), 2.11 (1H, br. s.), 3.38-3.47 (2H, m), 3.83 (1H, tt, J=9.10, 4.38 Hz), 3.94 (2H, dt, J=11.88, 4.15 Hz).

Step 2: Synthesis of Compound D-3

To a solution of 133 g (1.31 mol) of compound D-2 in pyridine (1.5 L) are added 373 g (1.95 mol) of p-toluenesulfonylchloride portionwise at 10° C. After complete addition the reaction is allowed to warm to room temperature and stirred for 18 h. The reaction is poured onto a stirred mixture of aqueous HCl/ice. The resulting precipitate is isolated by filtration and dissolved in DCM (1 L). The organic layer is washed with 1M aqueous HCl solution (1 L), followed by saturated aqueous NaHCO$_3$ solution (1 L) and is then dried over Na$_2$SO$_4$. Filtration and concentration of the filtrate under reduced pressure gives 300 g of compound D-3 as an orange oil. Yield: 90%, ES-MS: m/z: 257 [M+H], 279 [M+Na]. $^1$H-NMR (250 MHz, CHLOROFORM-d) δ ppm 1.66-1.96 (4H, m), 2.45 (3H, s), 3.47 (2H, ddd, J=11.76, 8.19, 3.50 Hz), 3.79-3.95 (2H, m), 4.69 (1H, tt, J=8.13, 4.13 Hz), 7.35 (2H, d, J=8.07 Hz), 7.76-7.87 (2H, m)

Step 3: Synthesis of Compound D-4

To a solution of 300 g (1.175 mol) of compound D-3 in DMF (3 L) are added 268 g (2.35 mol) potassium thioacetate, followed by a catalytic amount of NaI (0.12 g, 10 mol %) at room temperature. After complete addition, the reaction is heated to 50° C. for 20 h. The reaction mixture is partitioned between TBME (3 L) and water (3 L), the aqueous layer is extracted with TBME (2 L), then saturated with NaCl and extracted again with TBME (2×2 L). The combined organic extracts are dried over Na$_2$SO$_4$, filtered and the solvent is removed under reduced pressure to afford 153 g of compound D-4. Yield: 81%; ES-MS: m/z 161 [M+H]; $^1$H-NMR (250 MHz, CHLOROFORM-d) δ ppm 1.47-1.98 (4H, m), 2.30 (3H, s), 3.41-3.74 (3H, m), 3.88 (2H, dt, J=11.76, 3.86 Hz)

Step 4: Synthesis of Compound D-5

A solution of 153 g (0.96 mol) of compound D-4 in ethanol (3.5 L) is degassed with nitrogen over 0.5 h and 125 g (2.23 mol) of KOH are added. Then a solution of 250 mL (1.68 mol) of ethyl α-bromoisobutyrate in EtOH (1 L) are added over 0.5 h, during which the temperature is increased to 40° C. The reaction is stirred for 18 h at room temperature under a nitrogen atmosphere. The reaction mixture is filtered, the solid is washed with ethanol (0.5 L) and the filtrate is concentrated under reduced pressure. The crude material is dryloaded onto silica and purified by dry-flash column chromatography (silica, eluent: n-heptanes, 2-10% ethyl acetate) to afford 158 g of compound D-5 as an orange-brown oil. Yield: 71%; ES-MS: m/z 233 [M+H]; $^1$H-NMR (500 MHz, CHLOROFORM-d) δ ppm 1.28 (3H, t, J=7.17 Hz), 1.52 (6H, s), 1.56-1.67 (2H, m), 1.85 (2H, dt, J=13.35, 1.64 Hz), 3.04 (1H, tt, J=10.60, 4.20 Hz), 3.40-3.49 (2H, m), 3.88 (2H, dt, J=11.75, 3.81 Hz), 4.14-4.20 (2H, m)

Step 5: Synthesis of Compound D-6

To a solution of 158 g (0.68 mol) of compound D-5 in 1,4-dioxane/water (4/1, 1.6 L) are added 835 g (1.35 mol) of Oxone® in portions over 50 min. The reaction mixture is stirred at room temperature for 18 h. The solid is removed by filtration and washed with 1,4-dioxane (1 L). The combined filtrates are concentrated under reduced pressure. The residue is dissolved in ethyl acetate (1.5 L) and washed with water (1 L). The organic layer is dried over Na$_2$SO$_4$, filtered and the solvent is removed under reduced pressure to afford 166 g of compound D-6 as a yellow oil. Yield: 92%, ES-MS: m/z 265 [M+H], 287 [M+Na]; $^1$H-NMR (250 MHz, CHLOROFORM-d) δ ppm 1.30 (3H, t, J=7.08 Hz), 1.65 (6H, s), 1.89-2.10 (4H, m), 3.34-3.51 (2H, m), 3.72-3.90 (1H, m), 4.06 (2H, dt, J=11.69, 3.60 Hz), 4.24 (2H, q, J=7.16 Hz)

Step 6: Synthesis of Compound D-7

To a solution of 166 g (0.63 mol) of compound D-6 in THF/water (4/1, 1.66 L) are added 50.5 g (1.26 mol) of NaOH pellets in portions over 20 min. The reaction is stirred at room temperature for 2.5 d. The organic solvent is removed under reduced pressure and the aqueous residue is diluted with water (2 L) and washed with DCM (2 L). The aqueous layer is acidified to pH 1-2 with concentrated HCl and then extracted with DCM (3×2 L). The acidic aqueous is further saturated with NaCl and extracted again with DCM (6×2 L). The combined organic extracts are concentrated under reduced pressure to give 123 g of compound D-7 as a white solid. Yield: 83%, ES-MS: m/z 235 [M−H]; $^1$H-NMR (500 MHz, CHLOROFORM-d) δ ppm 1.71 (6H, s), 1.94-2.12 (4H, m), 3.47 (2H, td, J=11.41, 2.98 Hz), 3.73-3.86 (1H, m), 4.07-4.15 (2H, m), 6.82 (1H, br. s.)

Step 7: Synthesis of Compound D-8

Activation of 60 g (0.25 mol) of compound D-7 as the corresponding acid chloride is achieved by treatment with thionyl chloride (0.9 L, 12.39 mol) at 60° C. for 1.5 h. The reaction is cooled to room temperature and acid chloride mixture was evaporated to dryness. The acid chloride mixture is dissolved in DCM (200 mL).

This acid chloride solution is added dropwise over 20 mins to a stirred suspension of 36 g (0.25 mol) of 3-tert-butyl-isoxazol-5-ylamine and 0.6 L (0.50 mol) of N,N-diisopropylethylamine in DCM (400 mL) at 35° C. After complete addition the reaction is stirred at room temperature for 17 h. The solvent is removed under reduced pressure. The residue is purified by dry-flash column chromatography (silica, eluent heptanes, 20% ethyl acetate) to yield 50 g of light brown solid. Solid is re-crystallized from (50% IPA in heptane) to afford 34 g of compound D-8 Yield: 43%; ES-MS: m/z 359 [M+H];

$^1$H-NMR (400 MHz, CHLOROFORM-d) δ ppm 1.33 (9H, s), 1.76 (6H, s), 1.83-1.91 (2H, m), 1.92-2.05 (2H, m), 3.34-3.51 (3H, m), 4.07 (2H, ddd, J=11.86, 2.20, 2.08 Hz), 6.27 (1H, s), 9.60 (1H, s)

Step 8: Synthesis of Example 5

To a solution of 100 mg (0.42 mmol) of compound D-8 in anhydrous THF (1 mL) is added 2 mL (4.78 mmol) of 1M solution $BH_3$ in THF at room temperature. The reaction is stirred for 4.5 h. The reaction mixture is quenched by addition of MeOH. The solvent is removed under reduced pressure. The residue is dissolved in DCM, washed with saturated solution of sodium bicarbonate and brine, dried ($Na_2SO_4$) and filtered. The filtrate is concentrated under reduced pressure and the resulting residue is purified by column chromatography (silica on Biotage system, eluent: DCM, ethyl acetate 10%) to afford 67 mg of example 5. Yield: 47%; ES-MS: m/z 345 [M+H]. $^1$H-NMR (400 MHz, CHLOROFORM-d) δ ppm 1.28 (9H, s), 1.49 (6H, s), 1.85-2.19 (4H, m), 3.27-3.51 (3H, m), 3.56 (2H, d, J=6.36 Hz), 4.03-4.23 (2H, m), 4.93 (1H, s), 5.25 (1H, s)

Examples in table 4, Method D are synthesised according to this procedure

Method E

Synthesis of Example 7

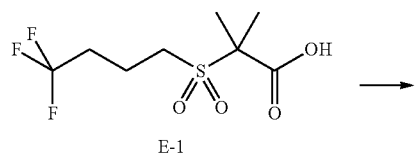

E-1

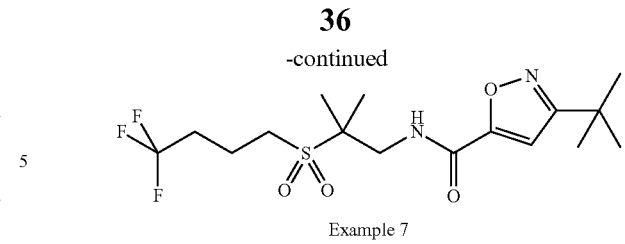

Example 7

Step 1: Synthesis of Compound E-2

Activation of 1 g (3.8 mmol) of compound E-1 (prepared according to Method C, step 1-3) as the corresponding acid chloride is achieved by treatment with oxalyl chloride (0.39 mL, to 4.6 mmol) and DMF (1 drop) in DCM (20 mL) at room temperature for 18 h. The reaction is concentrated under reduced pressure. The crude acid chloride is dissolved in DCM (20 mL) and added dropwise to a solution of aqueous ammonia (30 wt %, 10 mL) at 0° C. The reaction is stirred at room temperature for 16 h. The layers are separated and the aqueous phase is extracted with DCM (3×20 mL). The combined organic extracts are dried ($MgSO_4$), filtered and the filtrate is concentrated under reduced pressure to give 1.01 g of compound E-2. Yield 87%, ES-MS: m/z 262 [M+H], $^1$H NMR (500 MHz, CHLOROFORM-d) δ ppm 1.68 (s, 6H), 2.11-2.26 (m, 2H), 2.27-2.41 (m, 2H), 3.16 (t, J=7.57 Hz, 2H), 5.63 (br. s., 1H), 6.64 (br. s., 1H).

According to the above procedure the following amines are made

TABLE 2

| Structure | $^1$H-NMR | Yield [%] | m/z [M + H] |
|---|---|---|---|
| ![structure] | (500 MHz, CHLOROFORM-d) δ ppm 1.68 (s, 6 H), 2.11-2.26 (m, 2 H), 2.27-2.41 (m, 2 H), 3.16 (t, J = 7.57 Hz, 2 H), 5.63 (br. s., 1 H), 6.64 (br. s., 1 H) | 87 | 262 |
| ![structure] | (500 MHz, (CHLOROFORM-d) δ ppm 1.68 (s, 6 H), 1.92-2.10 (m, 4 H), 3.34-3.46 (m, 2 H), 3.46-3.58 (m, 1 H), 4.03-4.13 (m, 2 H), 5.57 (br. s., 1 H), 6.91 (br. s., 1 H) | 83 | 258 [M + Na] |

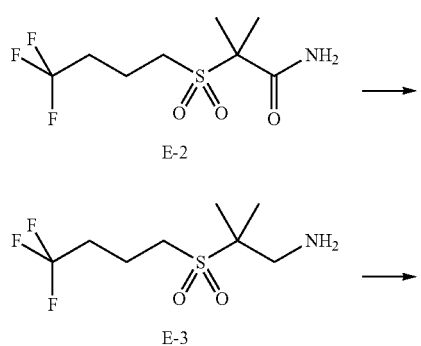

E-2

E-3

Step 2: Synthesis of Compound E-3

To a suspension of 252 mg (6.7 mmol) of lithium aluminium hydride in anhydrous THF (10 mL) is added a solution of 1.01 g (3.9 mmol) of compound E-2 in anhydrous THF (10 mL) at 0° C. The resulting mixture is allowed to warm to room temperature and stirred for 18 h. Additional lithium aluminium hydride (12 mL, 1M solution in THF) is added and the mixture is heated at 50° C. for 3 h. The reaction is quenched by addition of saturated aqueous $NH_4Cl$ solution. The resulting precipitate is removed by filtration and washed with THF. The filtrate is concentrated under reduced pressure and the residue is purified by column chromatography (silica, eluent: ethyl acetate/heptanes) to give 597 mg of compound E-3. Yield: 73%, ES-MS: m/z 248 [M+H], $^1$H NMR (500 MHz, CHLOROFORM-d) δ ppm 1.40 (s, 6H), 2.13-2.26 (m, 2H), 2.27-2.41 (m, 2H), 3.06 (s, 2H), 3.17-3.25 (m, 2H).

According to the above procedure the following amines are made with the following modification to be noted: compound E-4 is purified by chromatography (silica, eluent: DCM/methanol).

TABLE 3

| compound | Structure | ¹H-NMR | Yield [%] | m/z [M + H] |
|---|---|---|---|---|
| E-3 | 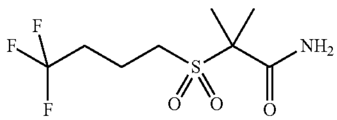 [SMILES: CC(C)(C(N)=O)S(=O)(=O)CCCC(F)(F)F] | (500 MHz, CHLOROFORM-d) δ ppm 1.40 (s, 6 H), 2.13-2.26 (m, 2 H), 2.27-2.41 (m, 2 H), 3.06 (s, 2 H), 3.17-3.25 (m, 2 H) | 73 | 248 |
| E-4 | 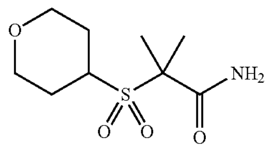 | (500 MHz, CHLOROFORM-d) δ ppm 1.39-1.43 (m, 6 H), 1.89-2.11 (m, 4 H), 3.05 (s, 2 H), 3.37-3.48 (m, 2 H), 3.55-3.66 (m, 1H), 4.05-4.14 (m, 2 H) | 26 | 222 |

Step 3: Synthesis of Example 7

Activation of 68 mg (0.4 mmol) of 3-tert-butyl-isoxazole-5-carboxylic acid as the corresponding acid chloride is achieved by treatment with oxalyl chloride (0.0.07 mL, 0.8 to mmol) and DMF (1 drop) at room temperature for 18 h. The reaction is concentrated under reduced pressure. The crude acid chloride is dissolved in THF (5 mL) and is added to a solution of 100 mg (0.4 mmol) of compound E-3 and N,N-diisopropylethylamine (0.2 mL, 1.2 mmol) in THF (10 mL). The reaction is stirred at room temperature for 16 h. The reaction mixture is concentrated under reduced pressure. The residue is purified by column chromatography (silica, eluent: ethyl acetate/heptanes) followed by trituration with heptanes to give 23 mg of example 7. Yield: 14%; ES-MS: m/z 399 [M+H]; ¹H NMR (500 MHz, CHLOROFORM-d) δ ppm 1.33-1.39 (9H, m), 1.47 (6H, s), 2.24 (2H, quin, J=7.49 Hz), 2.32-2.43 (2H, m), 3.06 (2H, t, J=7.49 Hz), 3.85 (2H, d, J=6.31 Hz), 6.84 (1H, s), 7.37 (1H, t, J=5.99 Hz)

Examples in table 4, Method E are synthesised according to this procedure

Method F

Synthesis of Example 10

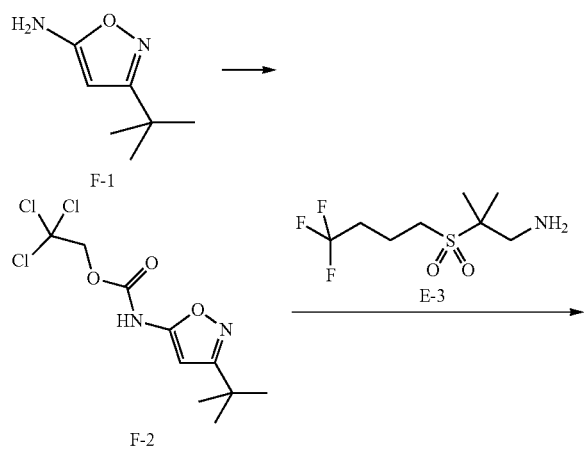

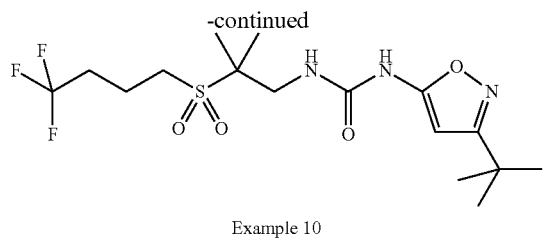

Example 10

Step 1: Synthesis of Compound F-2

Trichloroethyl chloroformate (1.1 mL, 8.6 mmol) is added to a mixture of 1 g (7.1 mmol) of compound F-1 and 1.8 g (21.4 mmol) of sodium hydrogen carbonate in ethyl acetate/water (1/1, 20 mL) at room temperature. The resulting mixture is vigorously stirred for 3 d and then additional trichloroethyl chloroformate (1.1 mL, 8.6 mmol) and sodium hydrogen carbonate (1.8 g, 21.4 mmol) are added. The mixture is stirred for a further 3 h. The aqueous layer is separated and extracted with ethyl acetate (2×25 mL). The organic layers are combined, dried over MgSO₄, filtered and the filtrate is concentrated under reduced pressure. The residue is purified by column chromatography (silica, eluent: ethyl acetate/heptanes) followed by trituration with heptanes to give 397 mg of compound F-2. Yield: 18%; ES-MS: m/z 315 [M+H]; ¹H NMR (250 MHz, CHLOROFORM-d) δ ppm 1.33 (s, 9H) 4.86 (s, 2H) 6.11 (s, 1H) 7.68 (br. s., 1H)

Synthesis of Example 10

To a solution of 83 mg (0.4 mmol) of compound E-3 and 0.14 mL (0.81 mmol) of N,N-diisopropylethylamine in 1,1-dichloroethane (2 mL) are added 111 mg (0.35 mmol) of compound F-2 and the resulting solution is stirred at 80° C. for 2 h. The solvent is removed under reduced pressure. The residue is purified by column chromatography (silica, eluent: ethyl acetate/heptanes) to give 45 mg of example 10. Yield: 27%; ES-MS: m/z 414 [M+H], ¹H NMR (500 MHz, CHLOROFORM-d) δ ppm 1.32 (9H, s), 1.48 (6H, s), 2.16-2.28 (2H, m), 2.29-2.43 (2H, m), 3.07 (2H, t, J=7.49 Hz), 3.74 (2H, d, J=6.15 Hz), 5.99 (1H, s), 6.18 (1H, t, J=5.36 Hz), 8.18 (1H, br. s.)

Examples in table 4, Method F are synthesised according to this procedure

Method G

Synthesis of Example 11

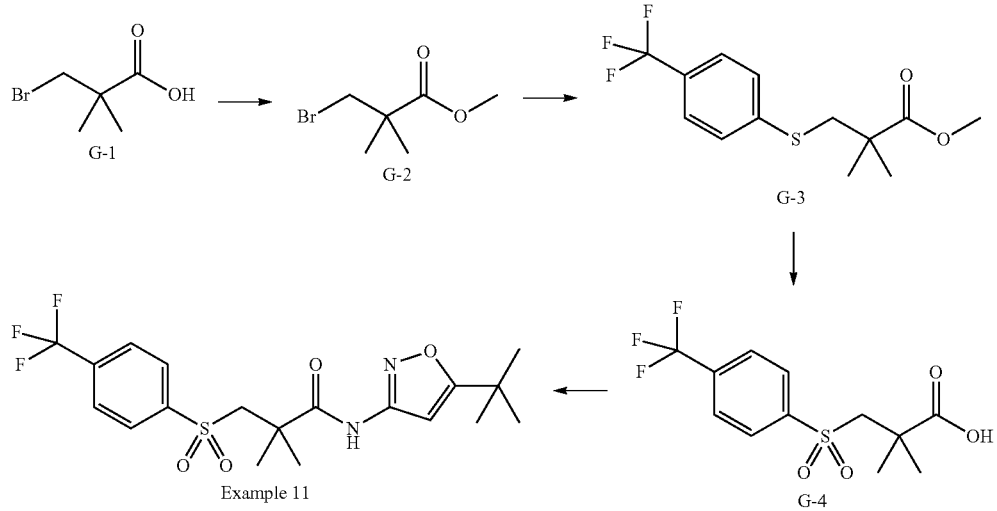

Step 1: Synthesis of Compound G-2

To a solution of compound G-1 (2 g, 11.1 mmol) in toluene/methanol (4/1, 20 mL) at 0° C. is added (trimethylsilyl)diazomethane (2 M in diethyl ether, 11 mL, 22.1 mmol) slowly under nitrogen atmosphere. The reaction is allowed to warm to room temperature to afford 1.78 g of compound G-2. Yield: 84%; 1H-NMR (400 MHz, CHLOROFORM-d) δ ppm 1.23 (6H, s), 3.41 (2H, s), 3.62 (3H, s).

Step 2: Synthesis of Compound G-3

To a solution of 4-trifluoromethylbenzene thiol (1.0 g, 5.6 mmol) in ethanol (15 mL) are added potassium hydroxide pellets (0.31 g, 5.6 mmol), followed by compound G-2 (1.1 g, 5.6 mmol). The reaction is heated to 80° C. for 16 h. The reaction is cooled to room temperature and the solid is removed by filtration. The filtrate is concentrated under reduced pressure. The residue is dissolved in DCM and washed with water, then brine. The organic layer is dried over $Na_2SO_4$, filtered and the filtrate is concentrated under reduced pressure to afford 1.4 g of compound G-3, which is used in the next step without further purification. Yield: 87%. m/z 293 [M+H]

Step 3: Synthesis of Compound G-4

To a solution of compound G-3 (1.4 g, 4.8 mmol) in dioxane/water (4/1, 30 mL) is added Oxone® (8.8 g, 14.4 mmol) portionwise. The reaction mixture is stirred at room temperature for 16 h.

The reaction is filtered and the solids are washed with dioxane. The filtrate is concentrated under reduced pressure and the residue is dissolved in ethyl acetate and washed with brine, dried over $Na_2SO_4$ and filtered. The filtrate is concentrated under reduced pressure. The residue is dissolved in THF/water (4/1, 30 mL) and lithium hydroxide monohydrate (0.4 g, 9.6 mmol) is added. The reaction mixture is stirred at room temperature for 16 h, then concentrated under reduced pressure to remove the organic solvent. The aqueous residue is diluted with water, washed with ethyl acetate, then acidified with 2M aqueous HCl solution to pH 2. The acidic aqueous layer is extracted with ethyl acetate (2×30 mL). The combined organic extracts are washed with brine, dried over $Na_2SO_4$, filtered and the filtrate is concentrated under reduced pressure to afford 1.19 g of compound G-4. Yield: 89%; 1H-NMR (400 MHz, CHLOROFORM-d) δ ppm 1.48 (6H, s), 3.52 (2H, s), 7.83 (2H, d, J=8.4 Hz), 8.04 (2H, d, J=8.6 Hz)

Step 4: Synthesis of Example 11

Activation of 100 mg (0.36 mmol) of compound G-4 as its acid chloride is achieved by treatment with thionyl chloride (27 mL) at 70° C. for 3 h. The reaction mixture is cooled to room temperature and excess thionyl chloride is removed under reduced pressure.

The crude acid chloride is dissolved in DCM (3 mL) and added to a solution of 50 mg (0.36 mmol) of 5-tert-butyl-isoxazol-3-ylamine and N,N-diisopropylethylamine (62 µL, 0.36 mmol) in DCM (150 mL). The reaction is stirred at room temperature for 16 h. The reaction mixture is diluted with DCM (3 mL) and washed with saturated aqueous $NaHCO_3$ solution (3 mL). The organic layer is separated and washed with brine (3 mL), dried over $Na_2SO_4$, filtered and the filtrate is concentrated under reduced pressure. The crude product is purified by column chromatography (silica, eluent: DCM, 5% ethyl acetate) to afford 71 mg of example 11. Yield 45%; ES-MS: m/z 433 [M+H]; 1H-NMR (400 MHz, CHLOROFORM-d) δ ppm 1.26 (9H, s), 1.52 (6H, s), 3.53 (2H, s), 6.54 (1H, s), 7.72 (2H, d, J=8.23 Hz), 7.99 (2H, d, J=8.23 Hz), 8.81 (1H, s)

Method H

Synthesis of Example 15

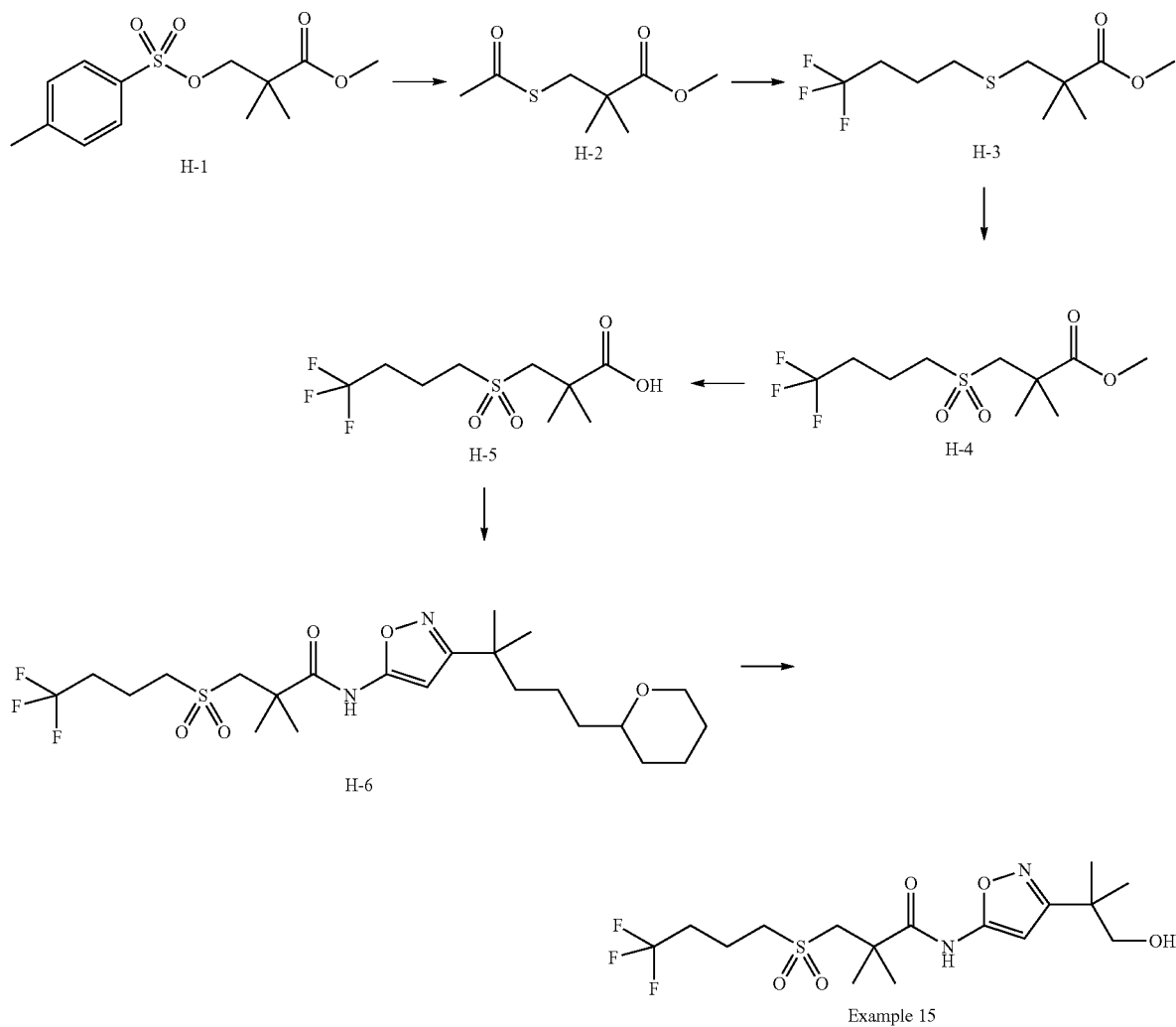

Step 1: Synthesis of Compound H-2

Compound H-2 is prepared by adaptation of methods described in the following reference: WO2008/039645, Boehringer Ingelheim Pharma International GMBH To a solution of compound H-1 (2.66 g, 7.43 mmol) in DMF (15 mL) are added slowly sodium iodide (0.111 g, 0.74 mmol) and potassium thioacetate (1.70 g, 14.86 mmol). The reaction is heated to 50° C. for 18 h. the solvent is removed under reduced pressure. The residue is dissolved in TBME (50 mL) and washed with water (2×10 mL), brine (10 mL), dried over $Na_2SO_4$ and filtered. The filtrate is concentrated under reduced pressure to afford quantitatively compound H-2, which is used in the next step without further purification.

$^1H$ NMR (250 MHz, CHLOROFORM-d) δ ppm 1.22 (6H, s), 2.33 (3H, s), 3.13 (2H, s), 3.67 (3H, s)

Step 2: Synthesis of Compound H-3

To a solution of compound H-2 (1.4 g, 7.36 mmol) in ethanol (23 mL, degassed) under nitrogen atmosphere is added sodium methoxide (1.59 g, 29.43 mmol). The mixture is stirred for 10 min at room temperature, then 1-bromo-4,4,4-trifluorobutane (1.41 g, 7.36 mmol) is added and the mixture is heated in a microwave to 100° C. for 30 min, then concentrated under reduced pressure. The residue is dissolved in ethyl acetate and washed with saturated sodium bicarbonate solution (2×5 mL), 1M aqueous HCl solution (2×5 mL) and brine. The organic layer is dried over $Na_2SO_4$, filtered and the filtrate is concentrated under reduced pressure. The residue is purified by column chromatography (silica, eluent; heptanes, 20% ethyl acetate) to afford 1.45 g of compound H-3. Yield: 76%; m/z 259 [M+H];

According to the above procedure the following intermediates are synthesised

| Structure | ¹H-NMR | Yield [%] | m/z [M + H] |
|---|---|---|---|
| 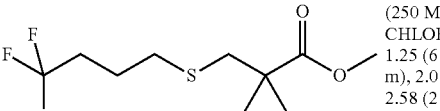 | (250 MHz, CHLOROFORM-d) δ ppm 1.25 (6 H, s), 1.78-1.92 (2 H, m), 2.08-2.30 (2 H, m), 2.58 (2 H, t, J = 7.08 Hz), 2.73 (2 H, s), 3.69 (3 H, s) | 76 | 259 |
| 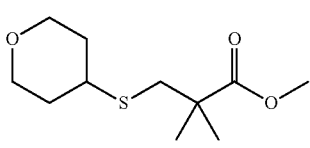 | (500 MHz, CHLOROFORM-d) δ ppm 1.26 (6 H, s), 1.55-1.65 (2 H, m), 1.89 (2 H, d, J = 12.93 Hz), 2.76 (2 H, s), 2.80 (1 H, tt, J = 10.76, 3.98 Hz), 3.41 (2 H, td, J = 11.27, 2.21 Hz), 3.69 (3 H, s), 3.96 (2 H, dt, J = 11.70, 3.61 Hz) | 53[#] | 233 |

[#]Toluene-4-sulfonic acid tetrahydro-pyran-4-yl ester is used as alkylating reagent.

Step 3: Synthesis of Compound H-4

To a solution of compound H-3 (1.45 g, 5.61 mmol) in dioxane/water (1/1, 40 mL) is added Oxone® (6.9 g, 11.2 mmol) over 5 min. The reaction mixture is stirred at room temperature for 2.5 h. the solid is removed by filtration and washed with dioxane. The filtrate is concentrated under reduced pressure to remove the organic solvent. The aqueous residue is partitioned between DCM (50 mL) and saturated aqueous NaHCO₃ solution (2×20 mL). the organic layer is dried over MgSO₄, filtered and the filtrate is concentrated under reduced pressure to afford 1.52 g of compound H-4. Yield; 94%; m/z 291 [M+H]. According to the above procedure the following intermediates are synthesised

Step 4: Synthesis of Compound H-5

To a solution of compound H-4 (1.54 g, 5.31 mmol) in THF/water (1/1, 40 mL) is added lithium hydroxide (0.44 g, 18.33 mmol). The reaction mixture is stirred at room temperature for 16 h. The filtrate is concentrated under reduced pressure to remove the organic solvent. The aqueous residue is washed with diethyl ether (50 mL) and then acidified with 6N aqueous HCl solution. The acidic aqueous layer is extracted with ethyl acetate (3×50 mL). The combined organic extracts are dried over MgSO₄, filtered and the filtrate is concentrated under reduced pressure to afford 1.26 g of compound H-5. Yield: 86%; m/z 275 [M−H];

According to the above procedure the following intermediates are synthesised:

| Structure | ¹H-NMR | Yield [%] | m/z [M + H] |
|---|---|---|---|
| 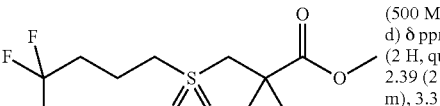 | (500 MHz, CHLOROFORM-d) δ ppm 1.45 (6 H, s), 2.15 (2 H, quin, J = 7.63 Hz), 2.27-2.39 (2 H, m), 3.05-3.10 (2 H, m), 3.36 (2 H, s), 3.76 (3 H, s) | 94 | 291 |
| 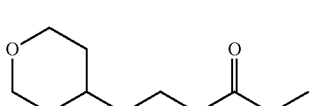 | (500 MHz, CHLOROFORM-d) δ ppm 1.45 (6 H, s), 1.86-1.96 (2 H, m), 2.03 (2 H, dd, J = 12.93, 1.58 Hz), 3.06 (1 H, tt, J = 12.02, 3.82 Hz), 3.29 (2 H, s), 3.40 (2 H, td, J = 11.86, 1.81 Hz), 3.75 (3 H, s), 4.13 (2 H, dd, J = 11.51, 4.26 Hz) | 64 | 265 |

| Structure | ¹H-NMR | Yield [%] | m/z [M − H] |
|---|---|---|---|
| 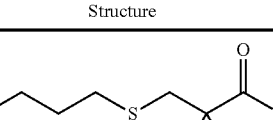 | (500 MHz, CHLOROFORM-d) δ ppm 1.49 (6 H, s), 2.12-2.20 (2 H, m), 2.27-2.39 (2 H, m), 3.07-3.13 (2 H, m), 3.38 (2 H, s). | 86 | 275 |
| 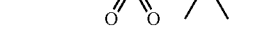 | (500 MHz, CHLOROFORM-d) δ ppm 1.50 (6 H, s), 1.87-1.97 (2 H, m), 2.00-2.07 (2 H, m), 3.08 (1 H, tt, J = 12.00, 3.92 Hz), 3.30 (2 H, s), 3.41 (2 H, td, J = 11.86, 1.66 Hz), 4.14 (2 H, dd, J = 11.51, 4.10 Hz) | 77 | 249 |

Step 5: Synthesis of Compound H-6

Activation of 200 mg (0.72 mmol) of compound H-5 as the corresponding acid chloride is achieved by treatment with oxalyl chloride (0.12 mL, 1.45 mmol) and DMF (cat., 10 mol %) in DCM (1 mL) at room temperature for 4 h. The reaction is concentrated under reduced pressure and the residue is taken up into THF (1 mL).

This acid chloride solution is added dropwise to a stirred solution of 174 mg (0.72 mmol) of 3-[1,1-dimethyl-2-(tetrahydro-pyran-2-yloxy)-ethyl]-isoxazol-5-ylamine and 0.38 mL (2.17 mmol) of N,N-diisopropylethylamine in THF (1 mL). The reaction is stirred at room temperature for 17 h. The solvent is removed under reduced pressure. The residue is purified by preparative HPLC (neutral method) to yield 144 mg of compound H-6.

Step 6: Synthesis of Example 15

A solution of 144 mg of compound H-6 in DCM/methanol (1/1, 2 mL) is treated with MP-TsOH resin (292 mg, loading 3.3 mmol/g) and the reaction is shaken on an orbital shaker at room temperature for 18 h. The resin is removed by filtration and washed with DCM/methanol (1/1, 10 mL). The combined filtrates are concentrated under reduced pressure and the residue is purified by column chromatography (silica, eluent: heptanes, 0-50% ethyl acetate) to afford 31 mg of example 15 as a white solid.

Examples in Table 6, Method H are synthesised according to this procedure with the following modification to be noted; for BI00667931, BI00667934, BI00667930 and BI00667889 step 6 is not required.

EXAMPLES

TABLE 4

| Example | Structure | ¹H-NMR | Method | m/z [M + H] |
|---|---|---|---|---|
| 1 | 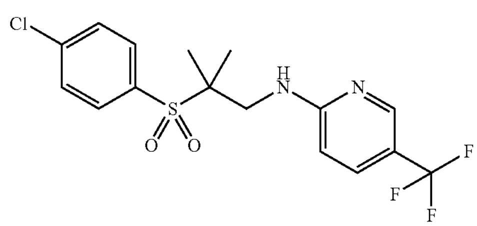 [SMILES: CC(C)(CNc1ccc(C(F)(F)F)cn1)S(=O)(=O)c1ccc(Cl)cc1] | (400 MHz, CHLOROFORM-d) δ ppm 1.35 (6 H, s), 3.86 (2 H, d, J = 6.04 Hz), 5.81 (1 H, br. s.), 6.53 (1 H, d, J = 8.78 Hz), 7.44-7.69 (3 H, m), 7.82 (2 H, d, J = 8.23 Hz), 8.30 (1 H, s) | A | 407/409 |
| 2 | 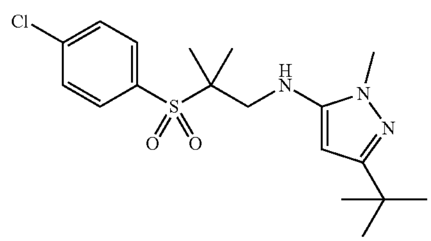 [SMILES: Cn1nc(C(C)(C)C)cc1NCC(C)(C)S(=O)(=O)c1ccc(Cl)cc1] | (400 MHz, CHLOROFORM-d) δ ppm 1.27 (9 H, s), 1.39 (6 H, s), 3.29 (2 H, d, J = 6.22 Hz), 3.63 (3 H, s), 4.35 (1 H, t, J = 5.95 Hz), 5.27 (1 H, s), 7.57 (2 H, d, J = 8.05 Hz), 7.81 (2 H, d, J = 8.23 Hz) | A | 398/400 |

TABLE 4-continued

| Example | Structure | ¹H-NMR | Method | m/z [M + H] |
|---|---|---|---|---|
| 3 | 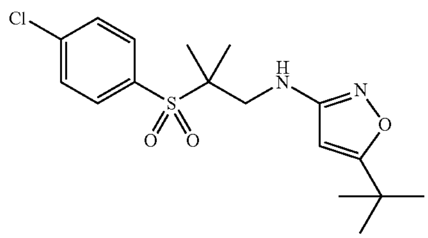 [SMILES: CC(C)(C)c1cc(NCC(C)(C)S(=O)(=O)c2ccc(Cl)cc2)no1] | (400 MHz, CHLOROFORM-d) δ ppm 1.31 (9 H, s), 1.36 (6 H, s), 3.50 (2 H, d, J = 6.11 Hz), 4.80 (1 H, t, J = 5.99 Hz), 5.50 (1 H, s), 7.49-7.63 (2 H, m), 7.73-7.89 (2 H, m) | A | 385/387 |
| 4 | 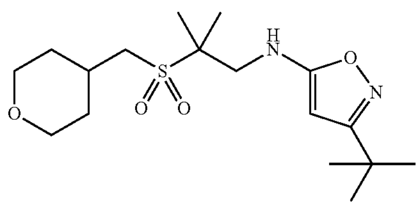 [SMILES: CC(C)(C)c1cc(NCC(C)(C)S(=O)(=O)CC2CCOCC2)on1] | (400 MHz, CHLOROFORM-d) δ ppm 1.27 (9 H, s), 1.39-1.59 (8 H, m), 1.81-1.99 (2 H, m), 2.32-2.53 (1 H, m), 2.79-2.90 (2 H, m), 3.40-3.52 (2 H, m), 3.54 (2 H, d, J = 6.36 Hz), 3.90-4.06 (2 H, m), 4.94 (1 H, s), 5.18 (1 H, t, J = 6.36 Hz) | B | 359 |
| 5 | 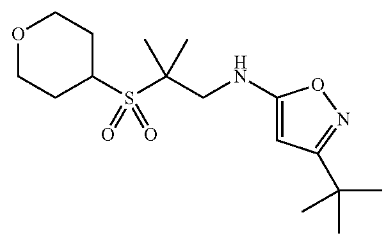 [SMILES: CC(C)(C)c1cc(NCC(C)(C)S(=O)(=O)C2CCOCC2)on1] | (400 MHz, CHLOROFORM-d) δ ppm 1.28 (9 H, s), 1.49 (6 H, s), 1.85-2.19 (4 H, m), 3.27-3.51 (3 H, m), 3.56 (2 H, d, J = 6.36 Hz), 4.03-4.23 (2 H, m), 4.93 (1 H, s), 5.25 (1 H, s) | D | 345 |
| 6 | 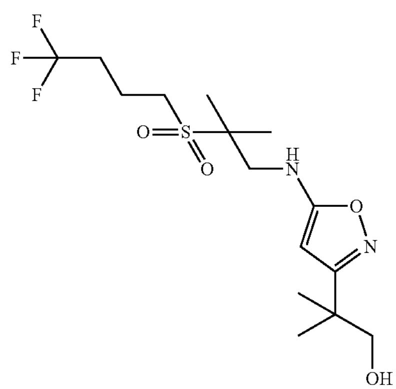 [SMILES: CC(C)(CO)c1cc(NCC(C)(C)S(=O)(=O)CCCC(F)(F)F)on1] | (250 MHz, CHLOROFORM-d) δ ppm 1.24 (6 H, s), 1.46 (6 H, s), 2.12-2.27 (2 H, m), 2.29-2.43 (3 H, m), 3.04 (2 H, t, J = 7.31 Hz), 3.55 (2 H, d, J = 6.24 Hz), 3.61 (2 H, s), 4.96 (1 H, s), 5.32-5.46 (1 H, m). | C | 387 |
| 7 | 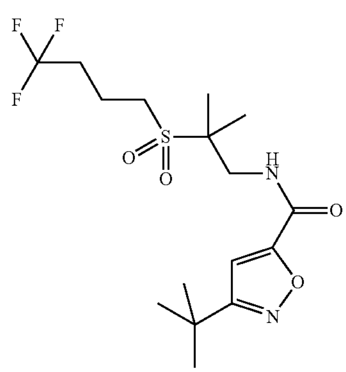 [SMILES: CC(C)(C)c1cc(C(=O)NCC(C)(C)S(=O)(=O)CCCC(F)(F)F)on1] | (500 MHz, CHLOROFORM-d) δ ppm 1.33-1.39 (9 H, m), 1.47 (6 H, s), 2.24 (2 H, quin, J = 7.49 Hz), 2.32-2.43 (2 H, m), 3.06 (2 H, t, J = 7.49 Hz), 3.85 (2 H, d, J = 6.31 Hz), 6.84 (1 H, s), 7.37 (1 H, t, J = 5.99 Hz) | E | 399 |

TABLE 4-continued

| Example | Structure | ¹H-NMR | Method | m/z [M + H] |
|---|---|---|---|---|
| 8 | 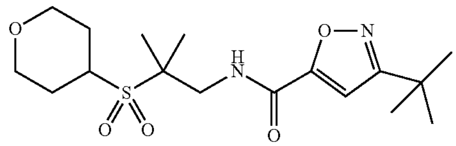 [SMILES: CC(C)(C)c1cc(C(=O)NCC(C)(C)S(=O)(=O)C2CCOCC2)on1] | (500 MHz, CHLOROFORM-d) δ ppm 1.36 (9 H, s), 1.49 (6 H, s), 1.95-2.03 (2 H, m), 2.02-2.13 (2 H, m), 3.36-3.49 (3 H, m), 3.85 (2 H, d, J = 6.15 Hz), 4.12 (2 H, dt, J = 9.62, 2.29 Hz), 6.83 (1 H, s), 7.47 (1 H, t, J = 5.99 Hz) | E | 373 |
| 9 | 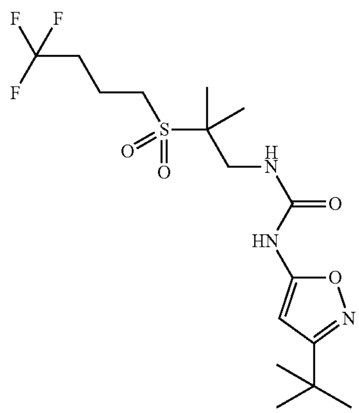 [SMILES: CC(C)(C)c1cc(NC(=O)NCC(C)(C)S(=O)(=O)CCCC(F)(F)F)on1] | (500 MHz, CHLOROFORM-d) δ ppm 1.32 (9 H, s), 1.48 (6 H, s), 2.16-2.28 (2 H, m), 2.29-2.43 (2 H, m), 3.07 (2 H, t, J = 7.49 Hz), 3.74 (2 H, d, J = 6.15 Hz), 5.99 (1 H, s), 6.18 (1 H, t, J = 5.36 Hz), 8.18 (1 H, br. s.) | F | 414 |
| 10 | 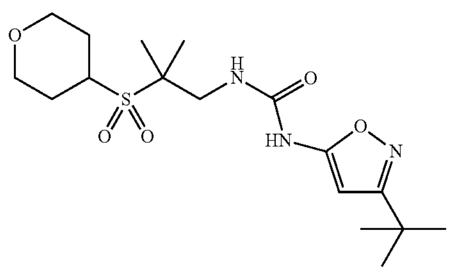 [SMILES: CC(C)(C)c1cc(NC(=O)NCC(C)(C)S(=O)(=O)C2CCOCC2)on1] | (500 MHz, CHLOROFORM-d) δ ppm 1.32 (9 H, s), 1.50 (6 H, s), 1.92-2.12 (4 H, m), 3.37-3.51 (3 H, m), 3.74 (2 H, d, J = 6.15 Hz), 4.11 (2 H, dd, J = 11.74, 2.76 Hz), 6.01 (1 H, s), 6.24 (1 H, t, J = 5.83 Hz), 8.13 (1 H, br. s.) | F | 388 |
| 11 | 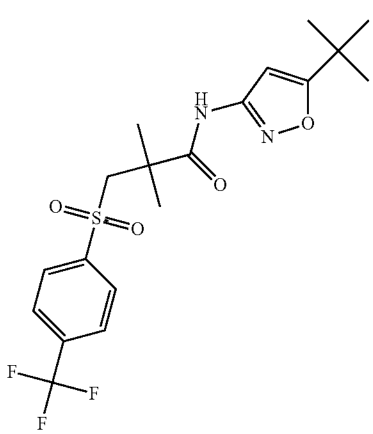 | (400 MHz, CHLOROFORM-d) δ ppm 1.26 (9 H, s), 1.52 (6 H, s), 3.53 (2 H, s), 6.54 (1 H, s), 7.72 (2 H, d, J = 8.23 Hz), 7.99 (2 H, d, J = 8.23 Hz), 8.81 (1 H, s) | G | 433 |

TABLE 4-continued
| Example | Structure | ¹H-NMR | Method | m/z [M + H] |
|---|---|---|---|---|
| 12 | 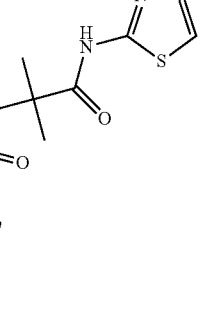 | (400 MHz, CHLOROFORM-d) δ ppm 1.25 (9 H, s), 1.54 (6 H, s), 3.56 (2 H, s), 6.48 (1 H, s), 7.68 (2 H, d, J = 8.23 Hz), 7.97 (2 H, d, J = 8.23 Hz), 9.15 (1 H, br. s.) | G | 449 |
| 13 | 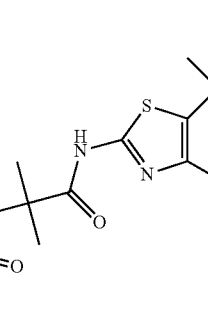 | (400 MHz. CHLOROFORM-d) δ ppm 1.38 (9 H, s), 1.50 (6 H, s), 2.42 (3 H, s), 3.72 (2 H, s), 7.71 (2 H, d, J = 8.05 Hz), 7.97 (2 H, d, J = 7.50 Hz) | G | 463 |
| 14 | 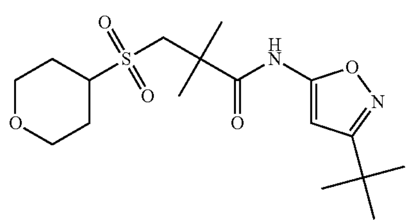 [SMILES: CC(C)(CS(=O)(=O)C1CCOCC1)C(=O)Nc1cc(C(C)(C)C)no1] | (500 MHz, CHLOROFORM-d) δ ppm 1.33 (9 H, s), 1.52-1.68 (8 H, m), 1.84-1.97 (2 H, m), 1.97-2.08 (2 H, m), 3.08 (1 H, tt, J = 12.04, 3.88 Hz), 3.33-3.46 (4 H, m), 4.07-4.18 (2 H, m), 6.32 (1 H, s), 8.43 (1 H, s) | H | 373 |
| 15 | 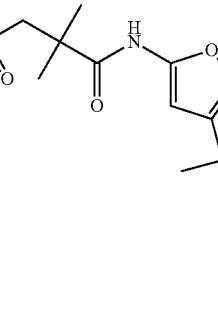 | (500 MHz, CHLOROFORM-d) δ ppm 1.31 (6 H, s), 1.58 (6 H, s), 2.15 (2 H, quin, J = 7.63 Hz), 2.24-2.39 (3 H, m), 3.05-3.17 (2 H, m), 3.46 (2 H, s), 3.68 (2 H, s), 6.35 (1 H, s), 8.46 (1 H, s) | H | 415 |

TABLE 4-continued

| Example | Structure | ¹H-NMR | Method | m/z [M + H] |
|---|---|---|---|---|
| 16 | 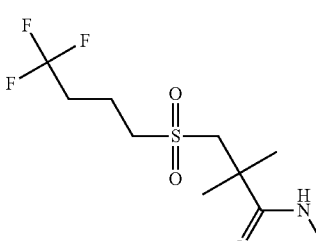 | (500 MHz, CHLOROFORM-d) δ ppm 1.48 (9 H, s), 1.63 (6 H, s), 1.81-1.97 (2 H, m), 1.96-2.09 (2 H, m), 2.98-3.21 (1 H, m), 3.34 (1 H, s), 3.35-3.45 (2 H, m), 3.49 (1 H, s), 4.01-4.22 (2 H, m) | H | 390 |
| 17 | 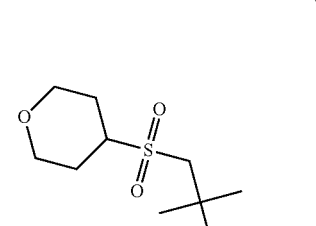 | (500 MHz, CHLOROFORM-d) δ ppm 1.35 (9 H, s), 1.60 (6 H, s), 2.05-2.21 (2 H, m), 2.24-2.44 (2 H, m), 3.05-3.21 (2 H, m), 3.47 (2 H, s), 6.33 (1 H, s), 8.41 (1 H, br. s.) | H | 399 |
| 18 | 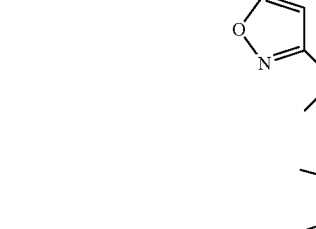 | (500 MHz, CHLOROFORM-d) δ ppm 1.31 (6 H, s), 1.59 (6 H, s), 1.86-1.97 (2 H, m), 1.99-2.07 (2 H, m), 3.09 (1 H, tt, J = 12.02, 3.82 Hz), 3.36-3.45 (4 H, m), 3.68 (2 H, s), 4.14 (2 H, dd, J = 11.59, 4.02 Hz), 6.34 (1 H, s), 8.49 (1 H, s) | H | 389 |
| 19 | 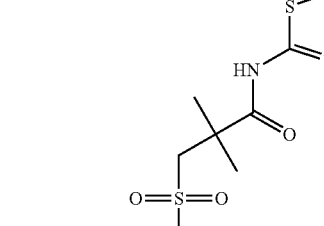 | (500 MHz, CHLOROFORM-d) δ ppm 1.47 (9 H, s), 1.66 (6 H, s), 2.06-2.15 (2 H, m), 2.22-2.31 (2 H, m), 3.09 (2H, t, J = 7.63 Hz), 3.71 (2 H, s) | H | 416 |

Assessment of Biological Properties

The biological properties of the compounds of the formula I are assessed using the assays described below.

A. Human CB1 and CB2 Receptor Binding:

Experimental Method:

CB2 membranes are purchased and made from HEK293 EBNA cells stably transfected with human CB2 receptor cDNA (Perkin Elmer Life and Analytical Sciences). CB1 membranes are isolated from HEK cells stably co-transfected with human CB1 receptor and Gα16 cDNA's. The membrane preparation is bound to scintillation beads (Ysi-Poly-L-lysine SPA beads, GE Healthcare) for 4 h at room temperature in assay buffer containing 50 mM Tris, pH 7.5, 2.5 mM EDTA, 5 mM MgCl$_2$, 0.8% fatty acid free Bovine Serum Albumin Unbound membrane is removed by washing in assay buffer. Membrane-bead mixture is added to 96-well assay plates in the amounts of 15 ug membrane per well (CB2) or 2.5 ug per well (CB1) and 1 mg SPA bead per well. Compounds are added to the membrane-bead mixture in dose-response concentrations ranging from $1 \times 10^{-5}$ M to $1 \times 10^{-10}$ M with 0.25% DMSO, final. The competition reaction is initiated with the addition of $^3$H-CP55940 (Perkin Elmer Life and Analytical Sciences) at a final concentration of 1.5 nM (CB2) or 2.5 nM (CB1). The reaction is incubated at room temperature for 18 h and read on TopCount NXT plate reader. Total and non-specific binding is determined in the absence and presence of 1.25 uM Win 55212 (Sigma). IC50 values for each compound are calculated as the concentration of compound that inhibits the specific binding of the radioactively labeled ligand to the receptor by 50% using the XLFit 4.1 four parameter logistic model. IC50 values are converted to inhibition constant (Ki) values using Cheng-Prusoff equation.

B. CB2R Mediated Modulation of cAMP Synthesis:

Compounds of the invention are evaluated for their CB2 agonist or inverse agonistic activity in accordance with the following experimental method. Compounds which are shown to bind to CB2 by the binding assay described above but which are not shown to exhibit CB2R-mediated modulation of cAMP synthesis by this assay are presumed to be CB2 antagonists.

Experimental Method:

CHO cells expressing human CB2R (Euroscreen) are plated at a density of 5000 cells per well in 384 well plates and incubated overnight at 37° C. After removing the media, the cells are treated with test compounds diluted in stimulation buffer containing 1 mM IBMX, 0.25% BSA and 10 uM Forskolin. The assay is incubated for 30 minutes at 37° C. Cells are lysed and the cAMP concentration is measured using DiscoverX-XS cAMP kit, following the manufacturer's protocol. In this setting, agonists will decrease forskolin induced production of cAMP while inverse agonists will further increase forskolin induced production of cAMP. EC50 of agonists are calculated as follows. The maximal amount of cAMP produced by forskolin compared to the level of cAMP inhibited by 1 uM CP55940 is defined as 100%. The EC50 value of each test compound is determined as the concentration at which 50% of the forskolin-stimulated cAMP synthesis is inhibited. Data is analyzed using a four-parameter logistic model. (Model 205 of XLfit 4.0).

C. CB1R Mediated Modulation of cAMP Synthesis:

Compounds of the invention are evaluated for their CB1 agonist or inverse agonistic activity in accordance with the following experimental method. Compounds which are shown to bind to CB1 by the binding assay described above but which are not shown to exhibit CB1R-mediated modulation of cAMP synthesis by this assay are presumed to be CB1 antagonists.

Experimental Method:

CHO cells expressing human CB1R (Euroscreen) are plated at a density of 5000 cells per well in 384 well plates and incubated overnight at 37° C. After removing the media, the cells are treated with test compounds diluted in stimulation buffer containing 1 mM IBMX, 0.25% BSA and 10 uM Forskolin. The assay is incubated for 30 minutes at 37° C. Cells are lysed and the cAMP concentration is measured using DiscoverX-XS cAMP kit, following the manufacturer's protocol. In this setting, agonists will decrease forskolin induced production of cAMP while inverse agonists will further increase forskolin induced production of cAMP. EC50 of agonists are calculated as follows. The maximal amount of cAMP produced by forskolin compared to the level of cAMP inhibited by 1 uM CP55940 is defined as 100%. The EC50 value of each test compound is determined as the concentration at which 50% of the forskolin-stimulated cAMP synthesis is inhibited. Data is analyzed using a four-parameter logistic model. (Model 205 of XLfit 4.0).

Compounds Having Agonist Activity

Through the use of the above described assays compounds are found to exhibit agonistic activity and thus to be particularly well suited for the treatment of pain as well as for the treatment of inflammation. Preferred compounds of the invention will have an activity range of CB2 (<500 nM).

Therapeutic Use

As can be demonstrated by the assays described above, the compounds of the invention are useful in modulating the CB2 receptor function. By virtue of this fact, these compounds have therapeutic use in treating disease-states and conditions mediated by the CB2 receptor function or that would benefit from modulation of the CB2 receptor function.

As the compounds of the invention modulate the CB2 receptor function, they have very useful anti-inflammatory and immune-suppressive activity and they can be used in patients as drugs, particularly in the form of pharmaceutical compositions as set forth below, for the treatment of disease-states and conditions.

As noted before, those compounds which are CB2 agonists can also be employed for the treatment of pain.

The agonist, antagonist and inverse agonist compounds according to the invention can be used in patients as drugs for the treatment of the following disease-states or indications that are accompanied by inflammatory processes:

(i) Lung diseases: e.g. asthma, bronchitis, allergic rhinitis, emphysema, adult respiratory distress syndrome (ARDS), pigeon fancier's disease, farmer's lung, chronic obstructive pulmonary disease (COPD), asthma including allergic asthma (atopic or non-atopic) as well as exercise-induced bronchoconstriction, occupational asthma, viral- or bacterial exacerbation of asthma, other non-allergic asthmas and "wheezy-infant syndrome", pneumoconiosis, including aluminosis, anthracosis, asbestosis, chalicosis, ptilosis, siderosis, silicosis, tabacosis and byssinosis;

(ii) Rheumatic diseases or autoimmune diseases or musculoskeletal diseases: all forms of rheumatic diseases, especially rheumatoid arthritis, acute rheumatic fever, and polymyalgia rheumatica; reactive arthritis; rheumatic soft tissue diseases; inflammatory soft tissue diseases of other genesis; arthritic symptoms in degenerative joint diseases (arthroses); tendinitis, bursitis, osteoarthritis, traumatic arthritis; collagenoses of any genesis, e.g., systemic lupus erythematosus, scleroderma, polymyositis, dermatomyositis, Sjögren syndrome, Still disease, Felty syndrome; and osteoporosis and other bone resorption diseases;

(iii) Allergic diseases: all forms of allergic reactions, e.g., angioneurotic edema, hay fever, insect bites, allergic reactions to drugs, blood derivatives, contrast agents, etc., anaphylactic shock (anaphylaxis), urticaria, angioneurotic edema, and contact dermatitis;

(iv) Vascular diseases: panarteritis nodosa, polyarteritis nodosa, periarteritis nodosa, arteritis temporalis, Wegner granulomatosis, giant cell arthritis, atherosclerosis, reperfusion injury and erythema nodosum;

(v) Dermatological diseases: e.g. dermatitis, psoriasis; sunburn, burns, eczema;

(vi) Renal diseases: e.g. nephrotic syndrome; and all types of nephritis, e.g., glomerulonephritis; pancreatits;

(vii) Hepatic diseases: e.g. acute liver cell disintegration; acute hepatitis of various genesis, e.g., viral, toxic, drug-induced; and chronically aggressive and/or chronically intermittent hepatitis;

(viii) Gastrointestinal diseases: e.g. inflammatory bowel diseases, irritable bowel syndrome, regional enteritis (Crohns disease), colitis ulcerosa; gastritis; aphthous ulcer, celiac disease, regional ileitis, gastroesophageal reflux disease;

(ix) Neuroprotection: e.g. in the treatment of neurodegeneration following stroke; cardiac arrest; pulmonary bypass; traumatic brain injury; spinal cord injury or the like;

(x) Eye diseases: allergic keratitis, uveitis, or iritis; conjunctivitis; blepharitis; neuritis nervi optici; choroiditis; glaucoma and sympathetic ophthalmia;

(xi) Diseases of the ear, nose, and throat (ENT) area: e.g. tinnitus; allergic rhinitis or hay fever; otitis externa; caused by contact eczema, infection, etc.; and otitis media;

(xii) Neurological diseases: e.g. brain edema, particularly tumor-related brain edema; multiple sclerosis; acute encephalomyelitis; meningitis; acute spinal cord injury; trauma; dementia, particularly degenerative dementia (including senile dementia, Alzheimer's disease; Parkinson's disease and Creutzfeldt-Jacob disease; Huntington's chorea, Pick's disease; motor neuron disease), vascular dementia (including multi-infarct dementia) as well as dementia associated with intracranial space occupying lesions; infections and related conditions (including HIV infection); Guillain-Barre syndrome; myasthenia gravis, stroke; and various forms of seizures, e.g., nodding spasms;

(xiii) Blood diseases: acquired hemolytic anemia; aplastic anemia, and idiopathic thrombocytopenia;

(xiv) Tumor diseases: acute lymphatic leukemia; Hodgkin's disease, malignant lymphoma; lymphogranulomatoses; lymphosarcoma; solid malignant tumors; extensive metastases;

(xv) Endocrine diseases: endocrine ophthalmopathy; endocrine orbitopathia; thyrotoxic crisis; Thyroiditis de Quervain; Hashimoto thyroiditis; Morbus Basedow; granulomatous thyroiditis; struma lymphomatosa; and Graves disease; type I diabetes (insulin-dependent diabetes);

(xvi) Organ and tissue transplantations and graft-versus-host diseases;

(xvii) Severe states of shock, e.g., septic shock, anaphylactic shock, and systemic inflammatory response syndrome (SIRS);

(xviii) Acute pain such as dental pain, perioperative, postoperative pain, traumatic pain, muscle pain, pain in burned skin, sun burn, trigeminal neuralgia, sun burn; spasm of the gastrointestinal tract or uterus, colics;

(xix) Visceral pain such as pain associated with chronic pelvic pain, pancreatitis, peptic ulcer, interstitial cystitis, renal colic, angina, dysmenorrhoea, menstruation, gynaecological pain, irritable bowel syndrome (IBS), non-ulcer dyspepsia, non-cardiac chest pain, myocardial ischemia;

(xx) Neuropathic pain such as low back pain, non-herpetic neuralgia, post herpetic neuralgia, diabetic neuropathy, nerve injury, acquired immune deficiency syndrome (AIDS) related neuropathic pain, head trauma, painful traumatic mononeuropathy, toxin and chemotherapy induced pain, phantom limb pain, painful polyneuropathy, thalamic pain syndrome, post-stroke pain, central nervous system injury, post surgical pain, stump pain, repetitive motion pain, pain induced by post mastectomy syndrome, multiple sclerosis, root avulsions, postthoracotomy syndrome, neuropathic pain associated hyperalgesia and allodynia.

(xxi) Inflammatory/nociceptive pain induced by or associated with disorders such as osteoarthritis, rheumatoid arthritis, rheumatic disease, teno-synovitis, gout, vulvodynia, myofascial pain (muscular injury, fibromyalgia), tendonitis, osteoarthritis, juvenile arthritis, spondylitis, gouty arthritis, psoriatic arthritis, muscoskeletal pain, fibromyalgia, sprains and strains, sympathetically maintained pain, myositis, pain associated with migraine, toothache, influenza and other viral infections such as the common cold, rheumatic fever, systemic lupus erythematosus;

(xxii) Cancer pain induced by or associated with tumors such as lymphatic leukemia; Hodgkin's disease, malignant lymphoma; lymphogranulomatoses; lymphosarcoma; solid malignant tumors; extensive metastases;

(xxiii) Headache such as cluster headache, migraine with and without aura, tension type headache, headache with different origins, headache disorders including prophylactic and acute use;

(xxiv) various other disease-states or conditions including, restenosis following percutaneous transluminal coronary angioplasty, acute and chronic pain, atherosclerosis, reperfusion injury, congestive heart failure, myocardial infarction, thermal injury, multiple organ injury secondary to trauma, necrotizing enterocolitis and syndromes associated with hemodialysis, leukopheresis, and granulocyte transfusion, sarcoidosis, gingivitis, pyrexia. edema resulting from trauma associated with burns, sprains or fracture, cerebral oedema and angioedema, Diabetes such as diabetic vasculopathy, diabetic neuropathy, diabetic retinopathy, post capillary resistance or diabetic symptoms associated with insulitis (e.g. hyperglycemia, diuresis, proteinuria and increased nitrite and kallikrein urinary excretion).

Other indications include: epilepsy, septic shock e.g. as antihypovolemic and/or antihypotensive agents, cancer, sepsis, osteoporosis, benign prostatic hyperplasia and hyperactive bladder, pruritis, vitiligo, general gastrointestinal disorders, disturbances of visceral motility at respiratory, genitourinary, gastrointestinal or vascular regions, wounds, burns, tissue damage and postoperative fever, syndromes associated with Itching.

Besides being useful for human treatment, these compounds are also useful for veterinary treatment of companion animals, exotic animals and farm animals, including mammals, rodents, and the like.

For treatment of the above-described diseases and conditions, a therapeutically effective dose will generally be in the range from about 0.01 mg to about 100 mg/kg of body weight per dosage of a compound of the invention; preferably, from about 0.1 mg to about 20 mg/kg of body weight per dosage. For Example, for administration to a 70 kg person, the dosage range would be from about 0.7 mg to about 7000 mg per dosage of a compound of the invention, preferably from about 7.0 mg to about 1400 mg per dosage. Some degree of routine dose optimization may be required to determine an optimal dosing level and pattern. The active ingredient may be administered from 1 to 6 times a day.

General Administration and Pharmaceutical Compositions

When used as pharmaceuticals, the compounds of the invention are typically administered in the form of a pharmaceutical composition. Such compositions can be prepared using procedures well known in the pharmaceutical art and comprise at least one compound of the invention. The compounds of the invention may also be administered alone or in combination with adjuvants that enhance stability of the compounds of the invention, facilitate administration of pharmaceutical compositions containing them in certain embodiments, provide increased dissolution or dispersion, increased inhibitory activity, provide adjunct therapy, and the like. The compounds according to the invention may be used on their own or in conjunction with other active substances according to the invention, optionally also in conjunction with other pharmacologically active substances. In general, the compounds of this invention are administered in a therapeutically or pharmaceutically effective amount, but may be administered in lower amounts for diagnostic or other purposes.

Administration of the compounds of the invention, in pure form or in an appropriate pharmaceutical composition, can be carried out using any of the accepted modes of administration of pharmaceutical compositions. Thus, administration can be, for Example, orally, buccally (e.g., sublingually), nasally, parenterally, topically, transdermally, vaginally, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, preferably in unit dosage forms suitable for simple administration of precise dosages. The pharmaceutical compositions will generally include a conventional pharmaceutical carrier or excipient and a compound of the invention as the/an active agent, and, in addition, may include other medicinal agents, pharmaceutical agents, carriers, adjuvants, diluents, vehicles, or combinations thereof. Such pharmaceutically acceptable excipients, carriers, or additives as well as methods of making pharmaceutical compositions for various modes or administration are well-known to those of skill in the art. The state of the art is evidenced, e.g., by Remington: The Science and Practice of Pharmacy, 20th Edition, A. Gennaro (ed.), Lippincott Williams & Wilkins, 2000; Handbook of Pharmaceutical Additives, Michael & Irene Ash (eds.), Gower, 1995; Handbook of Pharmaceutical Excipients, A. H. Kibbe (ed.), American Pharmaceutical Ass'n, 2000; H. C. Ansel and N. G. Popovish, Pharmaceutical Dosage Forms and Drug Delivery Systems, 5th ed., Lea and Febiger, 1990; each of which is incorporated herein by reference in their entireties to better describe the state of the art.

As one of skill in the art would expect, the forms of the compounds of the invention utilized in a particular pharmaceutical formulation will be selected (e.g., salts) that possess suitable physical characteristics (e.g., water solubility) that is required for the formulation to be efficacious.

Pharmaceutical compositions suitable for buccal (sub-lingual) administration include lozenges comprising a compound of the present invention in a flavored base, usually sucrose, and acacia or tragacanth, and pastilles comprising the compound in an inert base such as gelatin and glycerin or sucrose and acacia.

Pharmaceutical compositions suitable for parenteral administration comprise sterile aqueous preparations of a compound of the present invention. These preparations are preferably administered intravenously, although administration can also be effected by means of subcutaneous, intramuscular, or intradermal injection. Injectable pharmaceutical formulations are commonly based upon injectable sterile saline, phosphate-buffered saline, oleaginous suspensions, or other injectable carriers known in the art and are generally rendered sterile and isotonic with the blood. The injectable pharmaceutical formulations may therefore be provided as a sterile injectable solution or suspension in a nontoxic parenterally acceptable diluent or solvent, including 1,3-butanediol, water, Ringer's solution, isotonic sodium chloride solution, fixed oils such as synthetic mono- or diglycerides, fatty acids such as oleic acid, and the like. Such injectable pharmaceutical formulations are formulated according to the known art using suitable dispersing or setting to agents and suspending agents. Injectable compositions will generally contain from 0.1 to 5% w/w of a compound of the invention.

Solid dosage forms for oral administration of the compounds include capsules, tablets, pills, powders, and granules. For such oral administration, a pharmaceutically acceptable composition containing a compound(s) of the invention is formed by the incorporation of any of the normally employed excipients, such as, for example, pharmaceutical grades of mannitol, lactose, starch, pregelatinized starch, magnesium stearate, sodium saccharine, talcum, cellulose ether derivatives, glucose, gelatin, sucrose, citrate, propyl gallate, and the like. Such solid pharmaceutical formulations may include formulations, as are well-known in the art, to provide prolonged or sustained delivery of the drug to the gastrointestinal tract by any number of mechanisms, which include, but are not limited to, pH sensitive release from the dosage form based on the changing pH of the small intestine, slow erosion of a tablet or capsule, retention in the stomach based on the physical properties of the formulation, bioadhesion of the dosage form to the mucosal lining of the intestinal tract, or enzymatic release of the active drug from the dosage form.

Liquid dosage forms for oral administration of the compounds include emulsions, microemulsions, solutions, suspensions, syrups, and elixirs, optionally containing pharmaceutical adjuvants in a carrier, such as, for example, water, saline, aqueous dextrose, glycerol, ethanol and the like. These compositions can also contain additional adjuvants such as wetting, emulsifying, suspending, sweetening, flavoring, and perfuming agents.

Topical dosage forms of the compounds include ointments, pastes, creams, lotions, gels, powders, solutions, sprays, inhalants, eye ointments, eye or ear drops, impregnated dressings and aerosols, and may contain appropriate conventional additives such as preservatives, solvents to assist drug penetration and emollients in ointments and creams. Topical application may be once or more than once per day depending upon the usual medical considerations. Furthermore, preferred compounds for the present invention can be administered in intranasal form via topical use of suitable intranasal vehicles. The formulations may also contain compatible conventional carriers, such as cream or ointment bases and ethanol or oleyl alcohol for lotions. Such carriers may be present as from about 1% up to about 98% of the formulation, more usually they will form up to about 80% of the formulation.

Transdermal administration is also possible. Pharmaceutical compositions suitable for transdermal administration can be presented as discrete patches adapted to remain in intimate contact with the epidermis of the recipient for a prolonged period of time. To be administered in the form of a transdermal delivery system, the dosage administration will, of course, be continuous rather than intermittent throughout the dosage regimen. Such patches suitably contain a compound of the invention in an optionally buffered, aqueous solution, dissolved and/or dispersed in an adhesive, or dispersed in a polymer. A suitable concentration of the active compound is about 1% to 35%, preferably about 3% to 15%.

For administration by inhalation, the compounds of the invention are conveniently delivered in the form of an aerosol spray from a pump spray device not requiring a propellant gas or from a pressurized pack or a nebulizer with the use of a suitable propellant, e.g., dichlorodifluoromethane, trichlorofluoromethane, dichlorotetrafluoroethane, tetrafluoroethane, heptafluoropropane, carbon dioxide, or other suitable gas. In any case, the aerosol spray dosage unit may be determined by providing a valve to deliver a metered amount so that the resulting metered dose inhaler (MDI) is used to administer the compounds of the invention in a reproducible and controlled way. Such inhaler, nebulizer, or atomizer devices are known in the prior art, for example, in PCT International Publication Nos. WO 97/12687 (particularly FIG. 6 thereof, which is the basis for the commercial RESPIMAT® nebulizer); WO 94/07607; WO 97/12683; and WO 97/20590, to which reference is hereby made and each of which is incorporated herein by reference in their entireties.

Rectal administration can be effected utilizing unit dose suppositories in which the compound is admixed with low-melting water-soluble or insoluble solids such as fats, cocoa butter, glycerinated gelatin, hydrogenated vegetable oils, mixtures of polyethylene glycols of various molecular weights, or fatty acid esters of polyethylene glycols, or the like. The active compound is usually a minor component, often from about 0.05 to 10% by weight, with the remainder being the base component.

In all of the above pharmaceutical compositions, the compounds of the invention are formulated with an acceptable carrier or excipient. The carriers or excipients used must, of course, be acceptable in the sense of being compatible with the other ingredients of the composition and must not be deleterious to the patient. The carrier or excipient can be a solid or a liquid, or both, and is preferably formulated with the compound of the invention as a unit-dose composition, for example, a tablet, which can contain from 0.05% to 95% by weight of the active compound. Such carriers or excipients include inert fillers or diluents, binders, lubricants, disintegrating agents, solution retardants, resorption accelerators, absorption agents, and coloring agents. Suitable binders include starch, gelatin, natural sugars such as glucose or β-lactose, corn sweeteners, natural and synthetic gums such as acacia, tragacanth or sodium alginate, carboxymethylcellulose, polyethylene glycol, waxes, and the like. Lubricants include sodium oleate, sodium stearate, magnesium stearate, sodium benzoate, sodium acetate, sodium chloride, and the like. Disintegrators include starch, methyl cellulose, agar, bentonite, xanthan gum, and the like.

Pharmaceutically acceptable carriers and excipients encompass all the foregoing additives and the like.

The invention claimed is:
1. A compound of the formula (I)

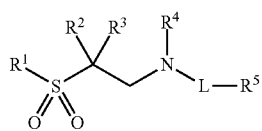

(I)

wherein:
$R^1$ is $C_{1-10}$ alkyl, $C_{3-10}$ cycloalkyl, 3-10 membered saturated heterocyclic ring, $C_{1-5}$ alkyl-heterocyclic ring, 5-10 membered mono or bicyclic heteroaryl ring or $C_{1-5}$ alkyl-heteroaryl ring, wherein each $R^1$ is optionally independently substituted with 1-3 substituents chosen from $C_{1-4}$ alkyl group, $C_{3-10}$ cycloalkyl, $C_{1-4}$ alkoxy, $C_{1-4}$ alkylsulfonyl, $C_{1-4}$ acyl, oxo, phenyl, cyano, hydroxyl and halogen;

$R^2$ and $R^3$ are $C_{1-4}$ alkyl or hydrogen with the proviso that both $R^2$ and $R^3$ cannot be hydrogen; or $R^2$ and $R^3$ together with the carbon atom to which they are attached form a 3- to 6-membered cycloalkyl ring or heterocyclic ring;

$R^4$ is hydrogen or methyl;

$R^5$ is 5 membered heteroaryl ring optionally independently substituted with 1-3 substituents chosen from $C_{1-4}$ alkyl group, cyano, —$C_{1-8}$ branched or unbranched alkyl —O—$R^6$, $C_{3-8}$-cycloalkyl-O—$R^6$, —$C_{1-3}$ branched or unbranched alkyl —$R^7$ and aryl-$R^8$ each $R^6$ is independently hydrogen, $C_{1-4}$ alkyl, —$C_{1-4}$ alkyl-O $C_{1-4}$ alkyl, or —$C_{1-4}$ alkyl-OH;

$R^7$ is a 5-6 membered heteroaryl ring;

$R^8$ is hydroxyl, $C_{1-6}$ alkoxy, $C_{1-4}$ alkylsulfonyl, cyano, halogen or $C_{1-4}$ alkyl L is a bond, —C(O)—, —C(O)—NH— or —$SO_2$—;

wherein any carbon atom on the formula (I) or any R substituent listed above is optionally partially or fully halogenated where possible;

or a pharmaceutically acceptable salt thereof.

2. The compound according to claim 1, and wherein $R^1$ is $C_{1-6}$ alkyl, cyclopropyl, cyclobutyl, cyclopentyl, cyclohexyl, cycloheptyl, cyclooctyl, —$CH_2$-cyclopropyl, —$CH_2$-cyclobutyl, —$CH_2$—$CH_2$-cyclopropyl, —$CH_2$—$CH_2$-cyclobutyl, tetrahydrofuranyl, tetrahydropyranyl, azetidinyl, piperidinyl, thiomorpholinyl, 1,1-dioxo-1$\lambda^6$-thiomorpholinyl, morpholinyl, pyrrolidinyl, piperazinyl, —$CH_2$— tetrahydrofuranyl, —$CH_2$-tetrahydropyranyl, —$CH_2$—$CH_2$-tetrahydrofuranyl, —$CH_2$—$CH_2$-tetrahydropyranyl, benzoxazolyl, benzothiazolyl, benzimidazolyl, oxazolyl, isoxazolyl, thiazolyl, pyrazolyl, pyrrolyl, imidazolyl, thienyl, thiadiazolyl, pyridinyl, pyrimidinyl, pyridazinyl, pyrazinyl, quinolinyl, isoquinolinyl, indolyl, benzofuranyl or benzopyranyl, wherein each $R^1$ is optionally independently substituted with 1-3 substituents chosen from $C_{1-4}$ alkyl group, $C_{1-4}$ alkoxy, $C_{1-4}$ alkylsulfonyl, $C_{1-4}$ acyl, oxo, phenyl, cyano, hydroxyl and halogen;

$R^2$ and $R^3$ are independently methyl, ethyl, n-propyl, iso-propyl, t-Butyl or hydrogen with the proviso that both $R^2$ and $R^3$ cannot be hydrogen; or $R^2$ and $R^3$ together with the carbon to which they are attached form a cyclopropyl, cyclobutyl, or cyclopentyl ring;

$R^4$ is hydrogen or methyl;

$R^5$ is isoxazolyl, thiazolyl, pyrazolyl, pyrrolyl, imidazolyl, thienyl, thiadiazolyl, tetrazolyl, oxazolyl, oxadiazolyl or furanyl, wherein each $R^5$ is optionally independently substituted with 1-3 substituents chosen from $C_{1-4}$ alkyl group, cyano, —$C_{1-8}$ branched or unbranched alkyl —O—$R^6$, -cycloalkyl-O—$R^6$, —$C_{1-3}$ branched, or unbranched alkyl —$R^7$ and phenyl-$R^8$;

each $R^6$ is independently hydrogen or $C_{1-4}$ alkyl, —$C_{1-4}$ alkyl-O$C_{1-4}$ alkyl, or —$C_{1-4}$ alkyl-OH;

$R^7$ is pyrazolyl, isoxazolyl, oxazolyl, oxadiazolyl or thiazolyl;

$R^8$ is hydroxyl, $C_{1-3}$ alkoxy, $C_{1-4}$ alkylsulfonyl, cyano, halogen or $C_{1-4}$ alkyl or a pharmaceutically acceptable salt thereof.

3. The compound according to claim 2, and wherein $R^1$ is $C_{1-6}$ alkyl, tetrahydropyranyl or —$CH_2$-tetrahydropyranyl wherein each $R^1$ is optionally independently substituted with 1-3 substituents chosen from $C_{1-4}$ alkyl group and halogen;

or a pharmaceutically acceptable salt thereof.

4. The compound according to claim 3, and wherein R² and R³ are methyl
or a pharmaceutically acceptable salt thereof.

5. The compound according to claim 4, and wherein
R⁴ is hydrogen;
R⁵ is isoxazolyl or pyrazolyl, wherein each R⁵ is optionally independently substituted with 1-3 substituents chosen from $C_{1-4}$ alkyl group and halogen;
or a pharmaceutically acceptable salt thereof.

6. The compound according to claim 2, and wherein
R¹ is $C_{1-6}$ alkyl, tetrahydropyranyl or —CH₂-tetrahydropyranyl wherein each R¹ is optionally independently substituted with 1-3 substituents chosen from $C_{1-4}$ alkyl group and halogen;
R² and R³ are methyl;
R⁴ is hydrogen;
R⁵ is isoxazolyl or pyrazolyl, wherein each R⁵ is optionally independently substituted with 1-3 substituents chosen from $C_{1-4}$ alkyl group and halogen;
or a pharmaceutically acceptable salt thereof.

7. The compound according to claim 6, and wherein
R¹ is $C_{1-4}$ alkyl, tetrahydropyranyl or —CH₂-tetrahydropyranyl, wherein each R¹ is optionally independently substituted with a substituent chosen from trifluoromethyl and chloro;
R⁵ is isoxazolyl or pyrazolyl, wherein each R⁵ is optionally independently substituted with 1-2 substituents chosen from $C_{1-4}$ alkyl group and trifluoromethyl
or a pharmaceutically acceptable salt thereof.

8. The compound according to claim 1, and wherein
R² and R³ are methyl;
or a pharmaceutically acceptable salt thereof.

9. The compound according to claim 8, and wherein
L is a bond
or a pharmaceutically acceptable salt thereof.

10. The compound according to claim 8, and wherein
L is —C(O)—;
or a pharmaceutically acceptable salt thereof.

11. The compound according to claim 8, and wherein
L is —C(O)—NH— or
a pharmaceutically acceptable salt thereof.

12. A compound of the formula (IA)

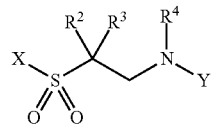

(IA)

wherein

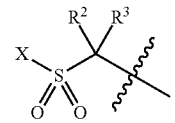

of the formula (IA) is chosen from column A1-A3 in Table I, and

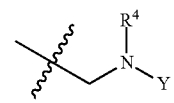

of the formula (IA) is chosen from column B2-B7 in Table I,

TABLE I

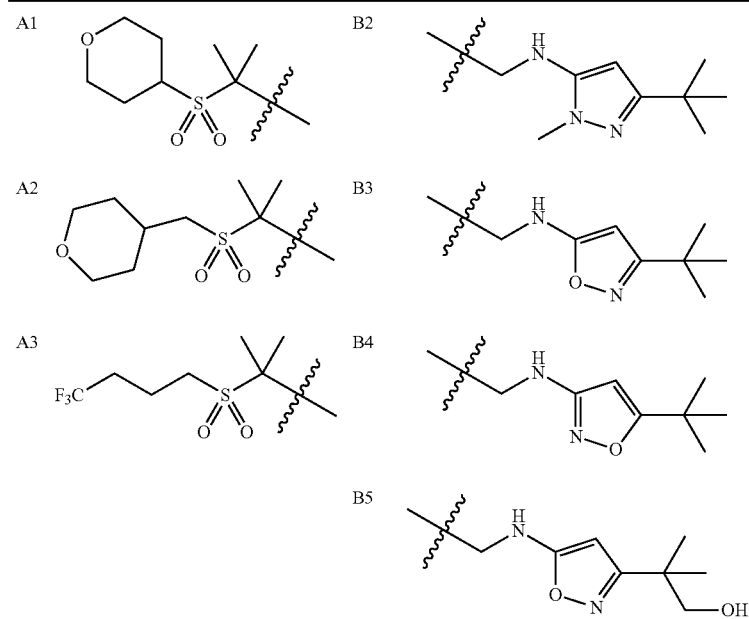

TABLE I-continued
B6 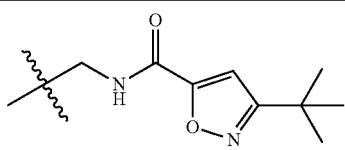
B7 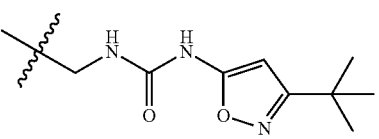 [SMILES: *CNC(=O)Nc1cc(C(C)(C)C)no1]
or a pharmaceutically acceptable salt thereof.
13. A compound chosen from:
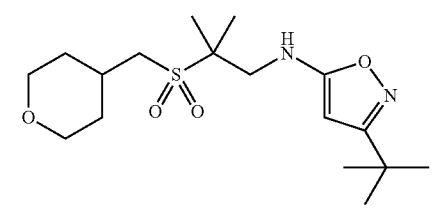
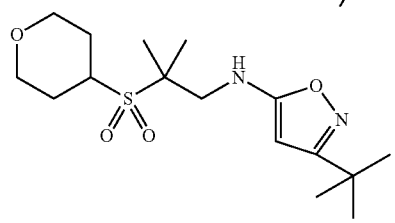
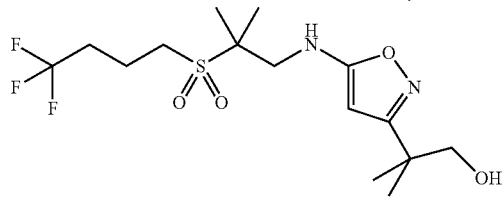
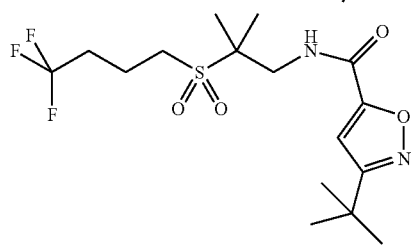
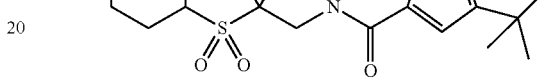
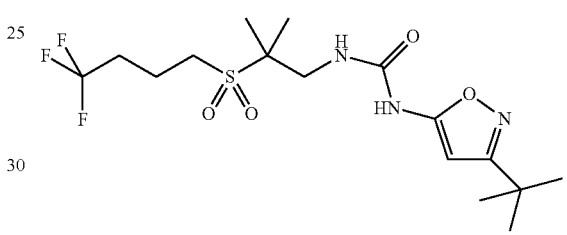
and
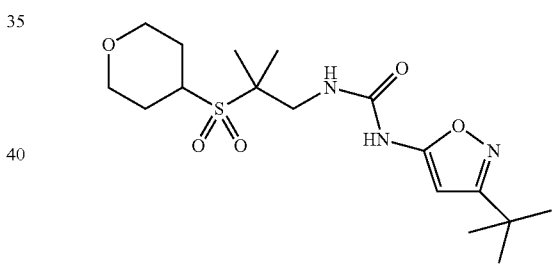
or a pharmaceutically acceptable salt thereof.
14. A pharmaceutical composition comprising a therapeutically effective amount of a compound according to claim 1 and one or more pharmaceutically acceptable carriers and/or adjuvants.
* * * * *